US008523900B2

(12) United States Patent
Jinno et al.

(10) Patent No.: US 8,523,900 B2
(45) Date of Patent: Sep. 3, 2013

(54) MEDICAL MANIPULATOR

(75) Inventors: Makoto Jinno, Kanagawa-ken (JP); Shunsuke Iwayoshi, Kanagawa-ken (JP)

(73) Assignee: Terumo Kabushiki Kaisha, Tokyo (JP)

( * ) Notice: Subject to any disclaimer, the term of this patent is extended or adjusted under 35 U.S.C. 154(b) by 649 days.

(21) Appl. No.: 12/697,704

(22) Filed: Feb. 1, 2010

(65) Prior Publication Data
US 2010/0198253 A1 Aug. 5, 2010

(30) Foreign Application Priority Data

Feb. 3, 2009 (JP) ................................ 2009-022902
Mar. 27, 2009 (JP) ................................ 2009-078992

(51) Int. Cl.
*A61B 17/00* (2006.01)
(52) U.S. Cl.
USPC ......................................................... 606/208
(58) Field of Classification Search
USPC ............. 606/1, 129, 130, 174, 205, 206, 207, 606/208; 227/175.1; 414/729, 733, 735, 414/738, 739, 741, 7; 901/21, 29, 31, 36, 901/39
See application file for complete search history.

(56) References Cited

U.S. PATENT DOCUMENTS

| | | | |
|---|---|---|---|
| 5,797,900 A * | 8/1998 | Madhani et al. ................... 606/1 |
| 6,889,116 B2 | 5/2005 | Jinno |
| 7,300,373 B2 | 11/2007 | Jinno et al. |
| 2002/0111621 A1 * | 8/2002 | Wallace et al. ................. 606/41 |
| 2004/0199147 A1 | 10/2004 | Nishizawa et al. |
| 2004/0266574 A1 * | 12/2004 | Jinno et al. .................... 474/153 |
| 2007/0208375 A1 * | 9/2007 | Nishizawa et al. ........... 606/205 |
| 2008/0147090 A1 * | 6/2008 | Seibold et al. ................ 606/130 |
| 2009/0112229 A1 * | 4/2009 | Omori et al. .................. 606/130 |
| 2009/0112230 A1 * | 4/2009 | Jinno ............................ 606/130 |

FOREIGN PATENT DOCUMENTS

| | | |
|---|---|---|
| EP | 1 977 713 A2 | 10/2008 |
| JP | 2002-102248 | 4/2002 |
| JP | 2004-301275 | 10/2004 |

* cited by examiner

*Primary Examiner* — Gary Jackson
*Assistant Examiner* — Jonathan Hollm
(74) *Attorney, Agent, or Firm* — Oblon, Spivak, McClelland, Maier & Neustadt, L.L.P.

(57) ABSTRACT

A medical manipulator includes a wire movable in opposite directions, a driven wire having both ends thereof connected to the wire, an end effector of a distal-end working unit, a transmitting member, a crescent driven member integral with the transmitting member, and a return pulley. The transmitting member, the crescent driven member, and the return pulley are successively arranged in this order from the proximal end of the medical manipulator. When the driven wire is moved in opposite directions, the transmitting member also moves in opposite directions. At this time, the crescent driven member moves toward the return pulley, and the proximal-end portion of the return pulley enters a cavity of the crescent driven member.

19 Claims, 35 Drawing Sheets

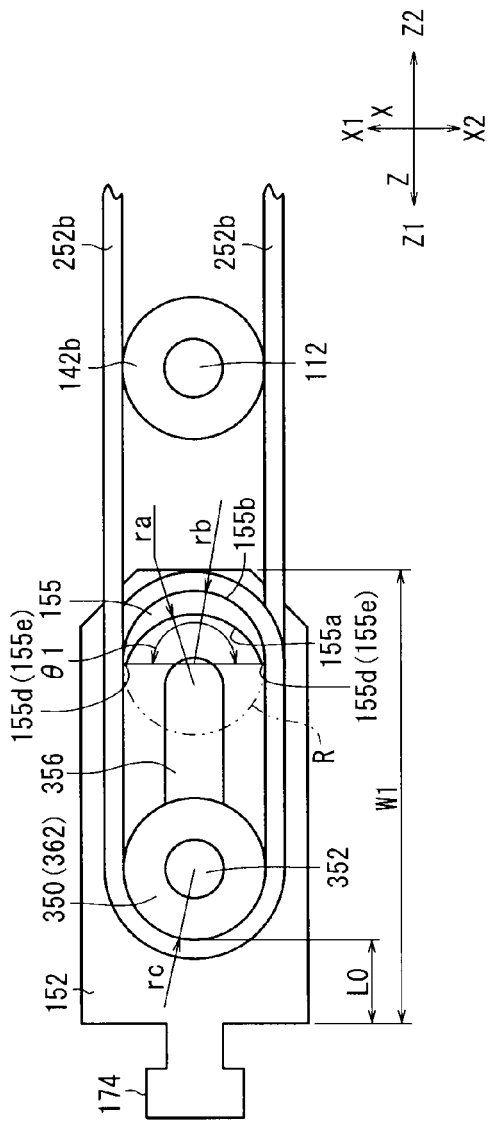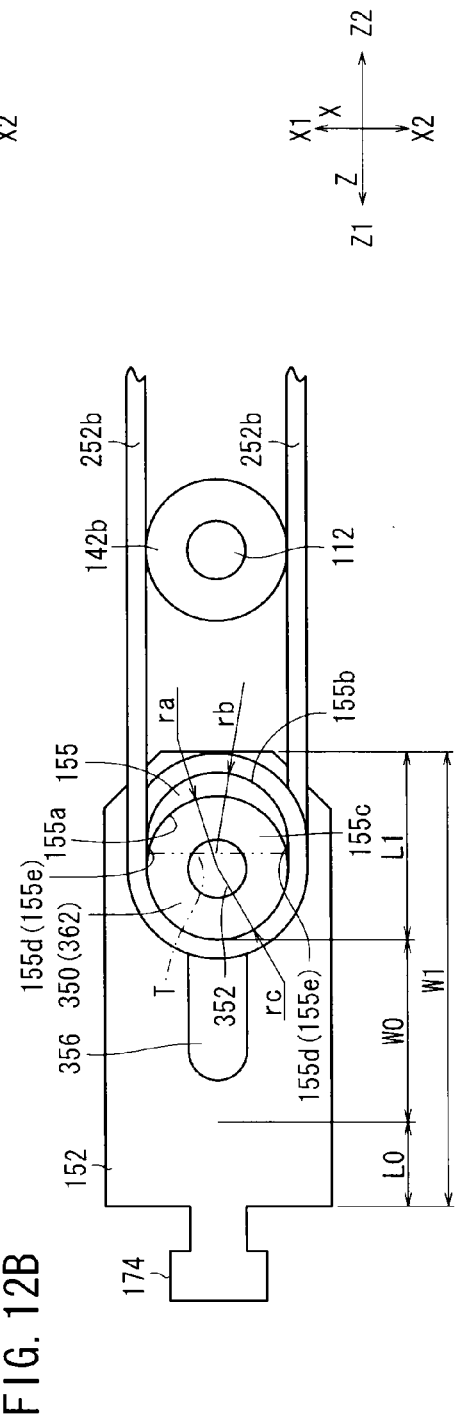

MEDICAL MANIPULATOR

CROSS-REFERENCE TO RELATED APPLICATION

This application is based upon and claims the benefit of priority from Japanese Patent Applications No. 2009-022902 filed on Feb. 3, 2009 and No. 2009-078992 filed on Mar. 27, 2009, in the Japan Patent Office, of which the contents are incorporated herein by reference.

BACKGROUND OF THE INVENTION

1. Field of the Invention

The present invention relates to a medical manipulator for use in laparoscopic surgery, for example.

2. Description of the Related Art

According to a laparoscopic surgical operation process, a certain number of small holes are opened in the abdominal region, for example, of a patient, and a flexible scope and manipulators or forceps are inserted into the holes. The surgeon performs a surgical operation on the patient with the manipulators or forceps while watching an image captured by the flexible scope and displayed on a display monitor. Since the laparoscopic surgical operation process does not require a laparotomy, the surgical operation is less burdensome on the patient and greatly reduces the number of days required for the patient to spend before recovering from the operation and being released from the hospital. Therefore, the laparoscopic surgical operation process is expected to find and increased range of surgical operations to which it is applicable.

Manipulators for laparoscopic surgical operations are required to allow the operator, i.e., a surgeon, to perform various appropriate techniques quickly depending on the position and size of the affected part, for removing, suturing, and ligating (tying-knot) the affected part. Japanese Laid-Open Patent Publication No. 2002-102248, Japanese Laid-Open Patent Publication No. 2004-301275, and U.S. Pat. No. 6,889,116, for example, disclose manipulators that can be operated simply with a high degree of freedom.

Such manipulators employ a wire and pulley mechanism as a power transmitting mechanism, since a wire and pulley mechanism is simple in structure and exhibits high power transmitting efficiency.

When a surgeon uses forceps of a general nature in a laparoscopic surgery or in surgery using a flexible scope, external forces applied to the distal-end working unit of the forceps and gripping forces applied by the distal-end working unit are transmitted, not directly but as reactive forces, to the hand of the surgeon. Therefore, the surgeon is capable of feeling the forces to a certain extent and can operate the forceps based on such reactive forces. Forceps that have been available heretofore have only a few degrees of freedom, e.g., one degree of freedom, and are difficult to handle because they are movable only in limited directions for gripping and cutting tissues or for inserting suture needles, and require surgeon to be highly skilled when using them.

To achieve higher degrees of freedom, one option would be to use a master-slave remote control surgical robot, for example. Such a master-slave remote control surgical robot is advantageous in that it enables a high degree of freedom, can approach the affected part of a patient from various desired directions, and can be operated effectively and efficiently. However, external forces applied to the distal-end working unit, as well as gripping forces applied by the distal-end working unit, are not transmitted to the master side of the master-slave remote control surgical robot.

If a sensation of force is to be available on the master side of the master-slave remote control surgical robot, then the surgical robot system must be expensive and complex, as the system requires a highly sophisticated bilateral control architecture based on a highly sensitive force sensing system and a computer system having high-speed sampling times. In addition, in practice, bilateral control architecture has not yet reached a sufficient performance level at present.

The applicants have already proposed multiple-degree-of-freedom forceps, including a distal-end working unit having joints that can be actuated by motors based on commands from an operating unit. Since the operating unit, i.e., an operating handle, and the distal-end working unit, i.e., distal-end joints, are integrally coupled to each other, external forces applied to the distal-end working unit and gripping forces applied by the distal-end working unit are transmitted, not directly but via the multiple-degree-of-freedom forceps, to the operating unit. Therefore, an operator of the multiple-degree-of-freedom forceps can feel such forces to a certain extent. Nevertheless, there is a demand for a multiple-degree-of-freedom forceps, which can allow the operator to feel stronger external forces and gripping forces. In particular, there is a demand for a multiple-degree-of-freedom forceps, which allows the operator to feel stronger gripping forces.

As with the manipulators disclosed in Japanese Laid-Open Patent Publication No. 2002-102248 and Japanese Laid-Open Patent Publication No. 2004-301275, a wire and pulley mechanism may be applied to such a multiple-degree-of-freedom forceps, which allows the operator to feel gripping forces.

However, the distal-end working unit of a manipulator is required to be quite small in size, because the distal-end working unit is inserted into abdominal cavities and used within small regions. If the wire and pulley mechanism incorporated in the distal-end working unit of the manipulator is reduced in size in order to reduce the size of the distal-end working unit thereof, then the operating angle of the distal-end working unit possibly may be reduced due to such dimensional limitations.

The wire and pulley mechanism incorporated in the distal-end working unit of the manipulator is expected to experience increased wire loads, owing to a large amount of wire wear and bending, since the pulleys thereof have considerably small diameters and are spaced a small distance from each other.

SUMMARY OF THE INVENTION

It is an object of the present invention to provide a medical manipulator, which includes a distal-end working unit that is small in size and has a wide operating angle.

Another object of the present invention is to provide a medical manipulator, which minimizes loads on the wires of a power transmitting mechanism incorporated therein as much as possible.

According to the present invention, there is provided a medical manipulator for actuating an end effector on a distal end thereof in response to movement of a drive member, comprising a transmitting member for transmitting a drive force to the end effector, a main shaft, the transmitting member being movably supported on the main shaft, an arcuate driven member integrally mounted on the transmitting member near a proximal end thereof, the arcuate driven member having an arcuate convex surface that is convex toward the proximal end and a cavity that is non-convex toward a distal end of the transmitting member, the cavity being disposed within a virtual circle a portion of which is represented by the arcuate convex surface, a cylindrical return member fixedly mounted on the main shaft between the arcuate driven member and the distal end of the transmitting member, and an annular flexible member having a portion connected to the drive member and trained at least one turn around and extending between the arcuate convex surface and the cylindrical return member, wherein when the drive member is moved toward a proximal end of the manipulator in order to pull the annular flexible member, the arcuate driven member is moved together with the transmitting member toward the distal end of the manipulator, and the cylindrical return member includes a proximal-end portion that enters the cavity.

Since the proximal-end portion of the cylindrical return member enters the cavity, the transmitting member can move an increased maximum distance, thereby allowing a distal-end working unit of the medical manipulator to operate over a wide operating angle. Furthermore, since the distance from the distal end of the cylindrical return member to the proximal end of the transmitting member at a time when the transmitting member is fully moved to the proximal end is reduced, the transmitting member can be reduced in size, and hence the medical manipulator as a whole can be reduced in size. Moreover, since the arcuate driven member is integral with the transmitting member, the number of components that make up the medical manipulator is reduced. The term "arcuate" as used herein should not be interpreted in a strict sense, but may cover a crescent shape, a semicircular shape, a sectorial shape, or the like. Likewise, the term "arcuate" of the arcuate convex surface should not be interpreted in a strict sense, but may cover an elliptical arcuate shape, etc. With the medical manipulator according to the present invention, since the maximum distance that the transmitting member moves remains unchanged, the wide operating angle of the distal-end working unit is maintained, and when the transmitting member is fully moved toward the proximal end, the distance from the distal end of the cylindrical return member to the proximal end of the transmitting member is reduced. Therefore, the distal-end working unit, and more particularly the transmitting member thereof, can be reduced in size, and hence the medical manipulator as a whole can be reduced in size.

The cavity may be defined by an arcuate concave surface, which opens toward the distal end of the transmitting member. This arrangement makes the transmitting member smaller in size, thereby making the medical manipulator smaller in size. The term "arcuate" for defining the arcuate concave surface should not be interpreted in a strict sense, but may cover an elliptical arcuate shape, etc.

When the drive member is moved toward the proximal end of the manipulator in order to pull the annular flexible member, the arcuate driven member is moved together with the transmitting member toward the distal end of the manipulator, and the proximal-end portion of the cylindrical return member enters the cavity defined by the arcuate concave surface beyond a chord line that interconnects opposite concave ends of the arcuate concave surface. This arrangement makes the transmitting member smaller in size, thereby making the medical manipulator smaller in size as a whole. The term "arcuate" for defining the arcuate concave surface should not be interpreted in a strict sense, but may cover an elliptical arcuate shape, etc.

The medical manipulator may further comprise a second end effector drive mechanism including the drive member, the end effector, the arcuate driven member, the cylindrical return member, the flexible member, a cylindrical idle member disposed more closely to the proximal end of the medical manipulator than the transmitting member, and a cylindrical guide member disposed between the cylindrical idle member and the transmitting member, a cylindrical driven member mounted on the transmitting member near the proximal end thereof, a first end effector drive mechanism including a drive member, a flexible member, a cylindrical idle member, the cylindrical driven member, and a cylindrical guide member, and a drive member moving mechanism for moving the drive member of the first end effector drive mechanism and the drive member of the second end effector drive mechanism in opposite directions. With this arrangement, the end effector may be operated in one direction directly by the first end effector drive mechanism, and in an opposite direction directly by the second end effector drive mechanism.

The arcuate concave surface may be represented by an arc having a radius of curvature which is equal to the radius of the cylindrical return member as viewed in plan. With this arrangement, the flexible member is prevented from making sharp bends, and hence loads thereon are reduced.

The arcuate convex surface may be represented by an arc having a central angle ranging from 140° to 220° as viewed in plan. With this arrangement, the flexible member is prevented from making sharp bends, and hence loads thereon are reduced.

The main shaft may support the drive members, the arcuate driven member, and the cylindrical return member thereon, wherein the medical manipulator further includes a pin supported on the main shaft, the pin being of a cantilevered structure, the cylindrical return member being rotatably supported on the pin. With this arrangement, the transmitting member can be reduced in size, thereby making the medical manipulator smaller in size, while at the same time the operating angle of the distal-end working unit can be maintained.

The cylindrical idle member may comprise a cylinder having a diameter greater than the diameter of the cylindrical guide member. The gap between the cylindrical idle member and the cylindrical guide member thus can be reduced in order to increase the operating range of the distal-end working unit about a yaw axis.

The medical manipulator may further comprise a manually operable input unit, the drive member being mechanically connected to the manually operable input unit. The medical manipulator is thus able to produce strong gripping forces, and forces applied to the distal-end working unit can be transmitted to the operator of the medical manipulator.

According to the present invention, there is also provided a medical manipulator comprising an end effector drive mechanism, which includes a drive member disposed in a distal end portion of the end effector drive mechanism, the drive member being movable in opposite directions, an annular flexible member having a portion connected to the drive member, a cylindrical idle member disposed more closely to a distal end of the end effector drive mechanism than the drive member, a cylindrical driven member disposed more closely to the distal end of the end effector drive mechanism than the cylindrical idle member, a cylindrical guide member disposed between the cylindrical idle member and the cylindrical driven member, and an end effector connected to the cylindrical driven member. The annular flexible member extends on opposite sides of the cylindrical idle member, crosses between the cylindrical guide member and the cylindrical driven member, extends on opposite sides of the cylindrical guide member in an axially shifted position, and is trained around the cylindrical driven member, and wherein, assuming a direction from the cylindrical guide member toward the cylindrical driven member is referred to as a Z direction, the cylindrical guide member and the cylindrical driven member have respective axes extending out of parallelism with each other as viewed from the Z direction, such that the annular flexible member has outward and inward stretched sections that extend in the Z direction between the cylindrical guide member and the cylindrical driven member.

The flexible member passes straight on the side surface of the cylindrical driven member and the side surface of the cylindrical guide member, thereby reducing friction between the flexible member, the cylindrical driven member and the cylindrical guide member.

The cylindrical driven member may have a cylindrical driven member groove formed in a side surface thereof for circumferentially guiding the annular flexible member. The cylindrical driven member groove is effective to reduce friction, which is caused when the flexible member slides laterally along the side surface of the cylindrical driven member.

The cylindrical guide member may comprise a first layer guide pulley for guiding either one of an outward stretched section and an inward stretched section of the annular flexible member, and a second layer guide pulley for guiding the other of the stretched sections of the annular flexible member at a position which is axially displaced a distance Δ from the stretched section of the annular flexible member that is guided by the first layer guide pulley, and the annular flexible member has a turn trained around the cylindrical driven member and having opposite ends which are displaced from each other by the distance Δ in an axial direction of the cylindrical guide member. The flexible member therefore is allowed to move along an appropriate path. The first layer guide pulley and the second layer guide pulley allow the outward and inward stretched sections of the flexible member to move respectively in opposite directions.

The cylindrical idle member may comprise a first layer idle pulley and a second layer idle pulley, which are held in coaxial alignment with each other and disposed parallel to each other. The first layer idle pulley and the second layer idle pulley allow the driven wire to move respectively in opposite directions.

The annular flexible member may comprise a single wire having opposite ends secured to each other at a position other than a junction where the annular flexible member is connected to the drive member. Since the flexible member is annular, loads applied thereto are divided into substantially equal load components on the two stretched sections of the flexible member. Therefore, the flexible member may be thin and sufficiently flexible.

The medical manipulator may further comprise a manually operable input unit, wherein the drive member is connected mechanically to the manually operable input unit. The drive member, which is a mechanical component such as a nonelastic solid member, is effective in reducing unavoidable expansion and contraction under tension, as much as possible.

The end effector drive mechanism may serve as a first end effector drive mechanism, and the medical manipulator may further comprise a second end effector drive mechanism including a drive member, an annular flexible member, a cylindrical idle member, a cylindrical driven member, and a cylindrical guide member, a drive member moving mechanism for moving the drive member of the first end effector drive mechanism and the drive member of the second end effector drive mechanism in opposite directions, and a cylindrical return member disposed more closely to a distal end of the second end effector drive mechanism than the cylindrical driven member, wherein the annular flexible member is trained around and extends between the cylindrical driven member and the cylindrical return member of the second end effector drive mechanism, the cylindrical idle member and the cylindrical driven member having respective axes extending parallel to each other. With this arrangement, the end effector may be operated in one direction directly by the first end effector drive mechanism, and in an opposite direction directly by the second end effector drive mechanism.

The first end effector drive mechanism may include a rod for actuating the end effector, the cylindrical driven member of the first end effector drive mechanism may comprise a pulley rotatably supported on the rod, and the cylindrical driven member of the second end effector drive mechanism may be integral with the rod. Since the driven wire does not move relatively to the cylindrical driven member of the second end effector drive mechanism, the cylindrical driven member can be combined integrally with the rod.

The end effector may comprise an openable and closable gripper. The annular flexible member of the first end effector drive mechanism may be held under higher tension when the gripper is closed, and the annular flexible member of the second end effector drive mechanism may be held under higher tension when the gripper is opened.

The flexible member, which is trained around the second end effector drive mechanism, is rarely moved under high tension, i.e., is rarely moved in a high frictional state. Consequently, it is preferable for the cylindrical driven member to be combined integrally with the rod.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 12A is a view showing the positional relationship between a transmitting member, a crescent driven member, and a return pulley with the gripper being closed;

FIG. 12B is a view showing the positional relationship between the transmitting member, the crescent driven member, and the return pulley with the gripper being opened to a maximum;

DESCRIPTION OF THE PREFERRED EMBODIMENTS

Medical manipulators according to embodiments of the present invention will be described below with reference to FIGS. 1 to 35.

Figure 1:
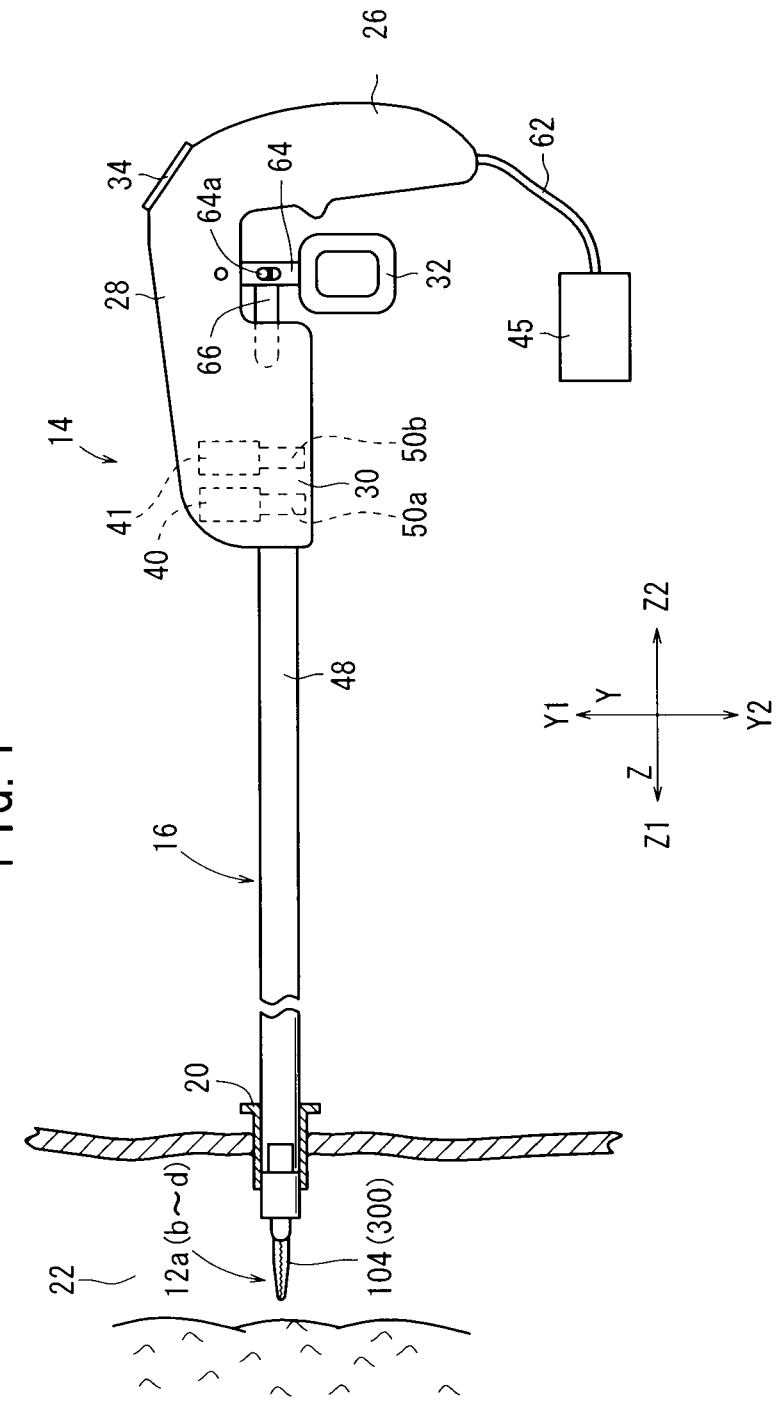
FIG. 1 is a side elevational view of a medical manipulator according to an embodiment of the present invention.

As shown in FIG. 1, a medical manipulator 10 according to a first embodiment of the present invention serves as part of a medical manipulator system, and is electrically connected to a controller 45.

The controller 45, which electrically controls the medical manipulator 10, is connected by a connector to a cable 62, which extends from the lower end of a grip handle 26 of the medical manipulator 10. The controller 45 is capable of independently controlling a plurality of medical manipulators 10 at the same time, although the controller 45 also can control a single medical manipulator 10, as shown in FIG. 1.

The medical manipulator 10 includes a distal-end working unit 12a for gripping a portion of a living tissue, a curved needle, or the like, for performing a predetermined surgical treatment. The distal-end working unit 12a typically is referred to as a gripping forceps or a needle driver (needle holder).

Figure 2:
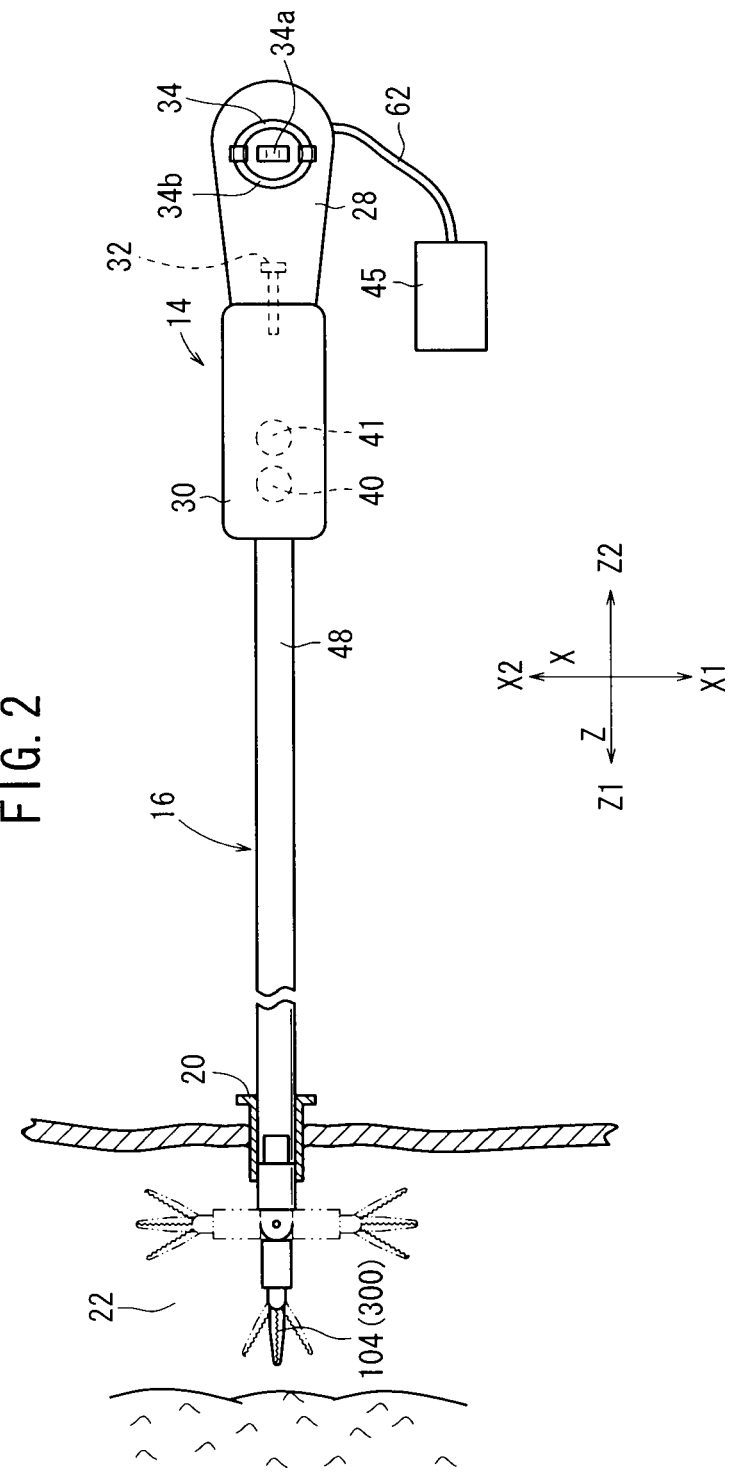
FIG. 2 is a plan view of the medical manipulator shown in FIG. 1.

As shown in FIGS. 1 and 2, the medical manipulator 10 includes an operating unit 14 which is gripped and operated by a user's hand, and a working unit 16 fixed to the operating unit 14. The operating unit 14 and the working unit 16 are integrally connected to each other. However, the operating unit 14 and the working unit 16 may also be connected to each other in a detachable manner.

In the description that follows, it is assumed that the transverse directions in FIGS. 1 and 2 are referred to as X directions, vertical directions as Y directions, and longitudinal directions of a joint shaft 48 as Z directions. Among the X directions, the rightward direction as viewed from the distal end is referred to as an X1 direction, and the leftward direction as an X2 direction. Among the Y directions, the upward direction is referred to as a Y1 direction, and the downward direction as a Y2 direction. Among the Z directions, the forward direction is referred to as a Z1 direction, and the rearward direction as a Z2 direction. Unless otherwise noted, these directions represent directions of the medical manipulator 10 when the medical manipulator 10 is in a neutral attitude. The definitions of the above directions are for illustrative purposes only. The medical manipulator 10 can be used in any of various orientations, e.g., it may be used upside down.

The working unit 16 includes the distal-end working unit 12a for performing a working process on a patient, and the elongate hollow joint shaft 48, which connects the distal-end working unit 12a and the operating unit 14 to each other. The distal-end working unit 12a and the joint shaft 48 have small diameters and can be inserted into a body cavity 22 through a trocar 20, in the form of a hollow cylinder mounted in an abdominal region or the like of the patient. The distal-end working unit 12a is actuated by a composite input unit 34 of the operating unit 14 in order to perform various techniques to remove, grip, suture, or ligate (tie-knot) an affected part of the patient's body within the body cavity 22.

The operating unit 14 includes a grip handle 26 which is gripped by a hand, a bridge 28 that extends from an upper portion of the grip handle 26, an actuator block 30 connected to a distal end of the bridge 28, and a trigger lever (input unit) 32 operatively coupled to the bridge 28.

As shown in FIG. 1, the grip handle 26 extends from an end of the bridge 28 in the Y2 direction and has a length suitable for being gripped by the hand. The grip handle 26 includes the composite input unit 34 mounted on an upper slanted surface thereof.

The cable 62 connected to the controller 45 is disposed on the lower end of the grip handle 26 and is integrally connected to the grip handle 26. The grip handle 26 and the cable 62 may be connected to each other by a connector.

The composite input unit 34 comprises a composite input means for imparting rotational commands in rolling directions (shaft rotating directions) and yawing directions (left and right directions) to the distal-end working unit 12a. For example, commands in the yawing directions are given by a first input means 34a, which operates in lateral directions, whereas commands in the rolling directions are given by a second input means 34b, which operates in the shaft rotating directions. The trigger lever 32 serves as an input means for imparting opening and closing commands to an end effector 104 (see FIG. 1) of the distal-end working unit 12a. Although the end effector 104 is available in various forms, the medical manipulator 10 employs an openable and closable gripper as the end effector 104.

The composite input unit 34 includes an input sensor for detecting an operational quantity, and supplies a detected operation signal (e.g., an analog signal) indicative of the detected operational quantity to the controller 45.

The trigger lever 32 comprises a lever disposed beneath the bridge 28 in the Y2 direction, and the trigger lever 32 is disposed at a location where it can easily be operated by the index finger. The trigger lever 32 is connected to the actuator block 30 by a first link 64 and a second link 66, and is movable toward and away from the grip handle 26. The first link 64 is swingably pivoted on a portion of the bridge 28, and the trigger lever 32 is mounted on the lower end of the first link 64. The second link 66 projects in the Z2 direction from the actuator block 30 and engages in an oblong hole 64a, which is formed in the first link 64. When the trigger lever 32 is moved, the second link 66 is movable back and forth in longitudinal directions along the oblong hole 64a.

Manual operations applied to the trigger lever 32 are mechanically transmitted in order to open and close the end effector 104. The first link 64, the second link 66, a first end effector drive mechanism 260a and a second end effector drive mechanism 260b, to be described later, which serve as means for mechanically transmitting manual actions between the trigger lever 32 and the end effector 104, collectively make up an operation transmitting unit.

The term "mechanically" refers to a system for transmitting manual operations via a wire, a chain, a timing belt, a link, a rod, a gear, or the like, which is actuated primarily by a mechanical component in the form of a solid body, which is non-elastic in the power transmitting direction. Although a wire, a chain, or the like inevitably is subject to being slightly elongated under tension, it still may be regarded as a mechanical component in the form of a non-elastic solid body.

As shown in FIG. 1, the actuator block 30 houses therein motors (attitude axis actuators) 40 and 41, which correspond to respective mechanisms providing two out of three degrees of freedom, which are incorporated in the distal-end working unit 12a. The motors 40, 41 are arrayed parallel to each other in the longitudinal direction of the joint shaft 48. The motors 40, 41 correspond to movements in rolling and yawing directions of the distal-end working unit 12a. The motors 40, 41 are small in size and diameter, thereby enabling the actuator block 30 to be compact and flat in shape. The motors 40, 41 can be energized to rotate drive shafts under the control of the controller 45, based on operations of the operating unit 14.

The motors 40, 41 are combined with angle sensors, not shown, for detecting rotational angles of the drive shafts, and for supplying detected angle signals to the controller 45. The angle sensors may comprise rotary encoders, for example.

The actuator block 30 houses therein pulleys 50a, 50b connected to respective drive shafts of the motors 40, 41.

Figure 3:
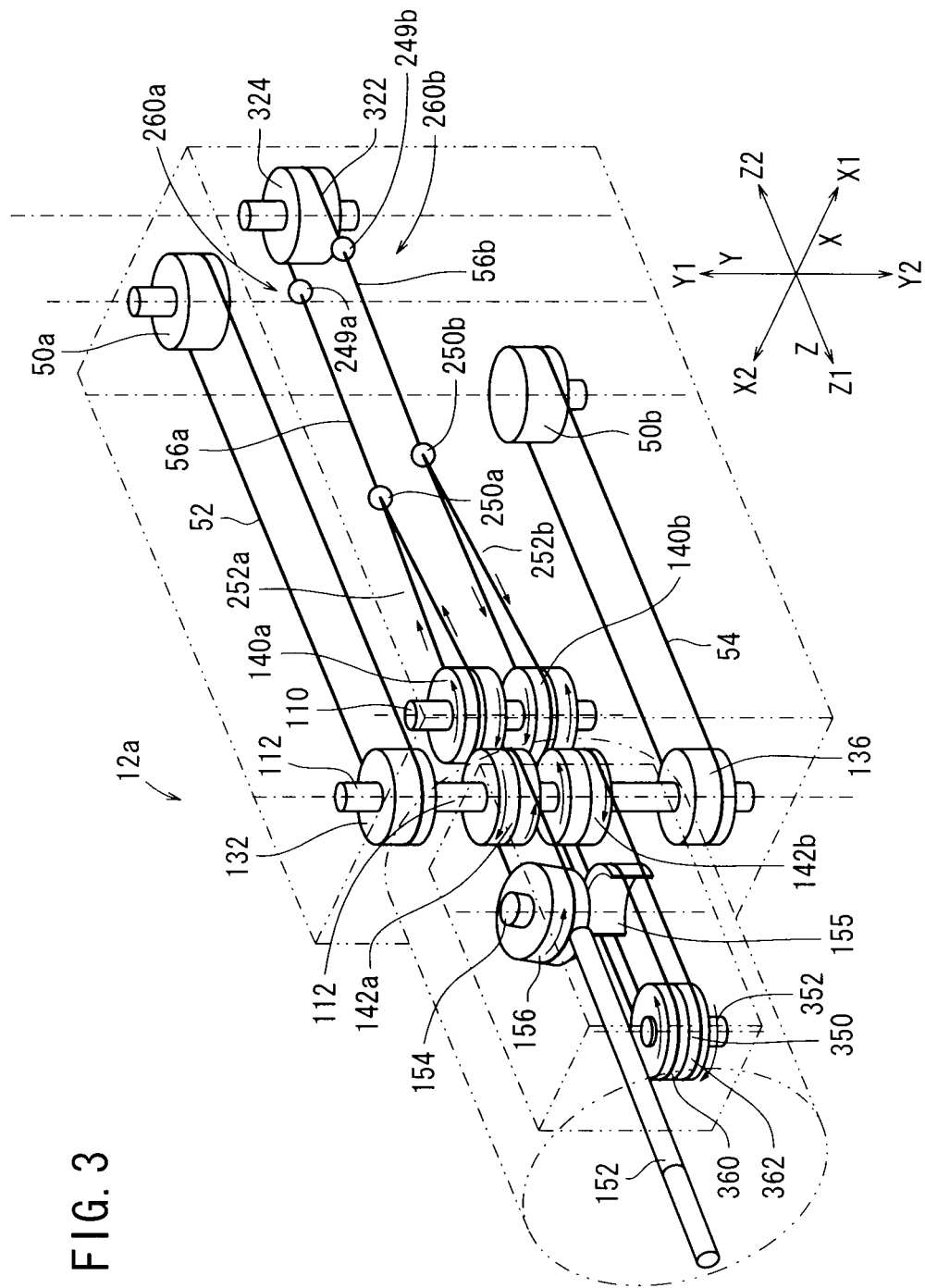
FIG. 3 is a schematic perspective view of the distal-end working unit of the medical manipulator.

As shown in FIG. 3, wires 52, 54 are wound respectively around the pulleys 50a, 50b, and extend through a hollow region 48a (see FIG. 7) in the joint shaft 48 toward the distal-end working unit 12a. The wires 52, 54 may be of the same type and same diameter.

The composite input unit 34 and the trigger lever 32 of the operating unit 14 are not limited to the positions, forms, and operating methods which are illustrated and described above. For example, the composite input unit 34 may be replaced by operating rollers, buttons, or a joystick. Positions and methods that allow the medical manipulator to be easily operated may be selected and designed.

Structural details of the distal-end working unit 12a will be described below. A first end effector drive mechanism 260a and a second end effector drive mechanism 260b, which constitute basic mechanisms for opening and closing the end effector 104 of the distal-end working unit 12a, will be described below.

Figure 4:
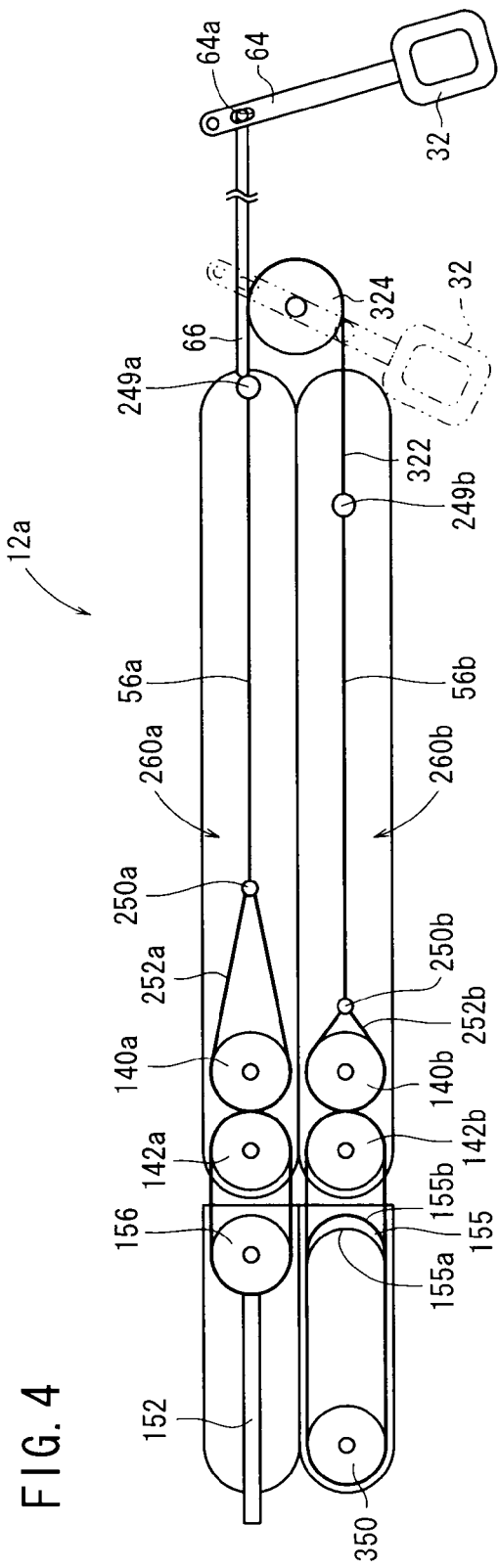
FIG. 4 is a schematic plan view of the distal-end working unit.

As shown in FIG. 4, the distal-end working unit 12a includes the first and second end effector drive mechanisms 260a, 260b. The first end effector drive mechanism 260a includes a transmitting member 152, a wire (drive member) 56a, a driven wire 252a, an idle pulley (idle cylindrical member) 140a, a guide pulley (cylindrical guide member) 142a, and a driven pulley (cylindrical driven member) 156. The second end effector drive mechanism 260b includes similar components, which will be described later.

The components of the first end effector drive mechanism 260a are denoted by reference numerals having a suffix "a", whereas the components of the second end effector drive mechanism 260b are denoted by reference numerals having a suffix "b". Since certain components of the first end effector drive mechanism 260a and corresponding components of the second end effector drive mechanism 260b operate identically, only those components of the first end effector drive mechanism 260a, which are otherwise identical to those of the second end effector drive mechanism 260b, will be described below.

In FIG. 4, the first end effector drive mechanism 260a and the second end effector drive mechanism 260b are shown as being juxtaposed in plan. In the actual medical manipulator 10, however, as shown in FIG. 3, the first end effector drive mechanism 260a and the second end effector drive mechanism 260b are juxtaposed in axial directions of the pulleys, i.e., in the Y directions.

As shown in FIG. 4, one end of a wire 56a is connected to both ends of the driven wire (flexible member) 252a by a terminal 250a. The driven wire 252a is in the form of a ring-like flexible member having a portion thereof connected to the wire 56a. The driven wire 252a may alternatively comprise a rope, a resin wire, piano wire, a chain, or the like. The term "ring-shaped" should be interpreted in a broad sense. The flexible member does not necessarily need to be flexible over its entire length. At least a portion of the driven wire 252a, which is trained around each of the pulleys, may be a flexible member, with a linear portion being connected by a rigid member. The driven wire 252a may comprise part of the wire 56a.

Figure 5:
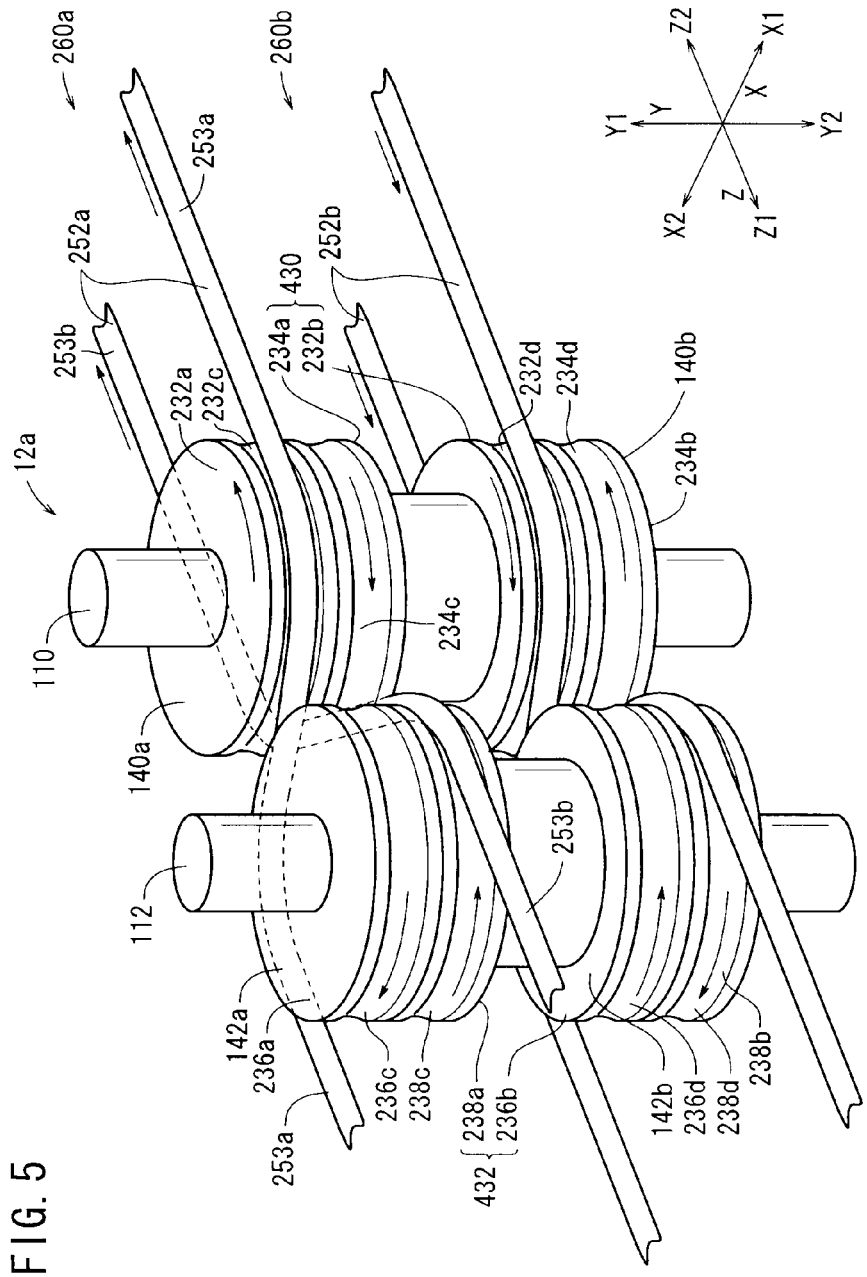
FIG. 5 is an enlarged perspective view of an idle pulley and a guide pulley of the distal-end working unit.

As shown in FIG. 5, in the distal-end working unit 12a, the idle pulleys 140a, 140b comprise respective first layer idle pulleys (first layer idle cylindrical members) 232a, 232b, which are displaced in the Y1 direction in coaxial alignment with each other, and respective second layer idle pulleys (second layer idle cylindrical members) 234a, 234b, which are displaced in the Y2 direction in coaxial alignment with each other.

The guide pulleys 142a, 142b comprise respective first layer guide pulleys (first layer cylindrical guide members) 236a, 236b, which are displaced in the Y1 direction in coaxial alignment with each other, and respective second layer guide pulleys (second layer cylindrical guide members) 238a, 238b, which are displaced in the Y2 direction in coaxial alignment with each other. Such a structure allows the paired pulleys to rotate smoothly in opposite directions. The terms used for the pulleys are merely for distinguishing the respective pulleys for illustrative purposes. The idle pulley 140a and the guide pulley 142a have grooves formed in side surfaces thereof in which the driven wire 252a is trained. The groove of the first layer idle pulley 232a is referred to as a first layer idle pulley groove 232c, whereas the groove of the first layer idle pulley 232b is referred to as a first layer idle pulley groove 232d. The other grooves are referred to similarly.

At one end in the Z2 direction in FIG. 6, one stretched section of the driven wire 252a (hereinafter referred to as an outward stretched section 253a for distinguishing purposes) is in contact with surfaces of the first layer idle pulley 232a in the X1 and Z1 directions, is in contact with surfaces of the first layer guide pulley 236a in the Z2 and X2 directions, proceeds to the surface of the driven pulley 156 that faces in the X2 direction, and then is trained one half-turn around the surface of the driven pulley 156 in the Z1 direction, and proceeds to the surface thereof that faces in the X1 direction.

At the end in the Z2 direction in FIG. 6, the other stretched section of the driven wire 252a (hereinafter referred to as an inward stretched section 253b for distinguishing purposes) is in contact with surfaces of the second layer idle pulley 234a in the X2 and Z1 directions, is in contact with surfaces of the second layer guide pulley 238a in the Z2 and X1 directions, and proceeds to the surface of the driven pulley 156 that faces in the X1 direction.

The driven wire 252a thus passes through a circulatory path having starting and ending points at the terminal 250a, which is positioned more closely to the proximal end than the idle pulley 140a. The driven wire 252a crosses over itself between the idle pulley 140a and the guide pulley 142a, thereby making up a substantially figure-8 configuration. The terminal 250a and the driven wire 252a are mechanically connected to the trigger lever 32 by the wire 56a.

The term "mechanically" refers to a system for actuating members via a mechanical component in the form of a solid body, which is non-elastic in the power transmitting direction. The wire 56 is a flexible member. For closing the end effector 104, the wire 56 is pulled in the Z2 direction by the trigger lever 32, and is essentially non-elastically deformed, or is elastically deformed only to an extent which is trouble-free in operation, thereby providing a mechanical connecting means.

The driven wire 252a crosses over itself between the idle pulley 140a and the guide pulley 142a, as viewed in plan, and is displaced in the Y directions. Since the guide pulley 142a is made up of the first layer guide pulley 236a and the second layer guide pulley 236b, the outward stretched section 253a and the inward stretched section 253b are necessarily displaced from each other in the Y directions.

As shown in FIG. 5, the outward stretched section 253a is displaced from the inward stretched section 253b in the Y1 direction by a distance Δ, which is slightly greater than the diameter of the driven wire 252a. On the guide pulley 142a, the outward stretched section 253a extends from a position that is displaced from the inward stretched section 253b in the Y1 direction by the distance Δ toward the driven pulley 156 (see FIG. 11), which is spaced in the Z directions.

When the wire 56a (see FIG. 3) is pulled in the Z2 direction, the first layer idle pulley 232a and the second layer guide pulley 238a are rotated counterclockwise as viewed in plan, whereas the second layer idle pulley 234a and the first layer guide pulley 236a are rotated clockwise as viewed in plan. Since each of the idle pulley 140a and the guide pulley 142a comprises two parallel coaxial pulleys, they are rotatable in the opposite directions when the driven wire 252a, which is held thereagainst, is moved, and hence the idle pulley 140a and the guide pulley 142a operate smoothly.

The second end effector drive mechanism 260b comprises a driven wire 252b, an idle pulley 140b, a guide pulley 142b, and a crescent driven member (integral driven member) 155, which correspond respectively to the driven wire 252a, the idle pulley 140a, the guide pulley 142a, and the driven pulley 156 of the first end effector drive mechanism 260a. The second end effector drive mechanism 260b also includes a return pulley (cylindrical return member) 350. The return pulley 350 is spaced from the crescent driven member 155 in the Z1 direction. The crescent driven member 155 has a reference axis that extends in the Y directions. The driven pulley 156 is mounted on the transmitting member 152 obliquely to the Y directions, and is movable in the Z directions together with the transmitting member 152. The return pulley 350 is movable in the Z directions relative to the transmitting member 152. Structural details of the return pulley 350, the crescent driven member 155, the driven pulley 156, and the transmitting member 152 will be described later, with reference to FIGS. 11, 12A, 12B, 15A and 15B.

Figure 6:
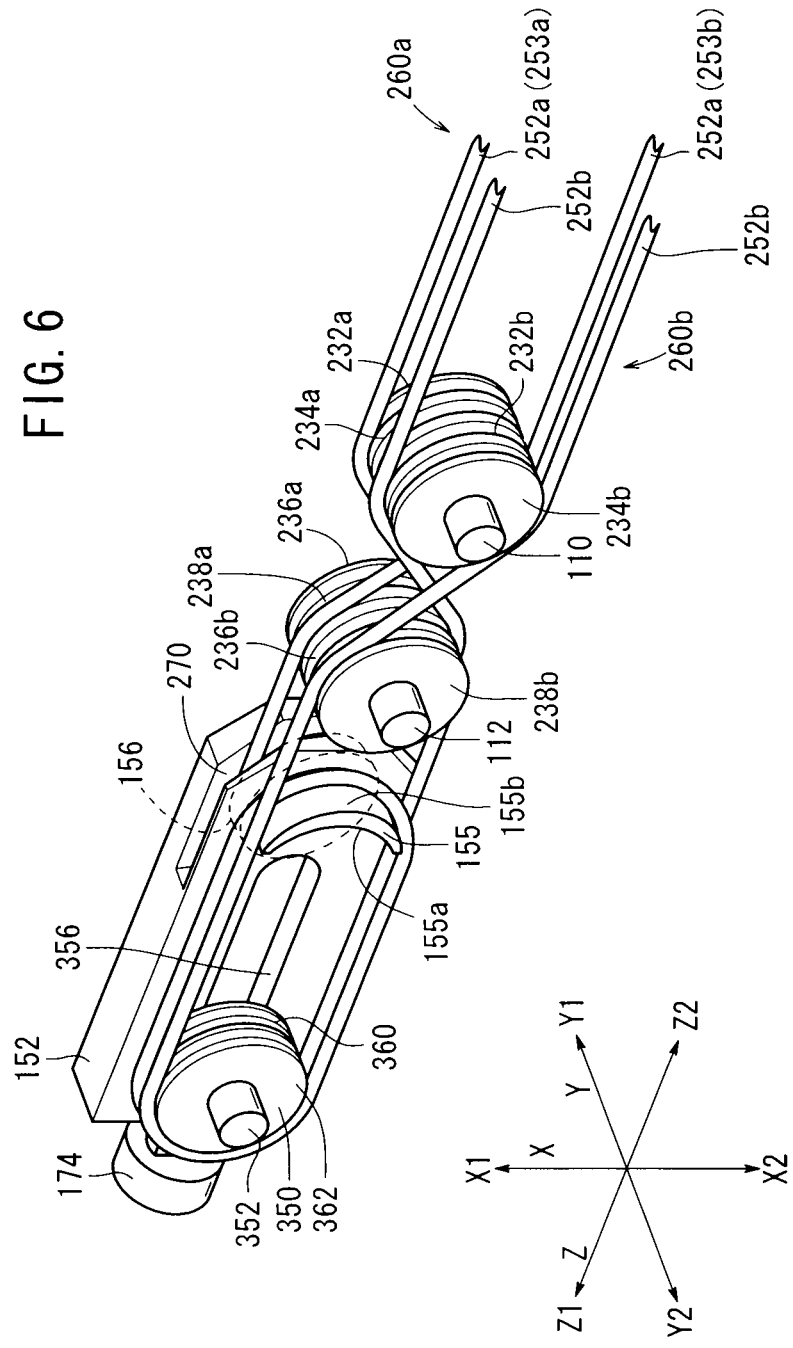
FIG. 6 is an enlarged perspective view of a first end effector drive mechanism and a second end effector drive mechanism of the distal-end working unit.

As shown in FIG. 6, the return pulley 350 comprises a first layer return pulley (first layer return cylindrical member) 360, which is displaced in the Y1 direction, and a second layer return pulley (second layer return cylindrical member) 362, which is displaced in the Y2 direction. The first and second layer return pulleys 360, 362 are aligned coaxially with each other. The first layer return pulley 360 and the second layer return pulley 362 may include a first layer return pulley groove 360c and a second layer return pulley groove 362c, respectively, formed in side surfaces thereof, similar to the first layer idle pulley 232a, etc.

At one end in the Z2 direction in FIG. 6, one of the stretched sections of the driven wire 252b is in contact with surfaces of the first layer idle pulley 232b in the X1 and Z1 directions, respectively, then is in contact with surfaces of the first layer guide pulley 236b in the Z2 and X2 directions, respectively, and proceeds to the surface of the crescent driven member 155 that faces in the X2 direction. The driven wire 252b extends in the Z1 direction to the surface of the first layer return pulley 360 that faces in the X2 direction, then is trained one half-turn around the surface of the first layer return pulley 360 in the Z1 direction, and returns in the Z2 direction. The driven wire 252b extends in the Z2 direction to the surface of the crescent driven member 155 that faces in the X1 direction, is trained around the surface of the crescent driven member 155 that faces in the Z2 direction while extending obliquely in the Y2 direction, returns in the Z1 direction, and finally reaches the surface of the second layer return pulley 362 that faces in the X2 direction.

At the end in the Z2 direction, as shown in FIG. 6, the other stretched section of the driven wire 252b is in contact with surfaces of the second layer idle pulley 234b in the X2 and Z1 directions, then is in contact with surfaces of the second layer guide pulley 238b in the Z2 and X1 directions, and proceeds to the surface of the crescent driven member 155 that faces in the X1 direction. The driven wire 252b extends in the Z1 direction to the surface of the second layer return pulley 362 that faces in the X1 direction, then is trained one half-turn around the surface of the second layer return pulley 362 in the Z1 direction, and finally reaches the surface of the second layer return pulley 362 that faces in the X2 direction. As with the driven wire 252a, the driven wire 252b passes through a circulatory path, having starting and ending points at the terminal 250b, and the driven wire 252b is mechanically connected to the trigger lever 32 by the wire 56b.

As shown in FIGS. 3 and 4, the second link 66 is connected to an end of the wire 56a, and to an end of a drive joint wire (drive joint flexible member) 322, by means of a terminal 249a (welding, through hole, etc.).

The drive joint wire 322 is trained around a drive joint pulley (rotation operator) 324 and has one end connected to the ends of the wire 56a and to the second link 66 by the terminal 249a, as described above, and another end connected to an end of the wire 56b by a terminal 249b. As indicated by the imaginary lines shown in FIG. 4, the trigger lever 32 may be used as a drive member moving mechanism, instead of the drive joint pulley 324.

With the above arrangement, the wire 56a and the wire 56b can easily be moved in opposite directions. When the trigger lever 32 is pulled, the terminal 249a also is pulled in unison therewith, thereby moving the transmitting member 152 in the Z2 direction. When the trigger lever 32 is pushed, the terminal 249b is pushed in unison therewith. Since the return pulley 350 is fixed in position, the crescent driven member 155 and the transmitting member 152 are moved in the Z1 direction.

The terminal 250a is disposed in a position appropriately spaced from the idle pulley 140a, so that the driven wire 252a will not be bent excessively. Both ends of the driven wire 252a form an acute angle at the terminal 250a. The idle pulley 140a and the guide pulley 142a are spaced from each other by a small gap, which is substantially the same as the width of the driven wire 252a, for example. The end effector 104 is opened and closed when the transmitting member 152 is moved back and forth.

As shown in FIG. 5, the second layer idle pulley 234a and the first layer idle pulley 232b, which constitute two inner pulleys, may be combined integrally into a central common idle pulley 430. The second layer guide pulley 238a and the first layer guide pulley 236b, which constitute two inner guide pulleys, may be combined integrally into a central common guide pulley 432.

More specifically, since the terminal 250a and the terminal 250b (see FIG. 4) move the same distance in opposite directions, the pulleys and the stretched sections of the wire move in directions indicated by the arrows in FIG. 5. The second layer idle pulley 234a and the first layer idle pulley 232b are rotated through the same angle and in the same direction (clockwise in FIG. 5), whereas the second layer guide pulley 238a and the first layer guide pulley 236b also are rotated through the same angle and in the same direction (counterclockwise in FIG. 5). Therefore, these members do not need to be formed separately, but rather, the members may be combined into a central common idle pulley 430 and a central common guide pulley 432, thus resulting in a simpler structure. Although to facilitate understanding, the distance between the second layer guide pulley 238a and the first layer guide pulley 236a, as well as the distance between the second layer guide pulley 238a and the first layer guide pulley 236b, are shown in FIG. 5 as being relatively large, in practice these distances may essentially be nil.

Overall structural details of the distal-end working unit 12a will be described below.

Figure 7:
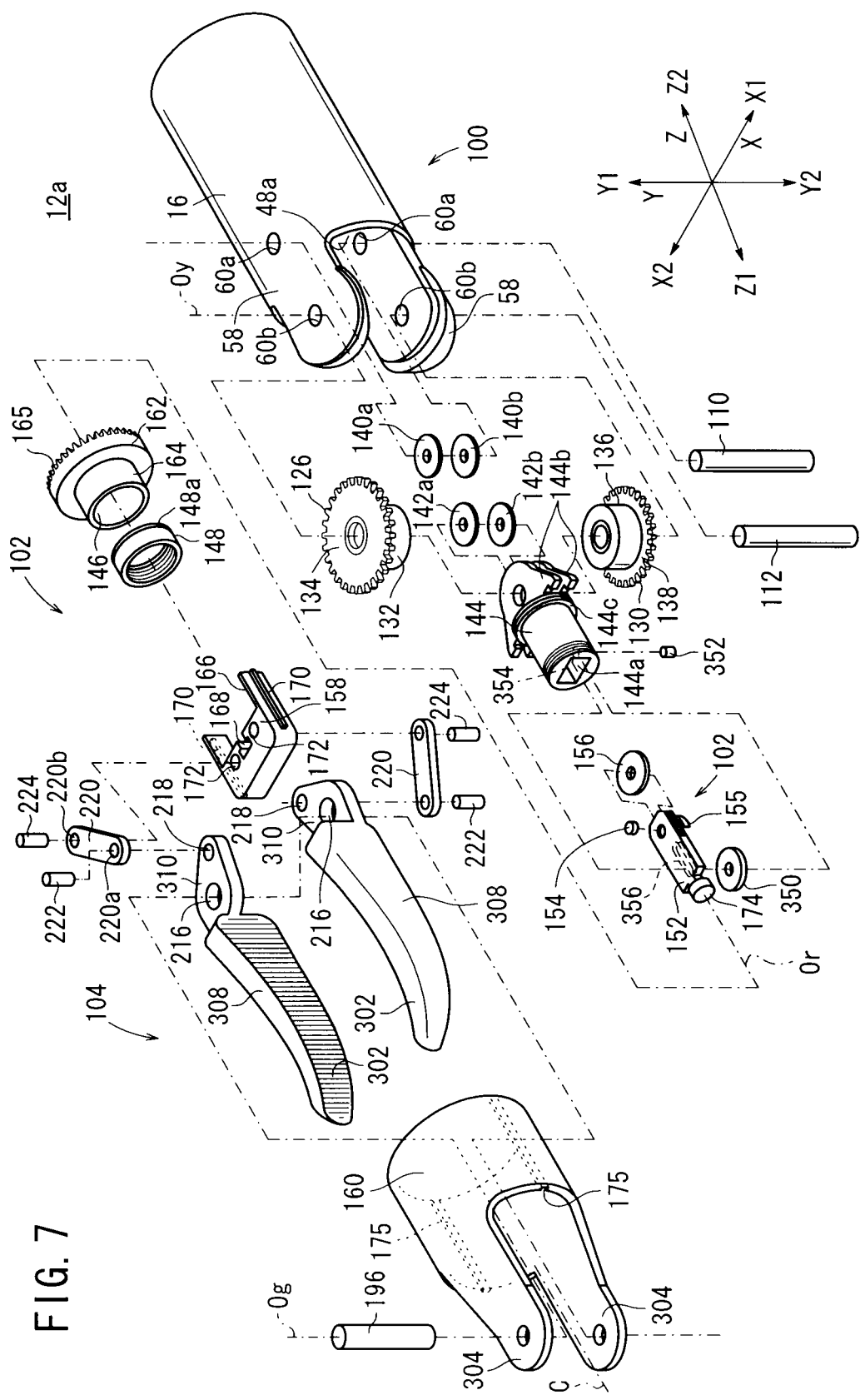
FIG. 7 is an exploded perspective view of the distal-end working unit.
Figure 8:
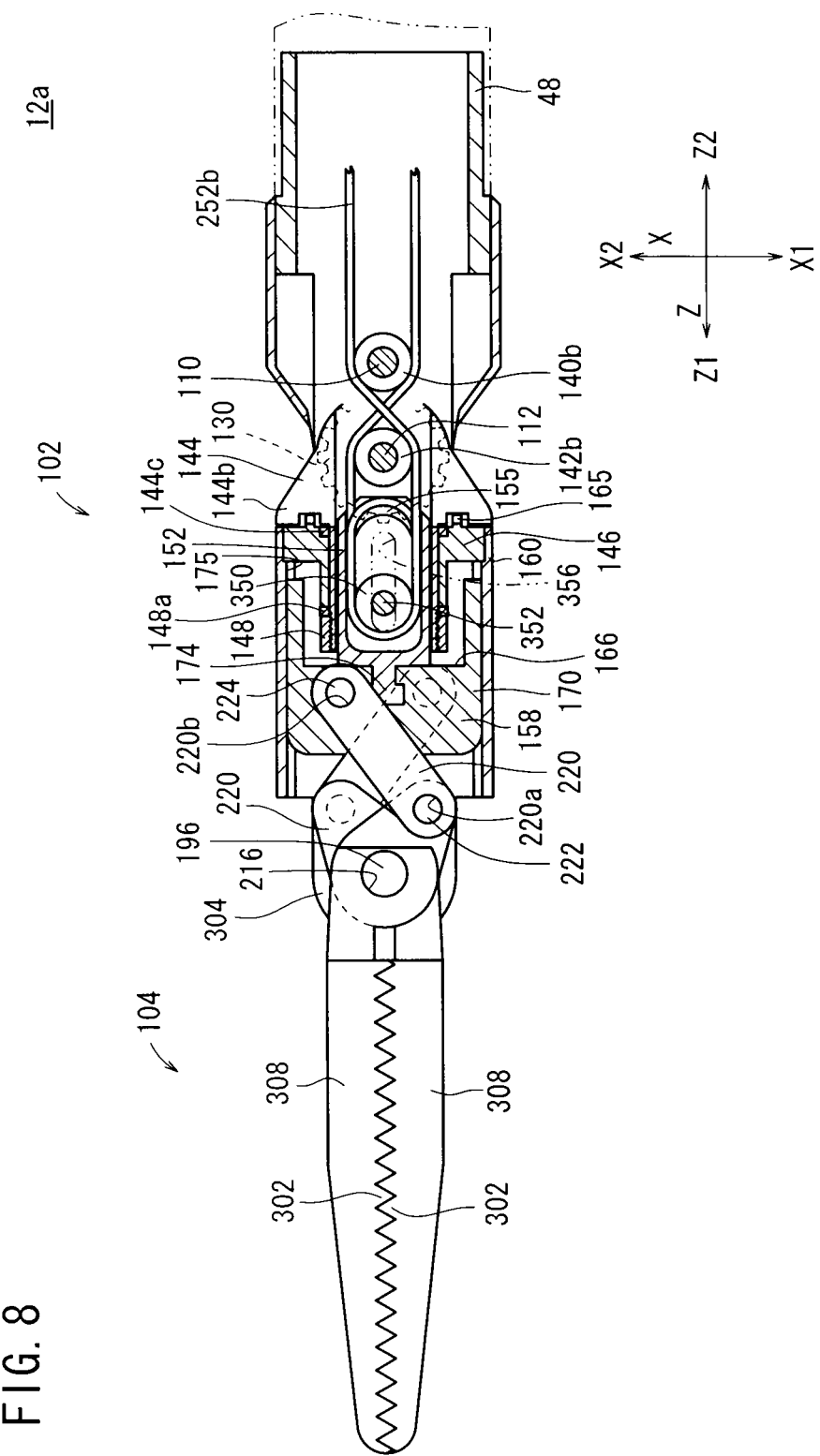
FIG. 8 is a sectional side elevational view of the distal-end working unit with a gripper being closed.
Figure 9:
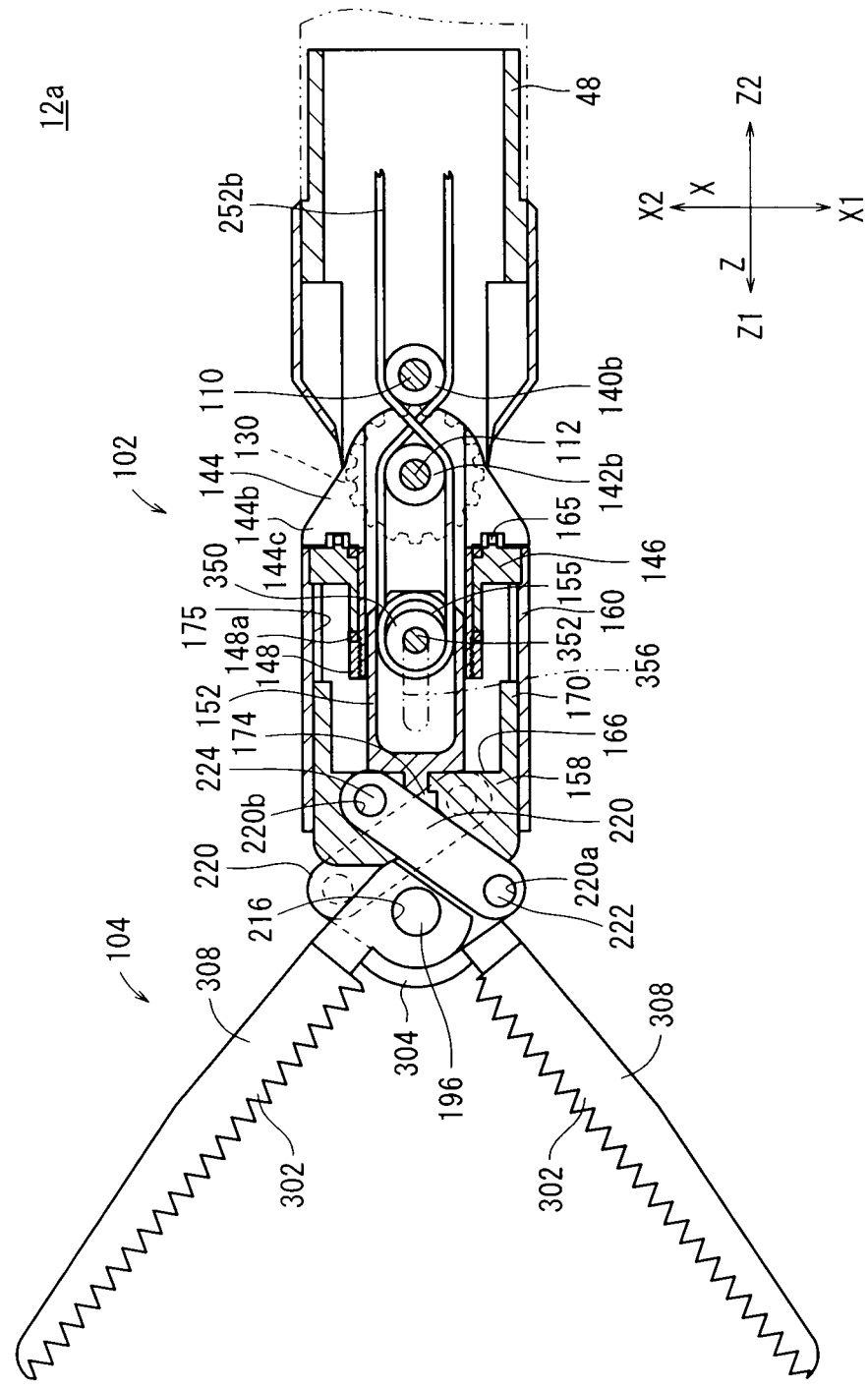
FIG. 9 is a sectional side elevational view of the distal-end working unit with the gripper being opened.

As shown in FIGS. 7, 8 and 9, the distal-end working unit 12a comprises a wire-driven mechanism 100, a composite mechanism 102, and the end effector 104. The distal-end working unit 12a incorporates therein mechanisms that provide three degrees of freedom. The mechanisms include a mechanism having a first degree of freedom for turning a portion of the distal-end working unit 12a, which is positioned ahead of a first rotational axis Oy extending along the Y directions, in yawing directions about the first rotational axis Oy, a mechanism having a second degree of freedom for turning the portion of the distal-end working unit 12a in rolling directions about a second rotational axis Or, and a mechanism having a third degree of freedom for opening and closing the end effector 104 on the distal end of the distal-end working unit 12a about a third rotational axis Og.

The first rotational axis Oy of the mechanism having the first degree of freedom may be turnable out of parallelism with an axis C, which extends from the proximal end toward the distal end of the joint shaft 48. The second rotational axis Or of the mechanism having the second degree of freedom may be turnable about an axis along a direction in which the distal end (end effector 104) of the distal-end working unit 12a extends, with the distal end portion thereof being rotatable in the rolling directions.

The mechanism having the first degree of freedom (i.e., which is movable in the yawing directions) has an operable range of ±90° or greater, for example. The mechanism having the second degree of freedom (i.e., which is movable in the rolling directions) has an operable range of ±180° or greater, for example. The mechanism having the third degree of freedom (i.e., the end effector 104) may be opened through an operable range of 40° or greater, for example.

The end effector 104 comprises a member for enabling actual techniques during surgical operations to be performed. The first rotational axis Oy and the second rotational axis Or are axes for changing the attitude of the end effector 104, for thereby facilitating such techniques. Generally, the mechanism having the third degree of freedom for opening and closing the end effector 104 is referred to as a gripper or a gripper axis. The mechanism having the first degree of freedom for turning in yawing directions is referred to as a yaw axis, whereas the mechanism having the second degree of freedom for turning in rolling directions is referred to as a roll axis.

As shown in FIG. 7, the wire-driven mechanism 100 is disposed between a pair of tongue pieces 58 and serves to convert reciprocating movements of respective wires 52, 54 into rotational movements, as well as to transmit such rotational movements to the composite mechanism 102. The wire-driven mechanism 100 includes a shaft 110 inserted into shaft holes 60a, 60a, and a shaft 112 inserted into shaft holes 60b, 60b. The shafts 110, 112 are press-fitted or welded securely in the shaft holes 60a, 60b. The shaft 112 is axially aligned with the first rotational axis Oy.

Gear bodies 126, 130, which are symmetrically shaped in the Y directions, are mounted respectively on both ends of the shaft 112 in the Y directions. The gear body 126 comprises a tubular member 132, with a gear 134 disposed concentrically on an upper portion of the tubular member 132. The gear body 130 essentially is identical in shape to the gear body 126, but is inverted and aligned with the gear body 126 in the Y directions. The gear body 130 comprises a tubular member 136, with a gear 138 disposed concentrically on a lower portion of the tubular member 136. The gears 134, 138 are held in mesh with upper and lower ends of a face gear 165 of a gear body 146, to be described later.

The tubular member 136 is substantially identical in diameter and shape to the tubular member 132. The wires 52, 54 (see FIG. 3) are wound around the tubular members 132, 136, and portions of the wires 52, 54 are fastened to the tubular members 132, 136 by a given securing means.

When the wires 52, 54 are rotated, the gear bodies 126, 130 are rotated about the shaft 112. When the gear bodies 126, 130 are rotated at the same speed and in the same direction, the gear body 146 swings with respect to the shaft 112 and moves in yawing directions. When the gear bodies 126, 130 are rotated at the same speed but in opposite directions, the gear body 146 is rotated about the second rotational axis Or and moves in rolling directions. When the gear bodies 126, 130 are rotated at different speeds, the gear body 146 makes a composite motion, made up of both yawing and rolling directions. The gear body 126, the gear body 130, and the gear body 146 collectively make up a differential mechanism.

A pair of idle pulleys (idle cylindrical members) 140a, 140b are rotatably supported substantially centrally on the shaft 110, and a pair of guide pulleys (cylindrical guide members) 142a, 142b are rotatably supported substantially centrally on the shaft 112. The idle pulley 140a serves to keep the driven wire 1252a wound around the guide pulley 142a through a constant angle (about 180° on both sides thereof) at all times. The idle pulley 140a and the guide pulley 142a may have a smooth surface or may be made of a material having a small coefficient of friction in order to reduce slippage and frictional wear on the driven wire 252a (see FIG. 4).

A main shaft 144 is rotatably supported on the shaft 112 between the gear body 126 and the guide pulley 142a, and also between the guide pulley 142b and the gear body 130. The main shaft 144 has a sleeve that projects toward the composite mechanism 102. The main shaft 144 has a square hole 144a formed axially therein. The sleeve has a diametrical shaft hole 354 formed therein, with a pin 352 being inserted and fixed in the shaft hole 354. The shaft hole 354 extends axially in the sleeve of the main shaft 144, in the Y2 direction on one side of the square hole 144a. The pin 352 extends through the shaft hole 354 and into a recess 356 formed in the transmitting member 152 (see FIG. 11). The main shaft 144 includes two auxiliary plates 144b disposed on an end thereof in the Z2 direction for holding both surfaces of the guide pulleys 142a, 142b in the Y directions. The auxiliary plates 144b have respective holes through which the shaft 112 extends. The auxiliary plates 144b are of a chevron shape, which becomes progressively wider in the Z1 direction, for preventing foreign matter such as threads from entering therein.

As shown in FIG. 3, the idle pulleys 140a, 140b are coaxial with each other, and the guide pulleys 142a, 142b are coaxial with each other. The idle pulleys 140a, 140b are rotatably supported on a common shaft 110, while the guide pulleys 142a, 142b are rotatably supported on a common shaft 112. Since the guide pulleys 142a, 142b are coaxial with each other, the medical manipulator 10 is made tiltable about the yaw-axis by means of a simple mechanism.

The composite mechanism 102 includes an opening/closing mechanism for opening and closing the end effector 104, and an attitude changing mechanism for changing the attitude of the end effector 104.

The composite mechanism 102 comprises the gear body 146, which is rotatably fitted over the circumferential surface of the sleeve of the main shaft 144, a nut 148 mounted on the distal end of the main shaft 144, the transmitting member 152 having an end in the Z2 direction which is inserted into the hole 144a, a driven pulley 156a rotatably supported by a pin 154 on the end in the Z2 direction of the transmitting member 152, a driven plate 158, a hollow cylindrical cover 160, and the return pulley 350, which is rotatably supported on the pin 352. The transmitting member 152 has an end in the Z2 direction, which is of a channel shape for enabling better slidability against the driven pulley 156, and which extends over a long distance in the Z2 direction.

A thrust bearing 144c, which is made of resin, is disposed on a portion of the main shaft 144 that abuts against the gear body 146. A thrust bearing 148a, also made of resin, is disposed on a portion of the nut 148 that abuts against the gear body 146. The thrust bearings 144c, 148a are made of a material having a low coefficient of friction, for reducing wear and torque on the abutting portions, and for preventing loads from being applied directly to the face gear 165. The thrust bearings 144c, 148a comprise slide bearings, but may comprise roller bearings. When the end effector 104 is strongly closed or opened, i.e., when the gear body 146 is held strongly in abutment with the main shaft 144, the distal-end working unit 12a can be turned smoothly about the roll axis. The hole 144a is high enough to allow the transmitting member 152, the crescent driven member 155, the driven pulley 156, and the return pulley 350 to be inserted therein.

The gear body 146 has a stepped shape, comprising a large-diameter portion 162 projecting in the Z2 direction, a small-diameter portion 164 projecting in the Z1 direction, and a face gear 165 on the end of the large-diameter portion 162 facing in the Z2 direction. The face gear 165 is held in mesh with the gears 134 and 138. The gear body 146 is prevented by the nut 148 from becoming dislodged from the main shaft 144. The sleeve of the main shaft 144 has an externally threaded outer circumferential surface over which the nut 148 is screwed.

The transmitting member 152 is disposed in a position slightly offset from the central axis of the working unit 16 in the Y1 direction. However, a mushroom-shaped knob 174 on the distal end of the transmitting member 152 in the Z1 direction is held in alignment with the central axis of the working unit 16. Alternatively, the transmitting member 152 may be disposed in alignment with the central axis of the working unit 16.

The driven plate 158 has a recess 166 that opens in the Z2 direction, an engaging cavity 168 formed in the bottom of the recess 166, axial ribs 170 disposed respectively on both surfaces of the driven plate 158 in the Y directions, and a pair of link holes 172 formed symmetrically in both sides of the engaging cavity 168. The engaging cavity 168 is of a shape which is capable of engagement with the mushroom-shaped knob 174 on the distal end of the transmitting member 152. When the mushroom-shaped knob 174 engages within the engaging cavity 168, the driven plate 158 and the transmitting member 152 are capable of rotating relatively to each other about the roll axis. The driven plate 158 has a width substantially equal to the inside diameter of the cover 160.

The cover 160 has a size that is large enough to cover the composite mechanism 102 substantially in its entirety, and serves to prevent foreign matter (living tissues, medications, threads, etc.) from entering into the composite mechanism 102 and the end effector 104. The cover 160 has two axial grooves 175 formed along the inner circumferential surface thereof so as to diametrically face each other. The ribs 170 of the driven plate 158 are fitted respectively into the grooves 175 for axially guiding the driven plate 158. Since the knob 174 engages within the engaging cavity 168 of the driven plate 158, the crescent driven member 155 and the driven pulley 156 are axially movable back and forth in the hole 144a together with the driven plate 158 and the transmitting member 152, and can roll about the transmitting member 152. The cover 160 is fixed to the large-diameter portion 162 of the gear body 146 by means of a threaded engagement, press-fitted engagement, or the like.

The end effector 104 comprises a pair of end effector members 308, and a pin 196 on which the end effector members 308 are pivotally supported. The pin 196 is aligned with the third rotational axis Og.

The end effector 104 is of a double-acting type having two movable grippers 302. The end effector 104 includes a pair of gripper bases 304 formed integrally with the cover 160, the end effector members 308, which are turnable about the pin 196 mounted on the gripper bases 304, and a pair of gripper links 220.

Each of the end effector members 308 is L-shaped and has a gripper 302 extending in the Z1 direction, and a lever 310 bent about 35° with respect to the gripper 302. The end effector member 308 also has a hole 216 formed in an L-shaped bent corner thereof, and a hole 218 formed therein near an end portion thereof. When the pin 196 is inserted into the hole 216, the end effector members 308 are made openable and closable about the third rotational axis Og.

Each of the end effector members 308 is joined to a pin 224 of the driven plate 158 by the gripper link 220. The link holes 172 of the driven plate 158 are disposed in respective symmetrical positions in the X directions in FIG. 7. The gripper links 220 cross each other when viewed in side elevation.

Since the grippers 302 are disposed in facing positions, the distal-end working unit 12a is capable of exerting well balanced forces, without imposing inadvertent moment loads.

As shown in FIGS. 8 and 9, the end effector members 308 basically are actuated synchronously, in response to operation of the transmitting member 152. Therefore, the end effector members 308 are openable and closable symmetrically with respect to the central axis.

Figure 10:
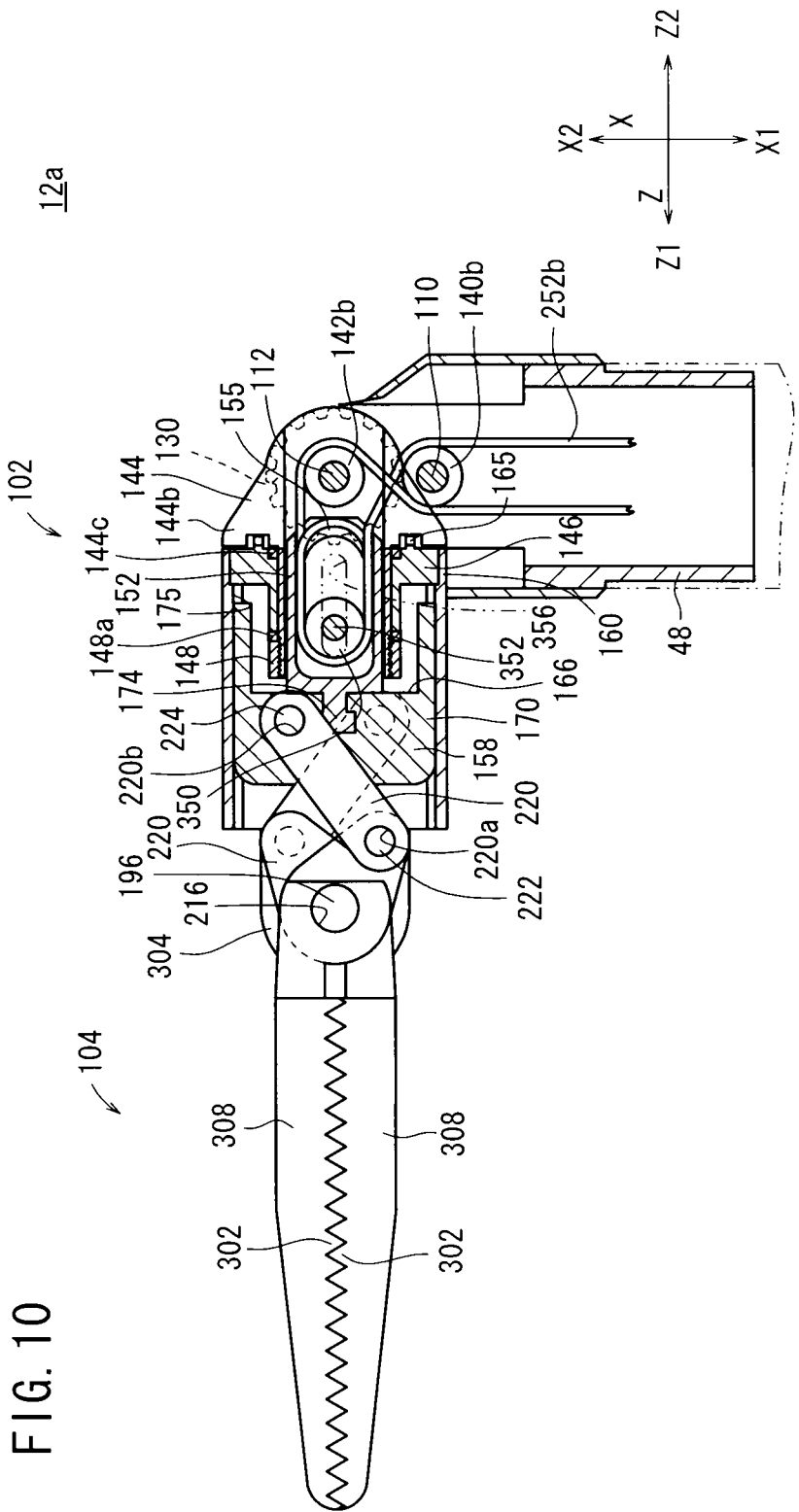
FIG. 10 is a sectional plan view of the distal-end working unit which is turned about a roll axis in one direction.

As shown in FIG. 10, when the end effector 104 moves about the yaw axis, the composite mechanism 102 and the end effector 104 are turned in yawing directions about the shaft of the guide pulleys 142a, 142b (see FIG. 3). Since the distal-end working unit 12a comprises a non-interference mechanism, the degree of opening of the end effector 104 does not change when the end effector 104 moves about the yaw axis. Conversely, when the end effector 104 is opened and closed, the end effector 104 does not move about the yaw axis or the roll axis.

Since the end effector 104 is mechanically connected directly to the trigger lever 32, the end effector 104 produces strong gripping forces. The forces applied to the end effector 104 are transmitted to the trigger lever 32.

The wire drive ratio of the distal-end working unit 12a, at times when the end effector 104 is operated to grip and open, is 1:1, and therefore the distal-end working unit 12a is well balanced.

Structural details of the transmitting member 152, the driven pulley 156 mounted on the transmitting member 152, the crescent driven member 155, and the return pulley 350 will be described below.

The guide pulley 142a, the driven pulley 156, and the return pulley 350 essentially are of the same diameter. The idle pulley 140a is larger in diameter than the guide pulley 142a, in order to reduce the gap between the idle pulley 140a and the guide pulley 142a. The reduced gap between the idle pulley 140a and the guide pulley 142a allows the distal-end working unit 12a to operate within a wide range about the yaw axis. The idle pulley 140a, the guide pulley 142a, the driven pulley 156, and the return pulley 350 are of relatively large diameters in layout, so that the driven wires 252a, 252b will not experience sharp bends.

Figure 11:
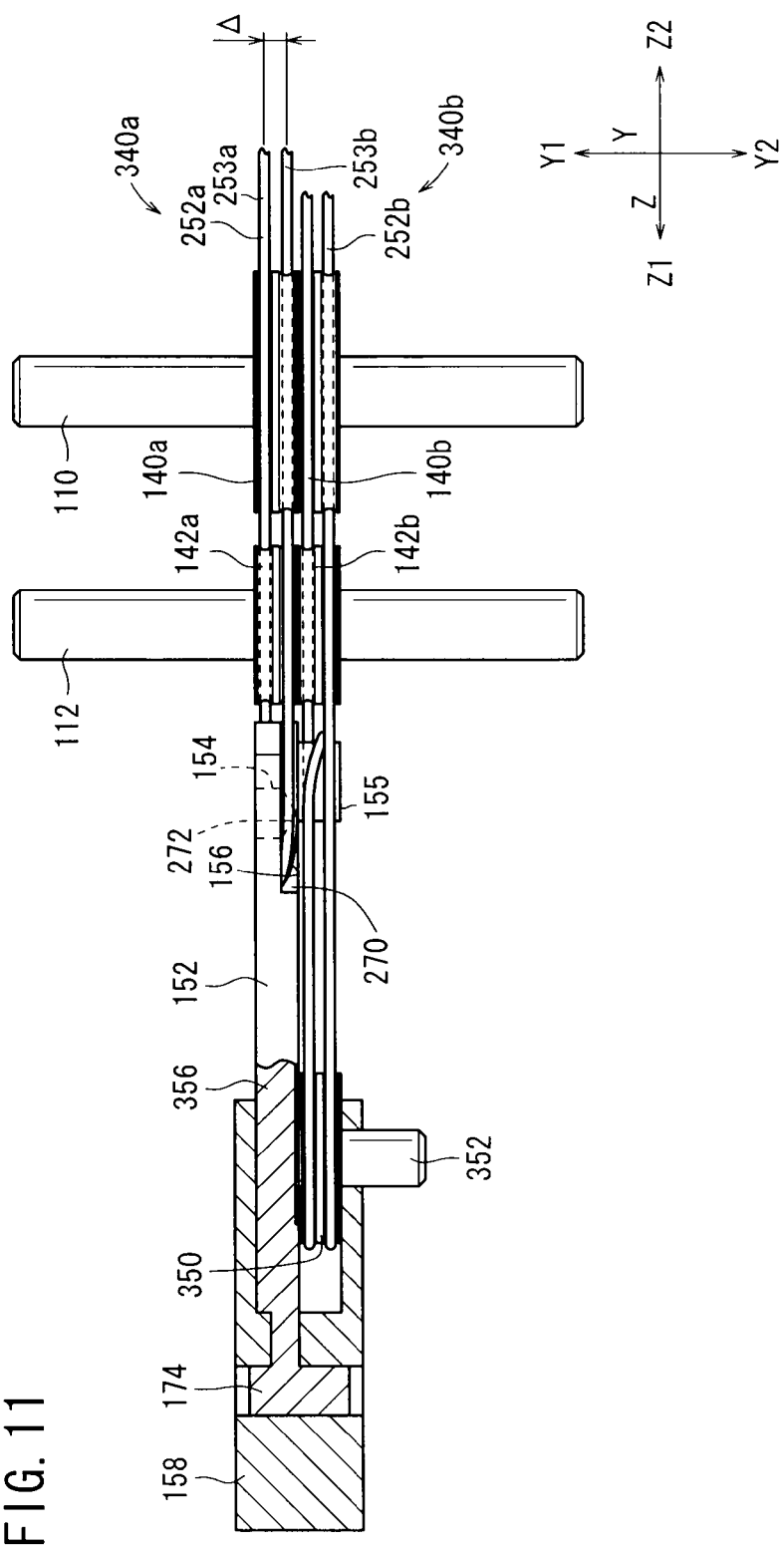
FIG. 11 is a side elevational view of the first end effector drive mechanism and the second end effector drive mechanism.

As shown in FIGS. 6 and 11, the transmitting member 152 is in the form of a plate, which is thin in the Y directions and elongated in the Z directions. The transmitting member 152 comprises the pin 154, the crescent driven member 155, the driven pulley 156, the knob 174, the pin 352, and the recess 356. The driven pulley 156 includes a groove (a cylindrical driven member groove) 156c therein, which is formed in a side surface thereof for circumferentially guiding the driven wire 252a.

The knob 174 is disposed on an end of the transmitting member 152 in the Z1 direction, and has a mushroom-shaped cylindrical distal end portion that engages within the engaging cavity 168. When the mushroom-shaped knob 174 engages within the engaging cavity 168, the transmitting member 152 can transmit movements therefrom in the Z directions to the driven plate 158, while the driven plate 158 is capable of rotating about the roll axis.

The recess 356 comprises a bottomed hole formed substantially centrally in the transmitting member 152, which is elongated in the Z directions and concave in the Y1 direction from the side surface of the transmitting member 152, which faces in the Y2 direction. Depending on design conditions, the recess 356 may be a through hole. The pin 352 is press-fitted into the shaft hole 354, which is formed in the surface and faces in the Y2 direction of the sleeve of the main shaft 144 (see FIG. 7). The pin 352, on which the return pulley 350 is rotatably supported, extends into the recess 356 of the transmitting member 152. The pin 352 does not extend through the transmitting member 152, but rather, is of a cantilevered structure (see FIG. 11). If the pin 352 were to extend through the transmitting member 152, then when the transmitting member 152 is displaced a maximum stroke in the Z1 direction, as shown in FIG. 12B, the pin 352 would obstruct movement of the driven pulley 156, as can easily be seen from FIG. 11. Actually, however, since the pin 352 does not reach the location of a pulley groove 270, to be described later, the pin 352 does not obstruct movement of the driven pulley 156. The return pulley 350 is in contact with the side surface of the transmitting member 152, which faces in the Y2 direction, and the return pulley 350 is rotatably supported on the pin 352 in the hole 144a of the main shaft 144. The pin 352 and the return pulley 350 are thus fixed in position.

As shown in FIGS. 6 and 11, the crescent driven member 155 is integral with the transmitting member 152, and projects from the side surface of the transmitting member 152, which faces in the Y2 direction, near the end of the transmitting member in the Z2 direction. The crescent driven member 155 has a width which is large enough to support two turns of the driven wire 252b. Since the crescent driven member 155 is integral with the transmitting member 152, the total number of separate components making up the distal-end working unit 12a is reduced.

As shown in FIG. 12A, the crescent driven member 155 comprises a substantially crescent shape, which is convex in the Z2 direction when viewed along the Y directions. The crescent driven member 155 has a concave surface (arcuate concave surface) 155a, which is open or concave in the Z1 direction, and a convex surface (arcuate convex surface) 155b, which is convex in the Z2 direction. The concave surface 155a is represented by an arc having a radius ra. The convex surface 155b is represented by an arc having a radius rb.

Figure 13A:
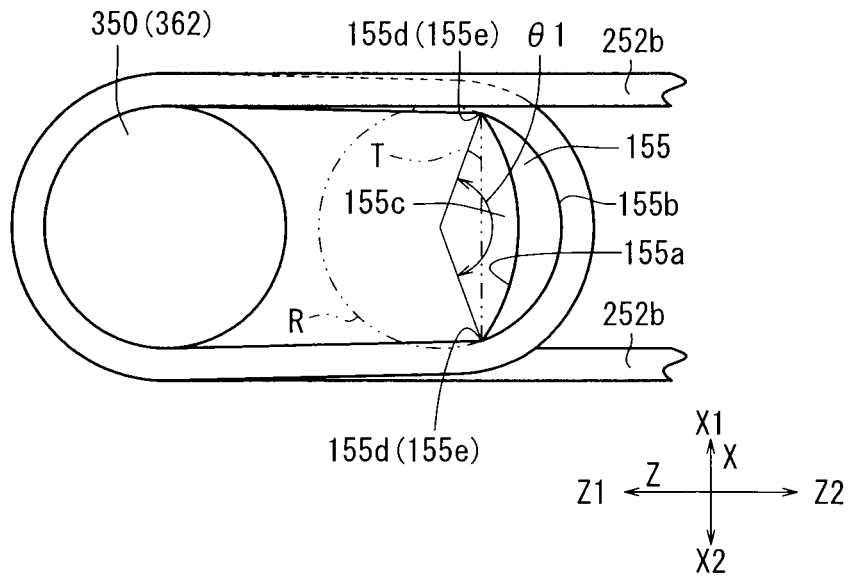
FIG. 13A is a plan view, partially omitted in illustration, showing the positional relationship between the return pulley, the crescent driven member, and a driven wire with a convex surface being represented by an arc having a central angle θ1 of 140°.
Figure 13B:
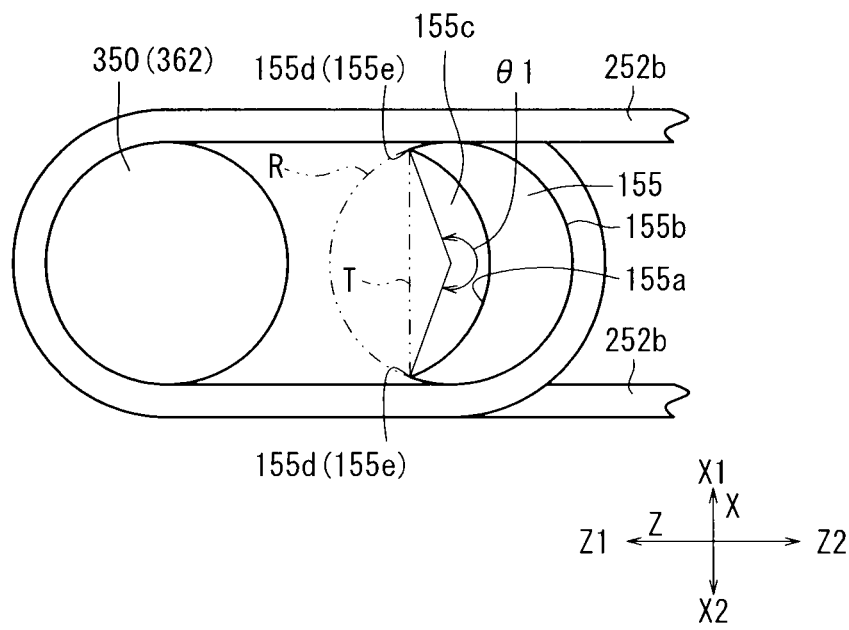
FIG. 13B is a plan view, partially omitted in illustration, showing the positional relationship between the return pulley, the crescent driven member, and the driven wire with the convex surface being represented by an arc having a central angle θ1 of 220°.

The radius rb of the convex surface 155b is equal to or greater than the radius rc of the return pulley 350, and is of a relatively large diameter in layout, so that the driven wire 252b will not undergo sharp bends. As shown in FIGS. 13A and 13B, the arc representing the convex surface 155b has a central angle θ1 that ranges from 140° to 220°, and more preferably, which ranges from 170° to 180°. In FIG. 13A, the arc representing the convex surface 155b has a central angle θ1 of 140°. In FIG. 13B, the arc representing the convex surface 155b has a central angle θ1 of 220°. Since the central angle θ1 falls within the above range, the crescent driven member 155 provides a continuous path for the driven wire 252b at opposite convex ends 155d of the convex surface 155b, and also prevents the driven wire 252b from experiencing sharp bends, thereby reducing loads imposed on the driven wire 252b as the driven wire 252b moves along the convex surface 155b. The convex surface 155b of the crescent driven member 155 may be represented by an elliptical arc having a major axis longer than the radius rc of the return pulley 350.

Figure 14A:
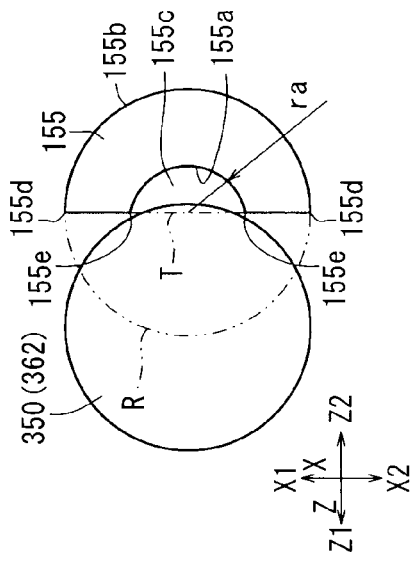
FIG. 14A is a plan view, partially omitted in illustration, showing the positional relationship between the return pulley and the crescent driven member with the radius of a concave surface being equal to or greater than the radius of the return pulley.
Figure 14B:
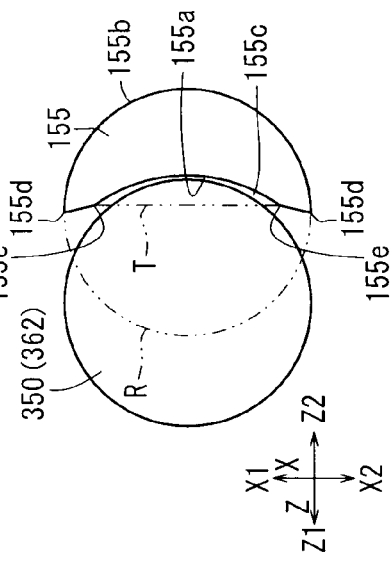
FIG. 14B is a plan view, partially omitted in illustration, showing the positional relationship between the return pulley and the crescent driven member with the radius of the concave surface being smaller than the radius of the return pulley, and also with the convex surface having opposite ends that differ from the opposite ends of the concave surface.

As shown in FIG. 12A, when the return pulley 350 is moved toward the proximal end, the proximal-end portion thereof can move in the Z2 direction beyond a chord line T, which interconnects opposite concave ends 155e of the concave surface 155a, i.e., the proximal-end portion can enter a cavity 155c, which is surrounded by the chord line T and the concave surface 155a. There are no specific limitations imposed on the relationship between the radius ra of the concave surface 155a and the radius rc of the return pulley 350. However, if the radius ra is equal to or greater than the radius rc, then the proximal-end portion of the return pulley 350 can move in the Z2 direction beyond the chord line T, i.e., the proximal-end portion can enter the cavity 155c by a greater distance than if the radius ra were smaller than the radius rc. Accordingly, the radius ra of the concave surface 155a should preferably be equal to or greater than the radius rc of the return pulley 350. In FIG. 14A, the radius ra is shown as being equal to or greater than the radius rc. In FIG. 14B, the radius ra is shown as being smaller than the radius rc.

As described above, the crescent driven member 155 formed integrally with the transmitting member 152 is movable in the Z1 direction. As shown in FIGS. 12A and 12B, the transmitting member 152 has a length W1 in the Z directions. As shown in FIG. 12A, when the transmitting member 152 is moved a maximum distance in the Z2 direction, i.e., when the grippers 302 are closed, the end of the transmitting member 152 in the Z1 direction is spaced from the end of the return pulley 350 in the Z1 direction by a distance L0. The transmitting member 152 is movable a maximum distance W0 in the Z directions. As shown in FIG. 12B, when the return pulley 350 has fully entered into the cavity 155c, or when the return pulley 350 is closest to the concave surface 155a, i.e., when the grippers 302 are fully opened, the end of the return pulley 350 in the Z1 direction is spaced from the end of the transmitting member 152 in the Z2 direction by a distance L1. In this case, the dimensional relationship W1=L0+L1+W0 is satisfied.

Figure 15A:
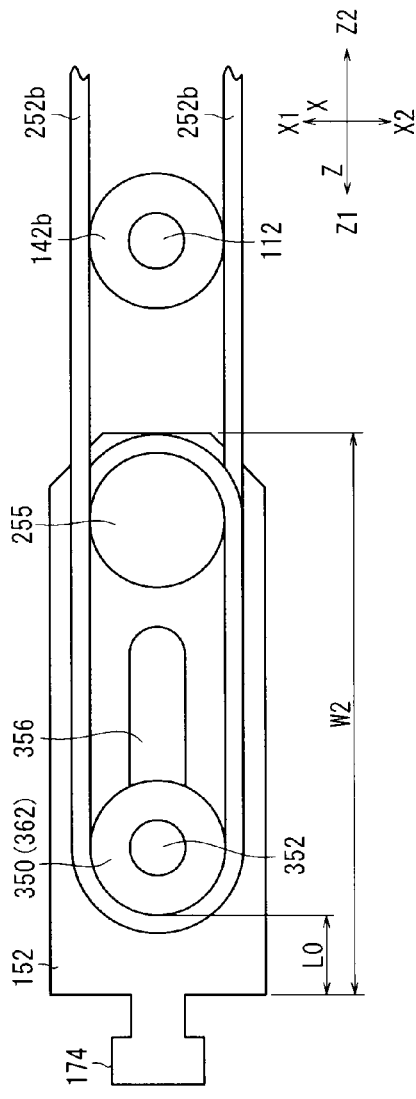
FIG. 15A is a view showing the positional relationship between a transmitting member, a cylindrical driven member, and a return pulley with the gripper being closed.
Figure 15B:
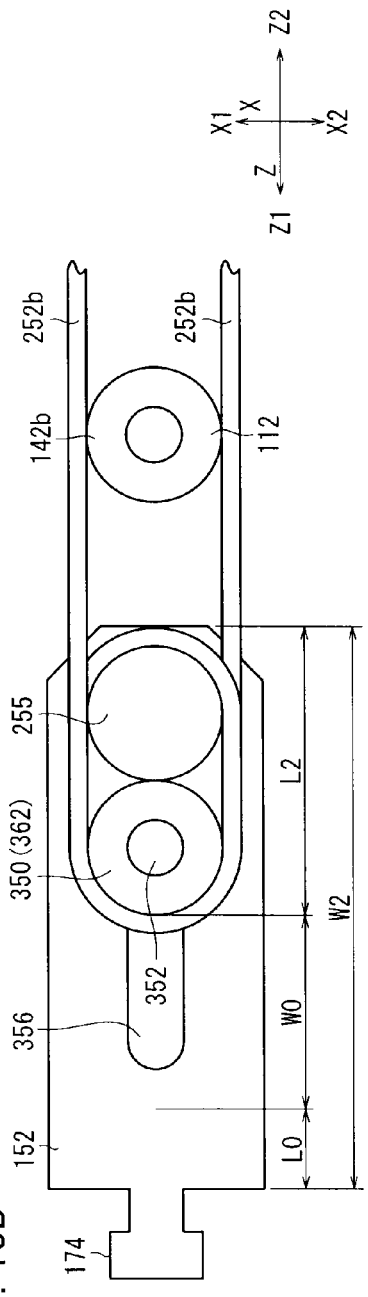
FIG. 15B is a view showing the positional relationship between the transmitting member, the cylindrical driven member, and the return pulley with the gripper being opened to a maximum.

FIGS. 15A and 15B show a comparative example in which the crescent driven member 155 is replaced with a cylindrical driven member 255 having the same diameter as the return pulley 350. The transmitting member 152 has a length W2 in the Z directions. As shown in FIG. 15A, the distance from the end of the transmitting member 152 in the Z1 direction to the end of the return pulley 350 in the Z1 direction is the same as the distance L0, similar to the case of the crescent driven member 155. Since the end effector 104 is openable and closable as the transmitting member 152 is moved back and forth, in order to keep the operating angle of the end effector 104 the same as that of the crescent driven member 155, the maximum distance that the transmitting member 152 can be moved in the Z directions is the same as the distance W0, in the same manner as with the crescent driven member 155. Furthermore, when the grippers 302 are fully opened, as shown in FIG. 15B, the end of the return pulley 350 in the Z1 direction is spaced from the end of the transmitting member 152 in the Z2 direction by a distance L2. As can be seen from FIG. 15B, the distance L2 occurs when the return pulley 350 abuts against the cylindrical driven member 255. In this case, the dimensional relationship W2=L0+L2+W0 is satisfied.

The above equations W1=L0+L1+W0 and W2=L0+L2+W0 imply that, since the distances L0, W0 are common, the difference between the distance W1 and the length W2 is equal to the difference between the distances L1 and L2. A comparison between FIGS. 12A, 12B and FIGS. 15A, 15B, i.e., between the assembly including the crescent driven member 155 and the assembly including the cylindrical driven member 255, shows that the distance L1 is smaller than the distance L2, because the proximal-end portion of the return pulley 350 enters into the cavity 155c. Therefore, the distance W1 is smaller than the length W2, and accordingly, the crescent driven member 155 makes it possible to reduce the size of the transmitting member 152 in the Z directions. Furthermore, as described above, since the cantilevered pin 352 does not enter into the pulley groove 270, it is possible to maintain the distance W0, i.e., to maintain the operating angle of the end effector 104, even though the distance W1 is smaller than the length W2.

Figure 14C:
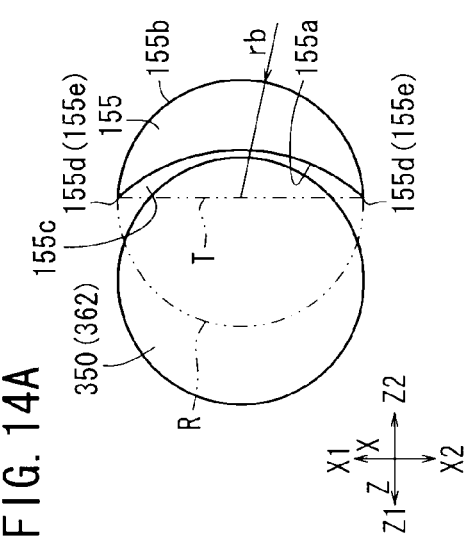
FIG. 14C is a plan view, partially omitted in illustration, showing the positional relationship between the return pulley and the crescent driven member, the concave surface of which is not arcuate.
Figure 14D:
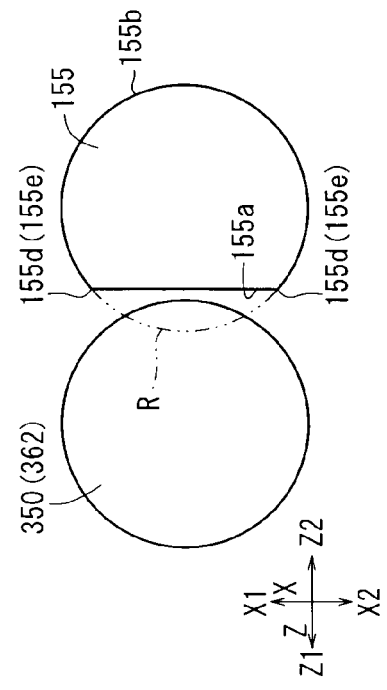
FIG. 14D is a plan view, partially omitted from illustration, showing the positional relationship between the return pulley and the crescent driven member having a convex surface, which is different from the convex surface shown in FIG. 14B, and having opposite ends that differ from the opposite ends of the concave surface.

In the above embodiment, the proximal-end portion of the return pulley 350 enters sufficiently into the cavity 155c. However, the crescent driven member 155 may have an arcuate shape, so that the crescent driven member 155 is devoid of at least a distal-end portion, and wherein a circle including a portion represented by the arc of the convex surface 155b may be represented by a virtual circle R (see FIG. 12A). If the proximal-end portion of the return pulley 350 crosses the virtual circle R, then the distance W1 is smaller than the length W2. Therefore, a crescent driven member 155 shaped in this manner also enables a reduction in size of the transmitting member 152 in the Z directions. The arc of the arcuate shape, which is devoid of at least a distal-end portion, should not be interpreted in a strict sense. Rather, the arc may be of a crescent shape, a semicircular shape, a sectorial shape, or the like. Likewise, although the concave surface 155a of the crescent driven member 155 is arcuate in the above description, the concave surface 155a may have a non-convex shape (a concave shape or a flat surface) toward the distal end which is interpreted in a broader sense, because the proximal-end portion of the return pulley 350 may cross the virtual circle R. FIG. 14C shows a flat surface 155a extending in the X directions, rather than a concave surface 155a. In FIGS. 12A, 12B, 13A and 13B, opposite convex ends 155d of the convex surface 155b share the same points as the opposite concave ends 155e of the concave surface 155a. However, as shown in FIGS. 14B and 14D, the opposite convex ends 155d and the opposite concave ends 155e may be located at different points. Furthermore, since the cantilevered pin 352 does not enter into the pulley groove 270, it is possible to maintain the distance W0, i.e., to maintain the operating angle of the end effector 104, even though the distance W1 is smaller than the length W2.

In the case of the crescent driven member 155, with the transmitting member 152 having the length W2 in the Z directions, the maximum distance that the transmitting member 152 is capable of moving can be greater than the distance W0, thus making it possible to increase the operating angle of the end effector 104.

While the end effector 104 grips an object, the driven wire 252b in contact with the crescent driven member 155 does not move, due to frictional forces between the driven wire 252b and the crescent driven member 155. Therefore, the crescent driven member 155 is not required to be rotatable, as is the case with the driven pulley 156. Consequently, the crescent driven member 155 should preferably be of a crescent shape, which can be made smaller in size than a cylindrical shape.

Figure 16:
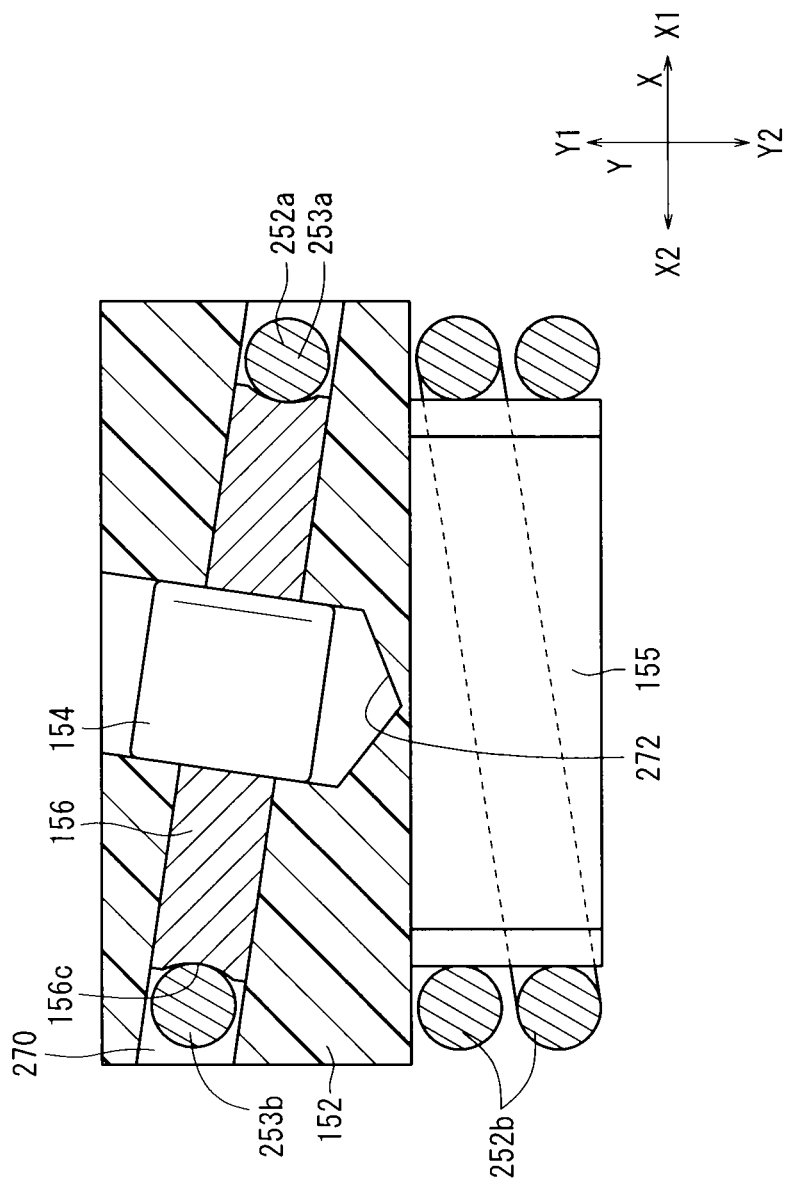
FIG. 16 is a cross-sectional view of the transmitting member as viewed in a Z1 direction.

As shown in FIGS. 11 and 16, the transmitting member 152 has a pulley groove 270, which is formed in an end thereof in the Z directions, and in which the driven pulley 156 is disposed. The transmitting member 152 further includes a pin 154 on which the driven pulley 156 is rotatably supported in the pulley groove 270. The pin 154 is press-fitted into an oblique hole 272. The pulley groove 270 is slightly wider than the driven pulley 156, and opens on the surface of the transmitting member 152, which faces in the Z2 direction, so that the driven wire 272a can pass therethrough. The pulley groove 270 extends slightly obliquely to the X directions from the surface of the transmitting member 152, which faces in the X1 direction, toward the surface of the transmitting member 152, which faces in the X2 direction. Since the pulley groove 270 is narrow, as shown in FIG. 16, the driven wire 252a does not drop off from the circumferential surface of the driven pulley 156. Due to the groove 156c of the driven pulley 156, the driven wire 252a is kept out of sliding contact with the wall surface of the pulley groove 270, and is held stably in position.

The oblique hole 272 and the pin 154 are oriented in a direction perpendicular to upper and lower surfaces of the pulley groove 270, and are inclined in an XY plane to the Y-direction axis (or stated otherwise, the direction of the shaft 112 on which the guide pulley 142a is rotatably supported). The oblique hole 272 consists of a bottomed hole, which opens only in the surface that faces in the Y1 direction. However, depending on design conditions, the oblique hole 272 may comprise a through hole.

Figure 17:
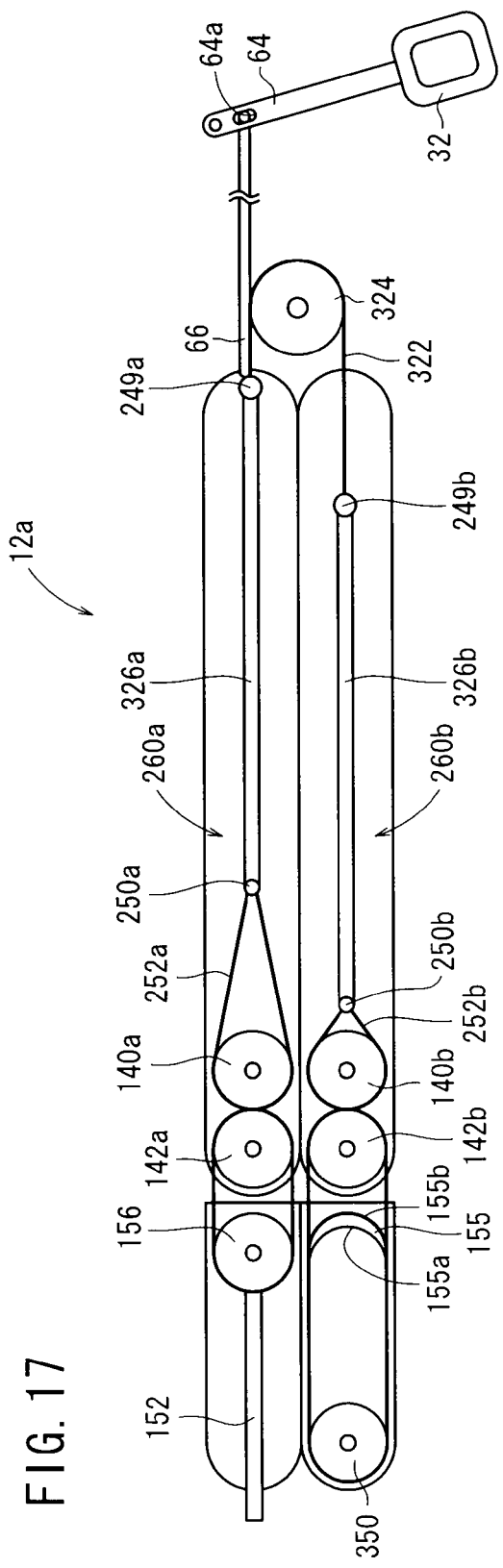
FIG. 17 is a schematic plan view of a distal-end working unit incorporating straight-motion rods.

The wires 56a, 56b (see FIG. 4) of the first end effector drive mechanism 260a and the second end effector drive mechanism 260b may be replaced with straight-motion rods 326a, 326b, as shown in FIG. 17. Since rods are generally more rigid than wires, portions thereof that make only straight motions can produce large gripping forces and have a prolonged service life, if the first end effector drive mechanism 260a and the second end effector drive mechanism 260b are replaced with rods.

The drive joint pulley 324 around which the drive joint wire 322 is trained may be dispensed with, in which case the wires 56a, 56b and the straight-motion rods 326a, 326b shown in FIG. 17 are connected directly to the trigger lever 32. As shown in FIG. 17, the wires 56a, 56b and the straight-motion rods 326a, 326b may have, at some location thereon, a load limiter for preventing excessive loads from being applied thereto.

Figure 18:
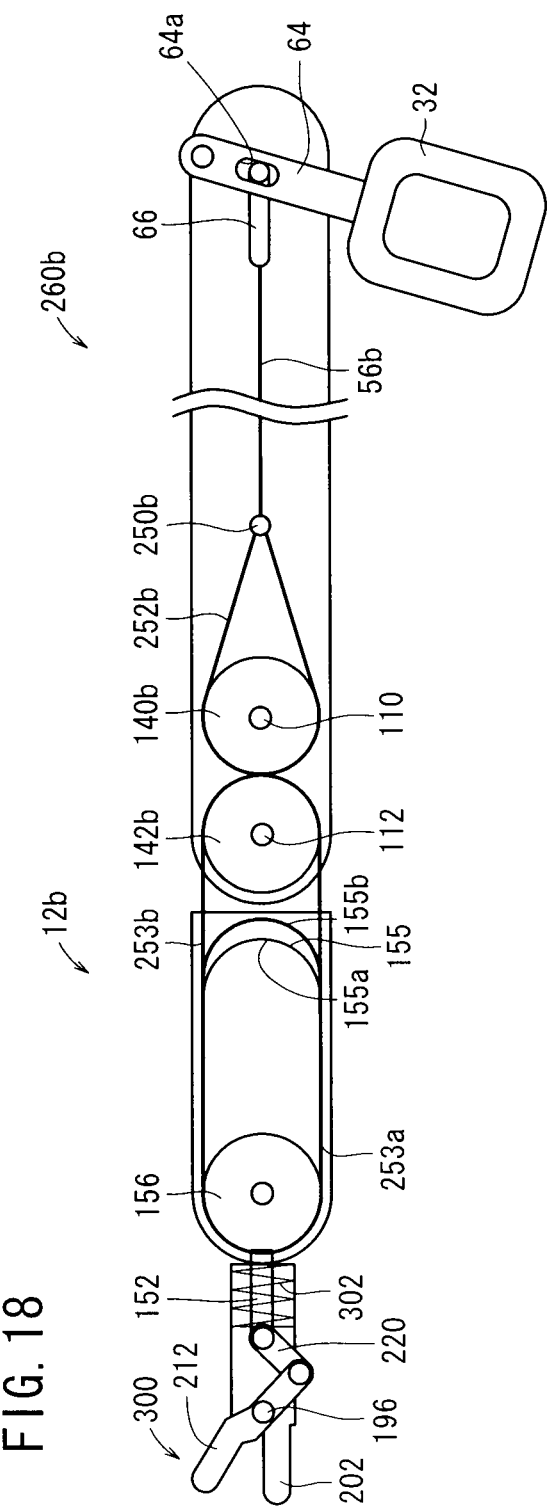
FIG. 18 is a schematic plan view of a distal-end working unit according to a modification.

FIG. 18 shows a distal-end working unit 12b according to a modification of the distal-end working unit 12a.

As shown in FIG. 18, the distal-end working unit 12b is similar to the distal-end working unit 12a (see FIG. 4), in that it has the second end effector drive mechanism 260b. However, the distal-end working unit 12b differs from the distal-end working unit 12a, in that it lacks the first end effector drive mechanism 260a. Parts of the distal-end working unit 12b, which are identical to those of the distal-end working unit 12a, are denoted by identical reference characters, and such features will not be described in detail below.

The distal-end working unit 12b has a single-acting type end effector 300, instead of the double-acting type end effector 104. The end effector 300 comprises a fixed gripper 202, a gripper 212 closable toward and openable away from the fixed gripper 202 about the pin 196, and a spring 312, which normally resiliently biases the transmitting member 152 to move in the Z1 direction. The gripper 212 can be closed toward and opened away from the fixed gripper 202 by the gripper link 220, which is actuated when the transmitting member 152 is displaced. More specifically, in FIG. 18, when the trigger lever 32 is pulled in the Z2 direction, the transmitting member 152 is displaced in the Z2 direction by the second end effector drive mechanism 260b, thereby turning the gripper 212 counterclockwise in order to close the end effector 300. Conversely, when the trigger lever 32 is opened, the transmitting member 152 is displaced in the Z1 direction under the resiliency of the spring 312 in order to return the end effector 300 to an open state. The trigger lever 32 also is returned in the Z1 direction.

In the distal-end working unit 12b, the return pulley 350 also is movable toward the concave surface 155a of the crescent driven member 155, which faces in the Z1 direction. Accordingly, the angle through which the gripper 212 is openable and closable can be maintained, and the transmitting member 152 along with the medical manipulator 10 overall can be reduced in size.

A distal-end working unit 12c according to another modification of the distal-end working unit 12a will be described below.

Initially, a first end effector drive mechanism 260a and a second end effector drive mechanism 260b, which are basic mechanisms for opening and closing the end effector 104 of the distal-end working unit 12c, will be described below.

Figure 19:
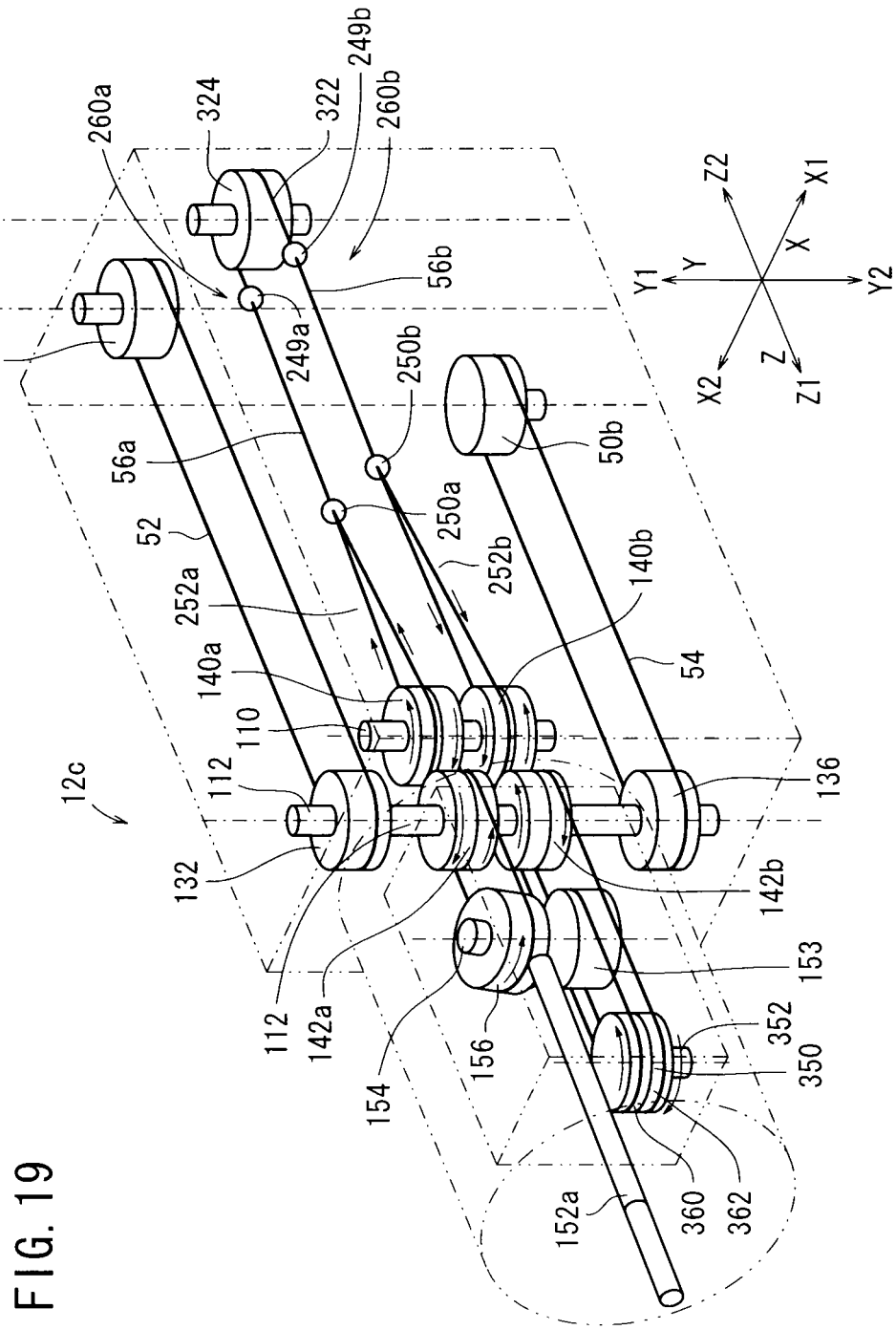
FIG. 19 is a schematic perspective view of a distal-end working unit according to another modification.
Figure 20:
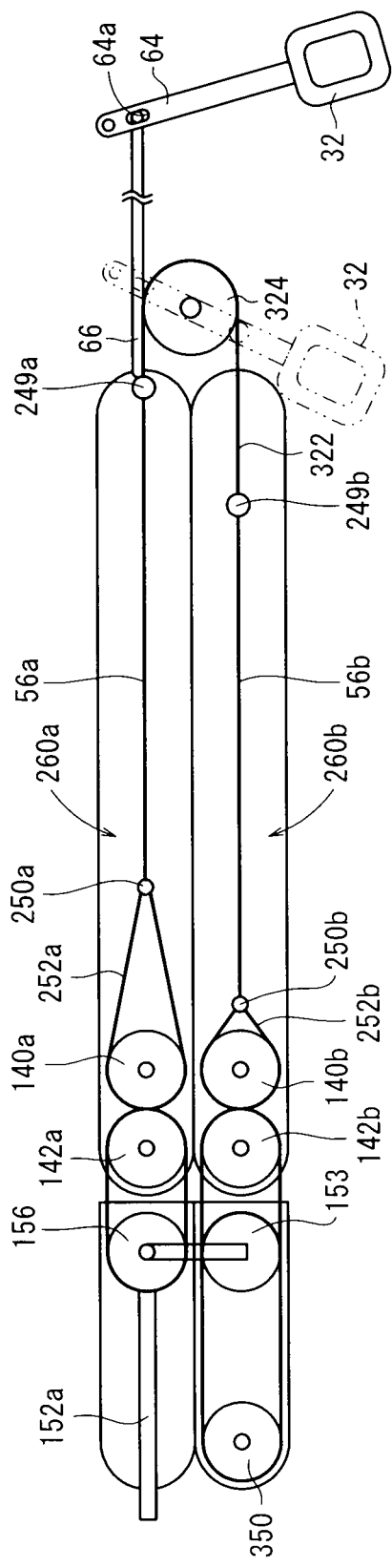
FIG. 20 is a schematic plan view of the distal-end working unit shown in FIG. 19.

As shown in FIGS. 19 and 20, the distal-end working unit 12c is substantially similar to the distal-end working unit 12a, having the first end effector drive mechanism 260a, which includes a transmitting member 152a, a wire (drive member) 56a, a driven wire 252a, an idle pulley 140a, a guide pulley 142a, and a driven pulley (cylindrical driven member) 156, and the second end effector drive mechanism 260b, which includes similar components, as will be described later.

Figure 21:
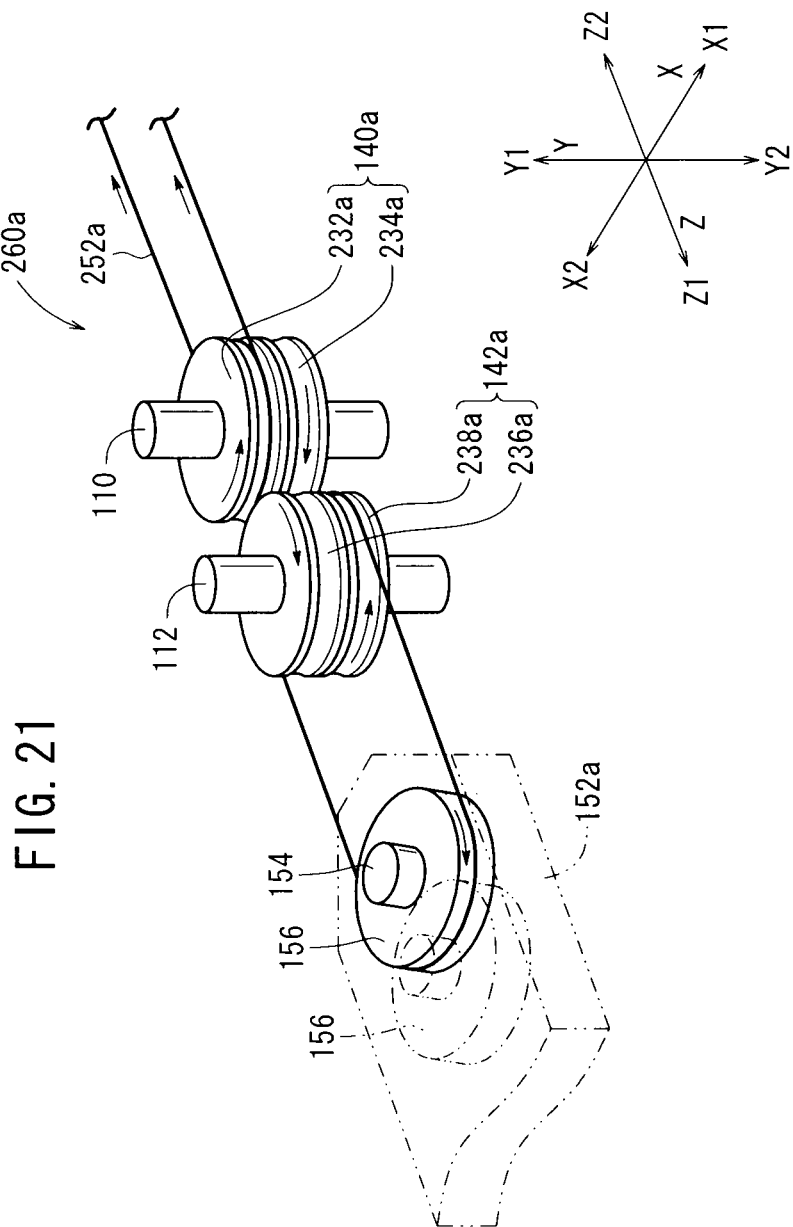
FIG. 21 is a perspective view showing a portion of a first end effector drive mechanism of the distal-end working unit shown in FIG. 19.

At one end in the Z2 direction in FIG. 23, one of the stretched sections of the driven wire 252a (hereinafter referred to as an outward stretched section 253a for distinguishing purposes) is in contact with surfaces of the first layer idle pulley 232*a* in the X1 and Z1 directions, then is in contact with surfaces of the first layer guide pulley 236*a* in the Z2 and X2 directions, and proceeds to the surface of the driven pulley 156 that faces in the X1 direction (see FIG. 21). Similarly, an outward stretched section 254*a* of the driven wire 252*b* proceeds to surfaces of a cylindrical driven member 153 and the return pulley 350 in the X2 direction, then is trained one half-turn around the surface of the return pulley 350 in the Z1 direction, proceeds to the surface of the cylindrical driven member 153 that faces in the X1 direction, is trained one half-turn around the surface of the cylindrical driven member 153 in the Z2 direction while extending obliquely in the Y2 direction, and finally reaches the surface of the cylindrical driven member 153 that faces in the X2 direction.

Figure 23:
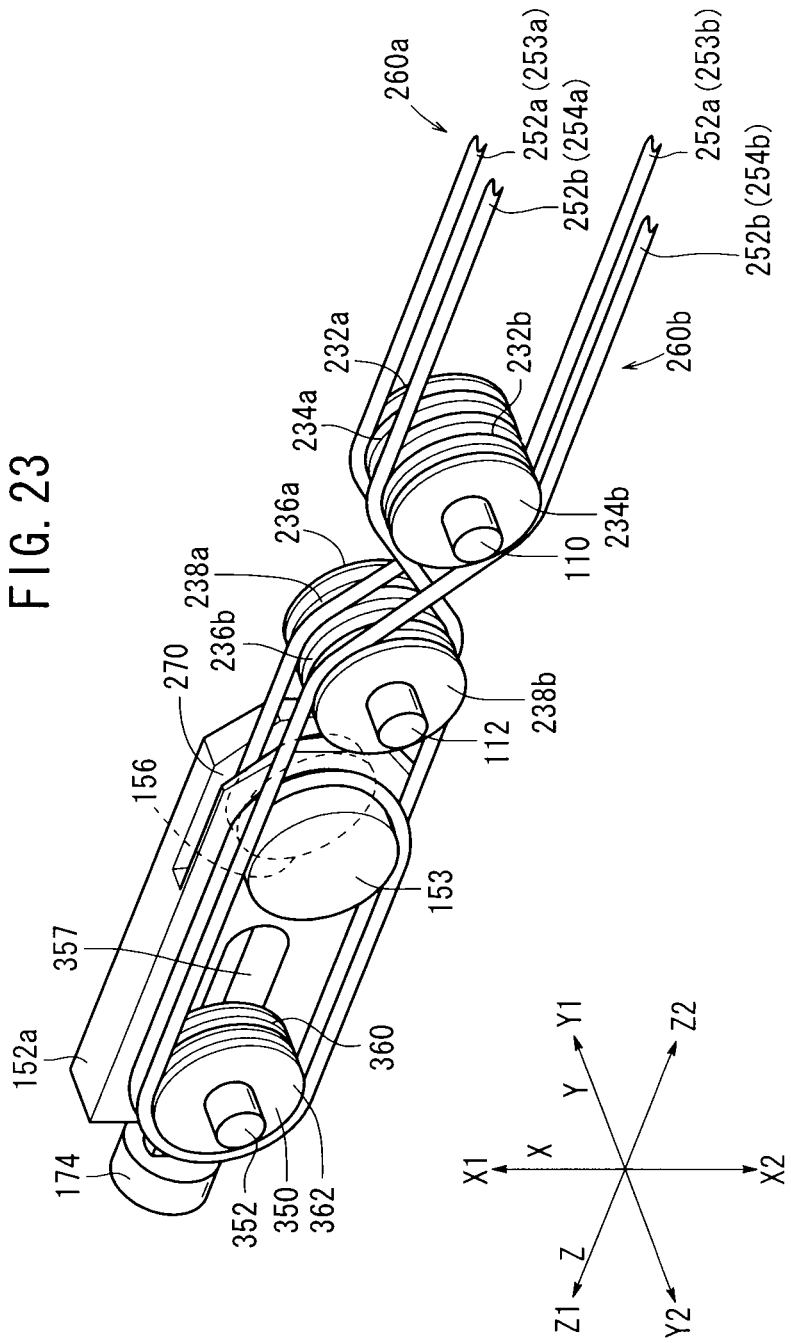
FIG. 23 is an enlarged perspective view of a first end effector drive mechanism and a second end effector drive mechanism of the distal-end working unit shown in FIG. 19.

At the end in the Z2 direction, as shown in FIG. 23, the other stretched section of the driven wire 252*a* (hereinafter referred to as an inward stretched section 253*b* for distinguishing purposes) is in contact with surfaces of the second layer idle pulley 234*a* in the X2 and Z1 directions, then is in contact with surfaces of the second layer guide pulley 238*a* in the Z2 and X1 directions, and proceeds to the surface of the driven pulley 156 that faces in the X1 direction. Similarly, an inward stretched section 254*b* of the driven wire 252*b* proceeds to surfaces of the cylindrical driven member 153 and the return pulley 350 in the X1 direction, then is trained one half-turn around the surface of the return pulley 350 in the X1 direction, is trained one half-turn around the surface of the return pulley 350 in the Z1 direction, and finally reaches the surface of the cylindrical driven member 153 that faces in the X2 direction.

The driven wire 252*a* thus passes through a circulatory path, having starting and ending points at the terminal 250*a*, which is positioned more closely to the proximal end than the idle pulley 140*a*. The driven wire 252*a* crosses over itself between the idle pulley 140*a* and the guide pulley 142*a*, thereby making up a substantially figure-8 configuration (see FIG. 19). The terminal 250*a* and the driven wire 252*a* are mechanically connected to the trigger lever 32 by the wire 56*a*.

The driven wire 252*a* crosses over itself between the idle pulley 140*a* and the guide pulley 142*a* as viewed in plan, and is displaced in the Y directions. Since the guide pulley 142*a* is constructed of the first layer guide pulley 236*a* and the second layer guide pulley 238*a*, the outward stretched section 253*a* and the inward stretched section 253*b* necessarily are displaced from each other in the Y directions.

Figure 22:
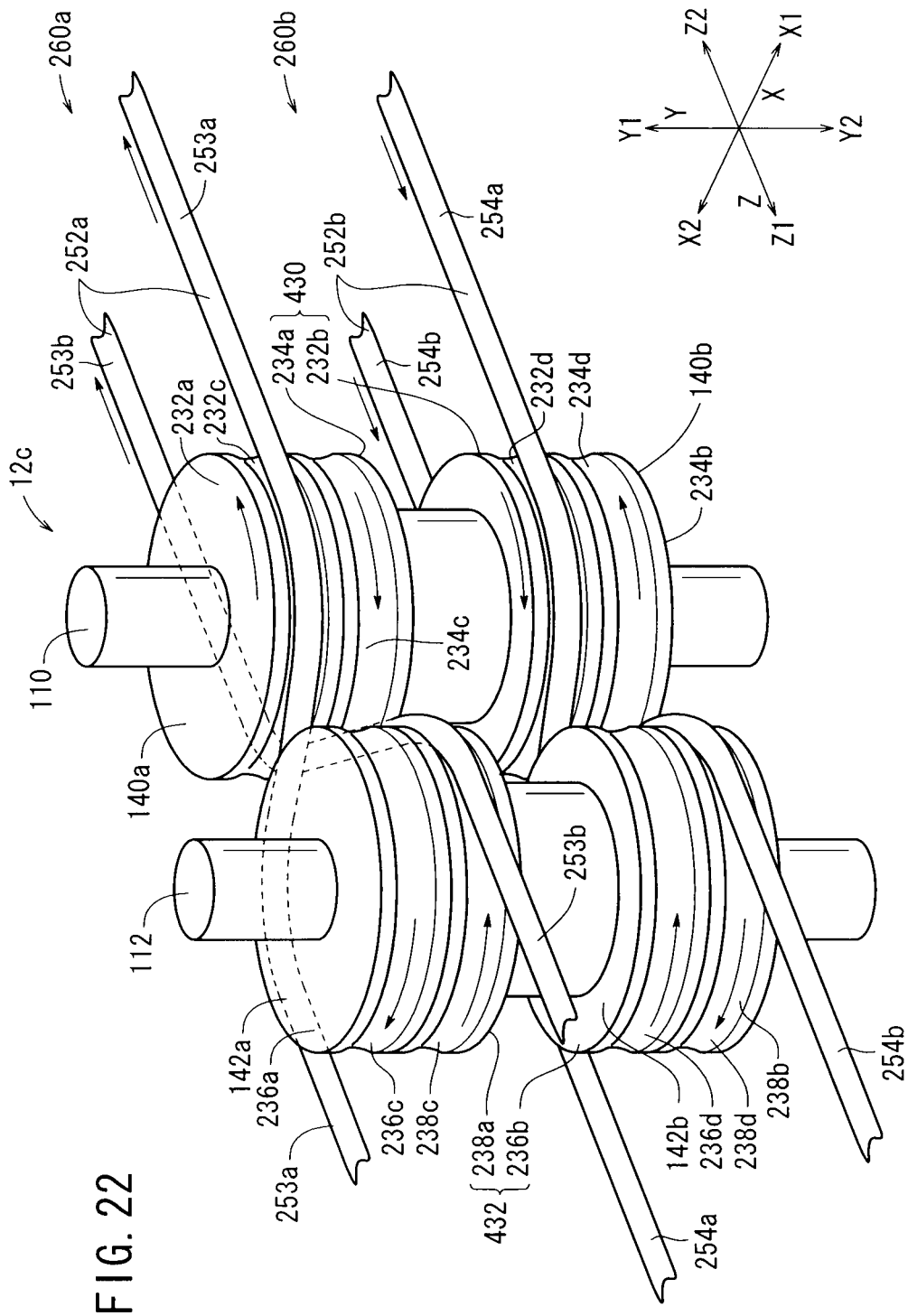
FIG. 22 is an enlarged perspective view of an idle pulley and a guide pulley of the distal-end working unit shown in FIG. 19.

As shown in FIG. 22, the outward stretched section 253*a* is displaced from the inward stretched section 253*b* by a distance Δ in the Y1 direction (see FIGS. 28 and 30), which is slightly greater than the diameter of the driven wire 252*a*. On the guide pulley 142*a*, the outward stretched section 253*a* extends from a position that is displaced by the distance Δ from the inward stretched section 253*b* in the Y1 direction toward the driven pulley 156 (see FIG. 30), which is spaced in the Z directions.

When the wire 56*a* (see FIG. 19) is pulled in the Z2 direction, the first layer idle pulley 232*a* and the second layer guide pulley 238*a* are rotated counterclockwise as viewed in plan, and the second layer idle pulley 234*a* and the first layer guide pulley 236*a* are rotated clockwise as viewed in plan. Since each of the idle pulley 140*a* and the guide pulley 142*a* comprises two parallel coaxial pulleys, the idle pulley 140*a* and the guide pulley 142*a* are rotatable in opposite directions when the driven wire 252*a*, which is held thereagainst, is moved, and hence the idle pulley 140*a* and the guide pulley 142*a* operate smoothly.

The second end effector drive mechanism 260*b* comprises a driven wire 252*b*, an idle pulley 140*b*, a guide pulley 142*b*, and a cylindrical driven member 153, which correspond respectively to the driven wire 252*a*, the idle pulley 140*a*, the guide pulley 142*a*, and the driven pulley 156 of the first end effector drive mechanism 260*a*. The second end effector drive mechanism 260*b* also includes a return pulley 350. The return pulley 350 is spaced from the cylindrical driven member 153 in the Z1 direction. The cylindrical driven member 153 has a reference axis that extends in the Y directions, and the driven pulley 156 is mounted on the transmitting member 152*a* obliquely to the Y directions, and is movable in the Z directions together with the transmitting member 152*a*. The return pulley 350 is movable in the Z directions relative to the transmitting member 152*a*. Structural details of the return pulley 350, the cylindrical driven member 153, the driven pulley 156, and the transmitting member 152*a* will be described later, with reference to FIGS. 28 through 30.

As shown in FIG. 23, the return pulley 350 comprises a first layer return pulley (first layer return cylindrical member) 360 which is displaced in the Y1 direction, and a second layer return pulley (second layer return cylindrical member) 362 which is displaced in the Y2 direction. The first and second layer return pulleys 360, 362 are aligned coaxially with each other. Similar to the first layer idle pulley 232*a*, etc., the first layer return pulley 360 and the second layer return pulley 362 may have a first layer return pulley groove 360*c* and a second layer return pulley groove 362*c* formed respectively in side surfaces thereof.

At the end in the Z2 direction in FIG. 23, one of the stretched sections of the driven wire 252*b* is in contact with surfaces of the first layer idle pulley 232*b* in the X1 and Z1 directions, then is in contact with surfaces of the first layer guide pulley 236*b* in the Z2 and X2 directions, and proceeds to the surface of the cylindrical driven member 153 that faces in the X2 direction. The driven wire 252*b* extends in the Z1 direction to the surface of the first layer return pulley 360 that faces in the X2 direction, then is trained one half-turn around the surface of the first layer return pulley 360 in the Z1 direction, and returns in the Z2 direction. The driven wire 252*b* extends in the Z2 direction to the surface of the cylindrical driven member 153 that faces in the X1 direction, is trained one half-turn around the surface of the cylindrical driven member 153 in the Z2 direction as the driven wire 252*b* extends obliquely in the Y2 direction, then returns in the Z1 direction and reaches the surface of the second layer return pulley 362 that faces in the X2 direction.

At one end in the Z2 direction in FIG. 23, the other stretched section of the driven wire 252*b* is in contact with surfaces of the second layer idle pulley 234*b* in the X2 and Z1 directions, then is in contact with surfaces of the second layer guide pulley 238*b* in the Z2 and X1 directions, and proceeds to the surface of the cylindrical driven member 153 that faces in the X1 direction. The driven wire 252*b* extends in the Z1 direction to the surface of the second layer return pulley 362 in the X1 direction, then is trained one half-turn around the surface of the second layer return pulley 362 in the Z1 direction, and finally reaches the surface of the second layer return pulley 362 that faces in the X2 direction. Similar to the driven wire 252*a*, the driven wire 252*b* thus passes through a circulatory path having starting and ending points at the terminal 250*b*, and is mechanically connected to the trigger lever 32 by the wire 56*b*.

With the above arrangement, the wire 56*a* and the wire 56*b* can easily be moved in opposite directions. When the trigger lever 32 is pulled, the terminal 249*a* also is pulled in unison therewith, thereby moving the transmitting member 152*a* in the Z2 direction. When the trigger lever 32 is pushed, the terminal 249b is pushed in unison therewith. Since the return pulley 350 is fixed in position, the cylindrical driven member 153 and the transmitting member 152a are moved in the Z1 direction. When the transmitting member 152a is moved back and forth, the end effector 104 is opened and closed.

The idle pulley 140a, the guide pulley 142a, the cylindrical driven member 153, the driven pulley 156, and the return pulley 350 are essentially of the same diameter, and are relatively large in diameter in layout, so that the driven wire 252a will not undergo sharp bends. The terminal 250a is disposed at a position appropriately spaced from the idle pulley 140a, so that the driven wire 252a will not be bent excessively. Both ends of the driven wire 252a form an acute angle at the terminal 250a. The idle pulley 140a and the guide pulley 142a are spaced from each other by a small gap, which is substantially the same as the width of the driven wire 252a, for example.

Overall structural details of the distal-end working unit 12c will be described below.

As shown in FIGS. 24, 25, 26 and 27, similar to the distal-end working unit 12a, the distal-end working unit 12c comprises a wire-driven mechanism 100, a composite mechanism 102, and the end effector 104. The distal-end working unit 12c incorporates therein mechanisms providing three degrees of freedom. These mechanisms include a mechanism having a first degree of freedom for turning a portion of the distal-end working unit 12c, which is positioned ahead of a first rotational axis Oy extending along the Y directions, in yawing directions about the first rotational axis Oy, a mechanism having a second degree of freedom for turning the portion of the distal-end working unit 12c in rolling directions about a second rotational axis Or, and a mechanism having a third degree of freedom for opening and closing the end effector 104 on the distal end of the distal-end working unit 12c about a third rotational axis Og.

When the wires 52, 54 are rotated, the gear bodies 126, 130 are rotated about the shaft 112 (see FIG. 19). When the gear bodies 126, 130 are rotated at the same speed and in the same direction, the gear body 146 swings with respect to the shaft 112 and moves in yawing directions. When the gear bodies 126, 130 are rotated at the same speed but in opposite directions, the gear body 146 is rotated about the second rotational axis Or and moves in rolling directions. When the gear bodies 126, 130 are rotated at different speeds, the gear body 146 makes a composite motion made up of both yawing and rolling directions. The gear body 126, the gear body 130, and the gear body 146 collectively make up a differential mechanism.

The mechanisms for actuating the distal-end working unit 12c about the yaw axis and the roll axis need not necessarily be operating mechanisms. Instead, the main shaft 144 may be integrally combined with a pulley for moving the distal-end working unit 12c about the yaw axis. Also, one pinion gear and one face gear may be combined with each other for moving the distal-end working unit 12c about the roll axis.

The main shaft 144 is rotatably supported on the shaft 112 between the gear body 126 and the guide pulley 142a, as well as between the guide pulley 142b and the gear body 130. The main shaft 144 has a sleeve that projects toward the composite mechanism 102. The main shaft 144 has a square hole 144a formed axially therein. The sleeve has a diametrical shaft hole 354 formed therein, with a pin 352 being inserted and fixed in the diametrical shaft hole 354. The pin 352 extends through the shaft hole 354 and is inserted (press-fitted) into an oblong hole 357 in the transmitting member 152a (see FIG. 28). The main shaft 144 includes two auxiliary plates 144b disposed on an end thereof in the Z2 direction, for holding both surfaces of the guide pulleys 142a, 142b in the Y directions. The auxiliary plates 144b have respective holes through which the shaft 112 extends. The auxiliary plates 144b are of a chevron shape, which widens progressively in the Z1 direction, for preventing foreign matter such as threads from entering therein.

Figure 24:
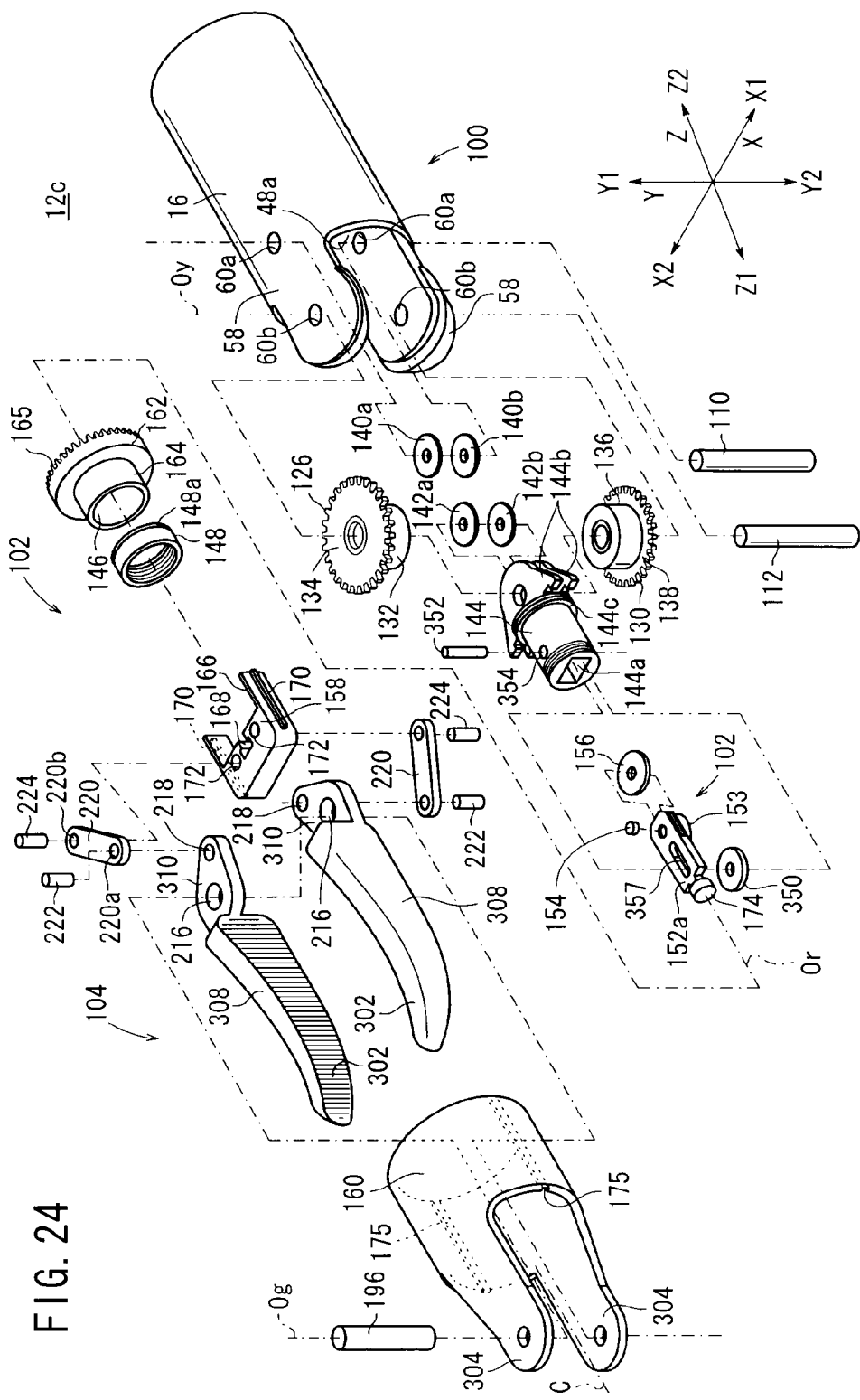
FIG. 24 is an exploded perspective view of the distal-end working unit shown in FIG. 19.
Figure 25:
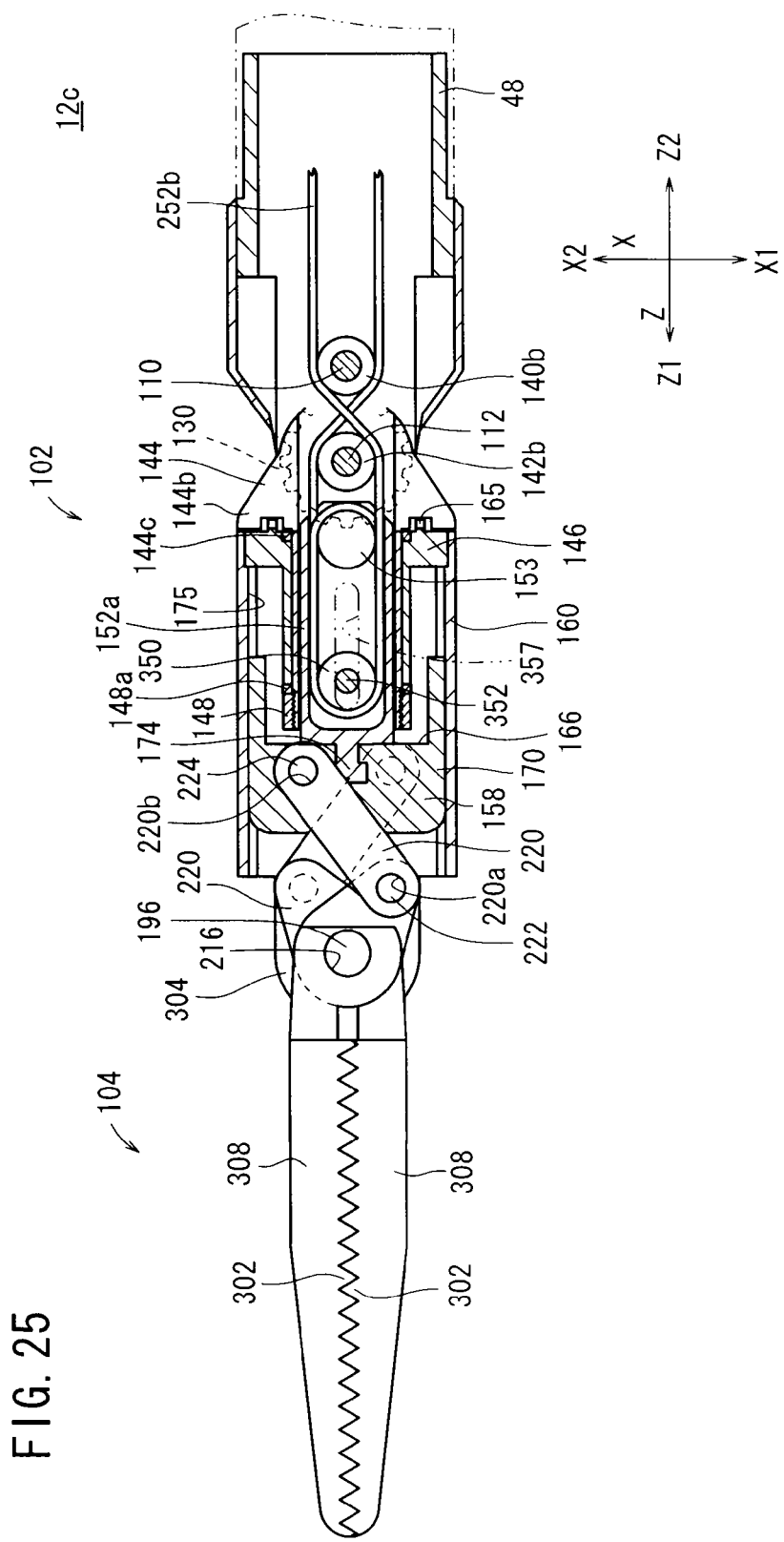
FIG. 25 is a sectional side elevational view of the distal-end working unit shown in FIG. 19 with a gripper being closed.
Figure 26:
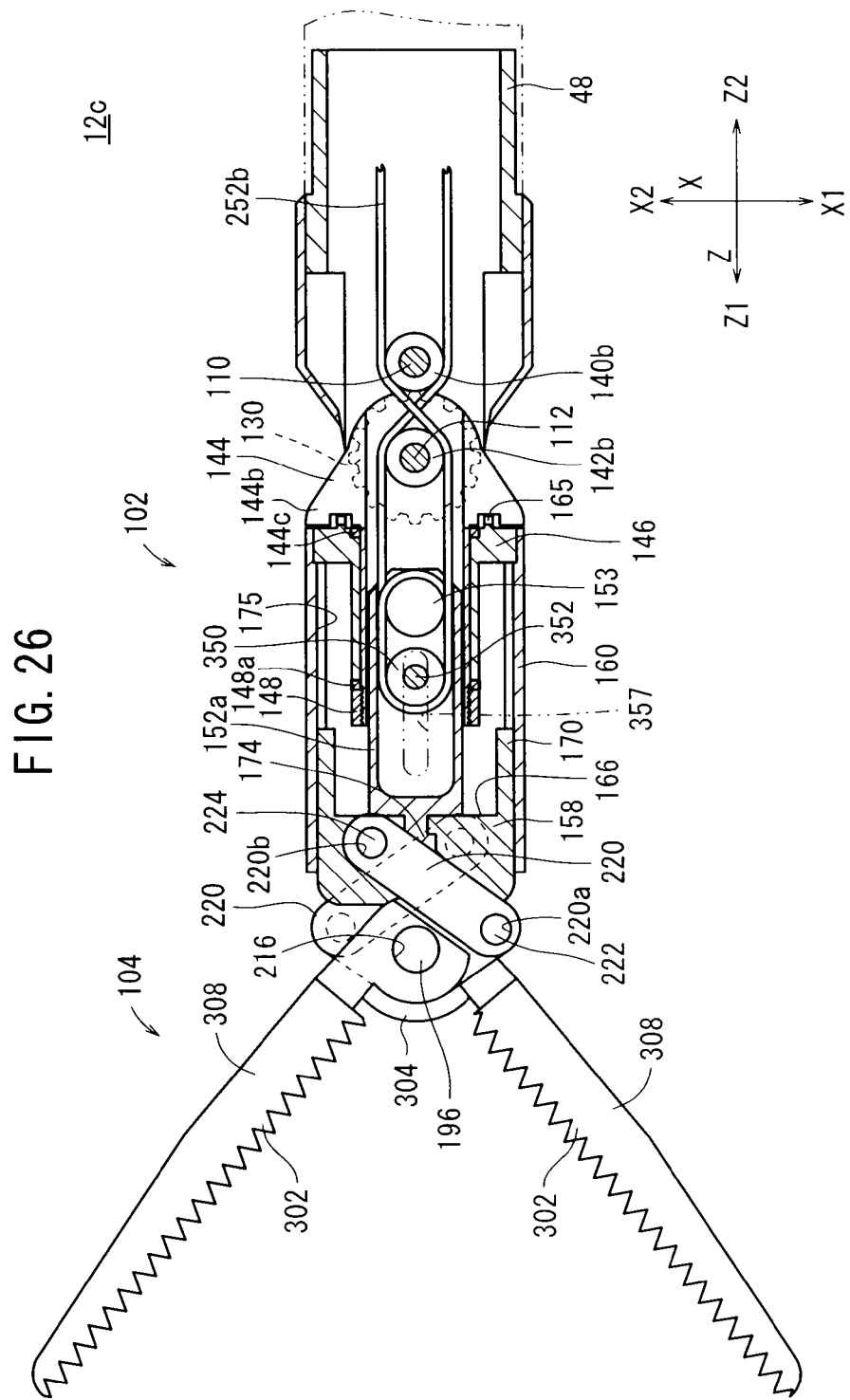
FIG. 26 is a sectional side elevational view of the distal-end working unit shown in FIG. 19 with the gripper being opened.
Figure 27:
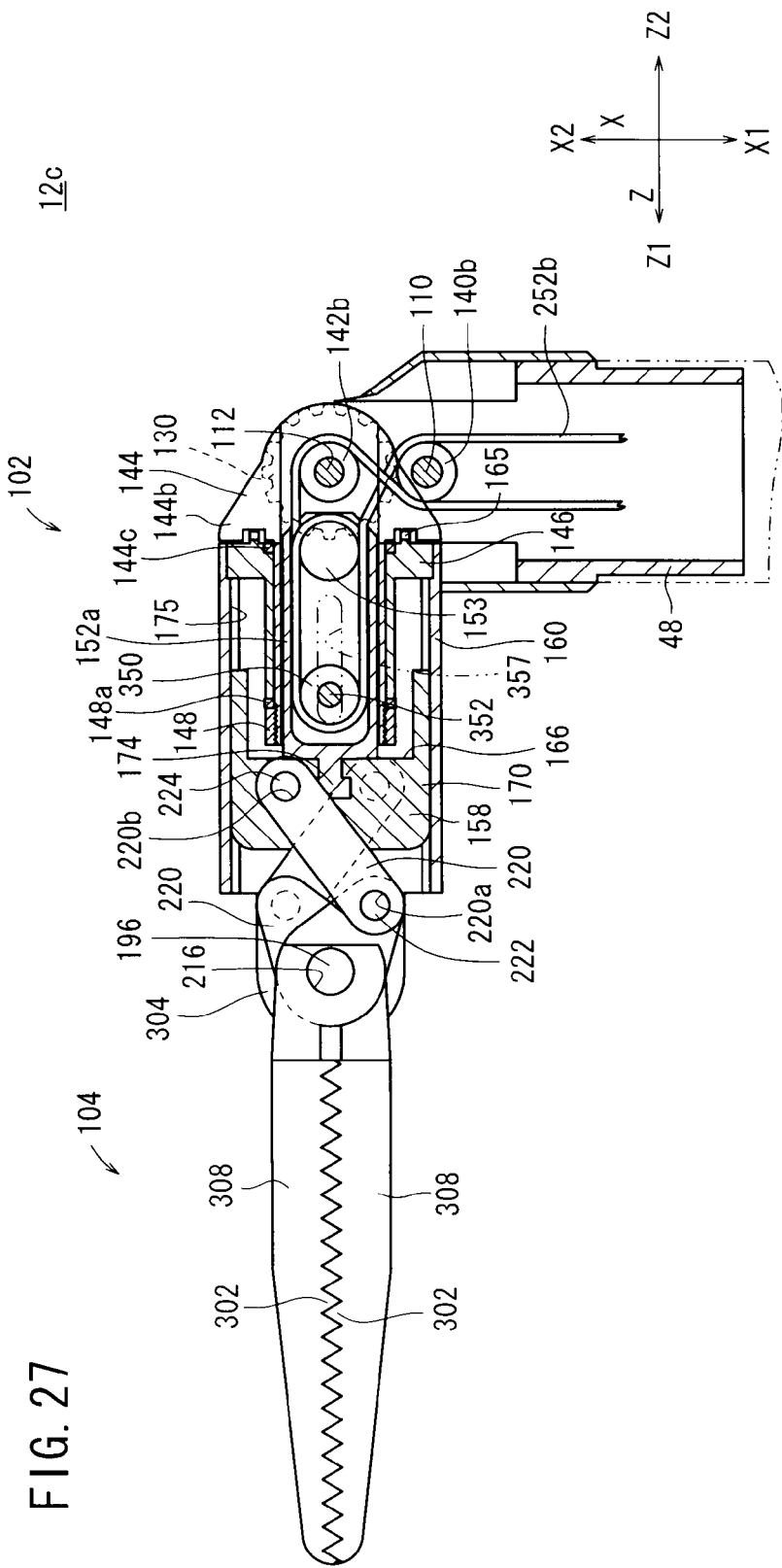
FIG. 27 is a sectional plan view of the distal-end working unit shown in FIG. 19, which is turned about a roll axis in one direction.

As shown in FIGS. 24 and 25, a thrust bearing 144c, which is made of resin, is disposed on a portion of the main shaft 144 that abuts against the gear body 146. A thrust bearing 148a, also made of resin, is disposed on a portion of the nut 148 that abuts against the gear body 146. The thrust bearings 144c, 148a are made of a material having a low coefficient of friction for reducing wear and torque on the abutting portions, and for preventing loads from being applied directly to the face gear 165. The thrust bearings 144c, 148a comprise slide bearings, but may also comprise roller bearings. When the end effector 104 is closed strongly or is opened, i.e., when the gear body 146 is strongly held in abutment with the main shaft 144, the distal-end working unit 12c can be turned smoothly about the roll axis. The shaft hole 354 extends across the hole 144a through the sleeve of the main shaft 144. The hole 144a is high enough to allow the transmitting member 152a, the cylindrical driven member 153, the driven pulley 156, and the return pulley 350 to be inserted therein.

The cover 160 is of a size large enough to cover the composite mechanism 102 substantially in its entirety, and serves to prevent foreign matter (living tissues, medications, threads, etc.) from entering into the composite mechanism 102 and the end effector 104. The cover 160 has two axial grooves 175 formed in an inner circumferential surface thereof, so as to diametrically face each other. The ribs 170 of the driven plate 158 are fitted respectively in the grooves 175 for axially guiding the driven plate 158. Since the knob 174 engages within the engaging cavity 168 of the driven plate 158, the cylindrical driven member 153 and the driven pulley 156 are axially movable back and forth in the hole 144a together with the driven plate 158 and the transmitting member 152a, and can roll about the transmitting member 152a. The cover 160 is fixed to the large-diameter portion 162 of the gear body 146 by means of threaded engagement, press-fitted engagement, or the like.

Structural details of the transmitting member 152a, the driven pulley 156 mounted on the transmitting member 152a, the cylindrical driven member 153, and the return pulley 350 will be described below.

Figure 28:
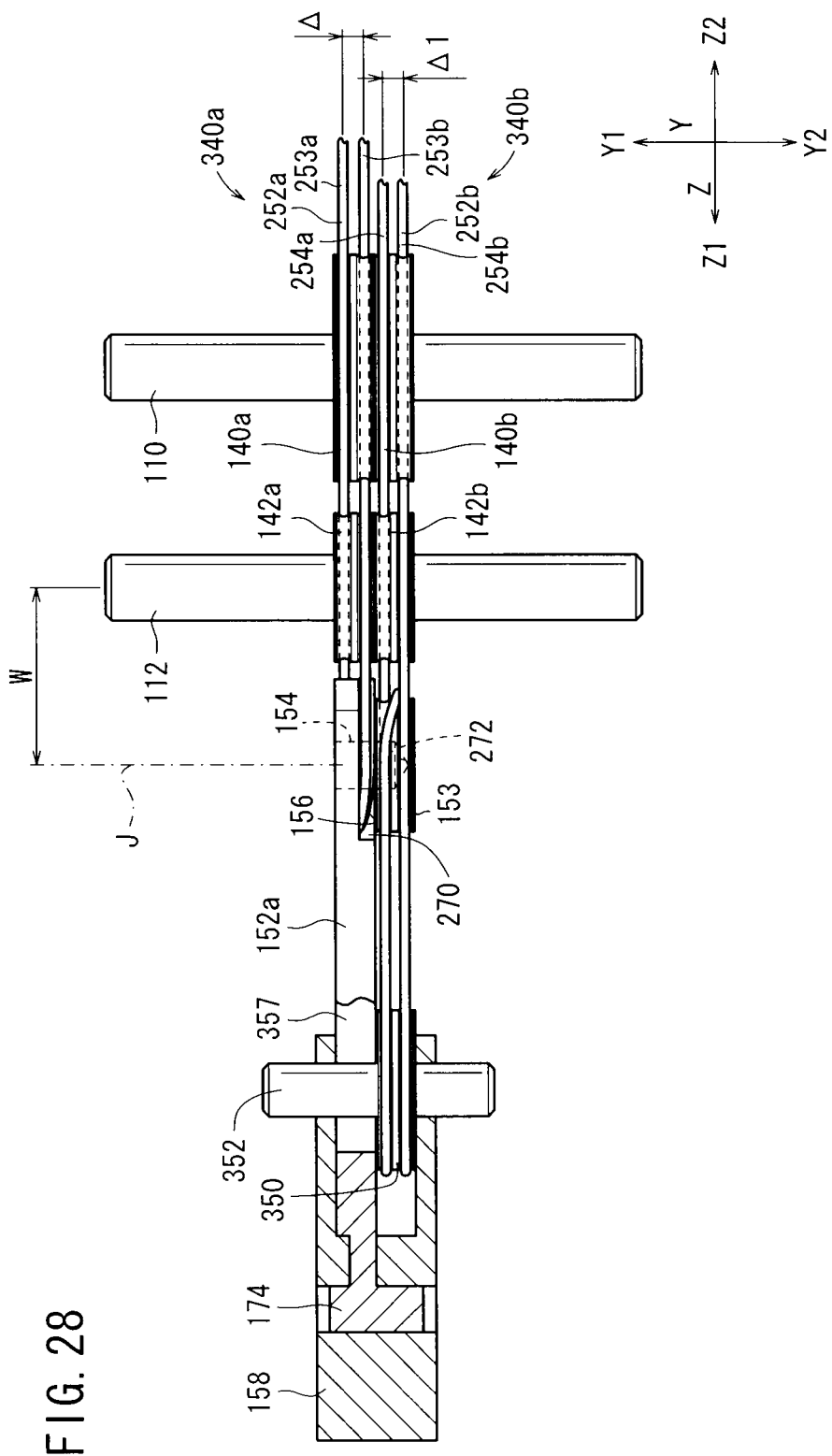
FIG. 28 is a side elevational view of the first end effector drive mechanism and the second end effector drive mechanism of the distal-end working unit shown in FIG. 19.

As shown in FIGS. 23 and 28, the transmitting member 152a is in the form of a plate, which is thin in the Y directions and elongated in the Z directions. The transmitting member 152a includes the pin 154, the cylindrical driven member 153, the driven pulley 156, the knob 174, the pin 352, and the oblong hole 357. The driven pulley 156 has a groove (a cylindrical driven member groove) 156c formed in a side surface thereof for circumferentially guiding the driven wire 252a.

The knob 174 is disposed on the end of the transmitting member 152 in the Z1 direction, and has a mushroom-shaped cylindrical distal end portion capable of engaging within the engaging cavity 168. When the mushroom-shaped knob 174 engages within the engaging cavity a68, the transmitting member 152a can transmit movements in the Z directions to the driven plate 158, while the driven plate 158 is capable of rotating about the roll axis.

The oblong hole 357 is formed substantially centrally in the transmitting member 152a. The oblong hole 357 is elongated in the Z directions and extends through the transmitting member 152a in the Y directions. The pin 352 extends through the oblong hole 357. The pin 352 is press-fitted into the shaft hole 354 in the sleeve of the main shaft 144 (see FIG. 24), and the return pulley 350 is rotatably supported on the pin 352. The return pulley 350 is in contact with a side surface of the transmitting member 152a that faces in the Y2 direction, and is rotatably supported on the pin 352 in the hole 144a of the main shaft 144. The pin 352 and the return pulley 350 are thus fixed in position.

The cylindrical driven member 153 is integral with the transmitting member 152a and projects from the side surface of the transmitting member 152a, which faces in the Y2 direction near the end thereof in the Z2 direction. The cylindrical driven member 153 has a width large enough to support two turns of the driven wire 252b. Unlike the driven pulley 156, the cylindrical driven member 153 is not rotatable, because the driven wire 252b that is in contact with the cylindrical driven member 153 essentially does not move under strong frictional forces between the driven wire 252b and the cylindrical driven member 153. In other words, strong frictional forces are applied to the cylindrical driven member 153 when the end effector 104 is opened, however, the distal-end working unit 12c is rarely turned about the yaw axis while the end effector 104 is open.

Figure 29:
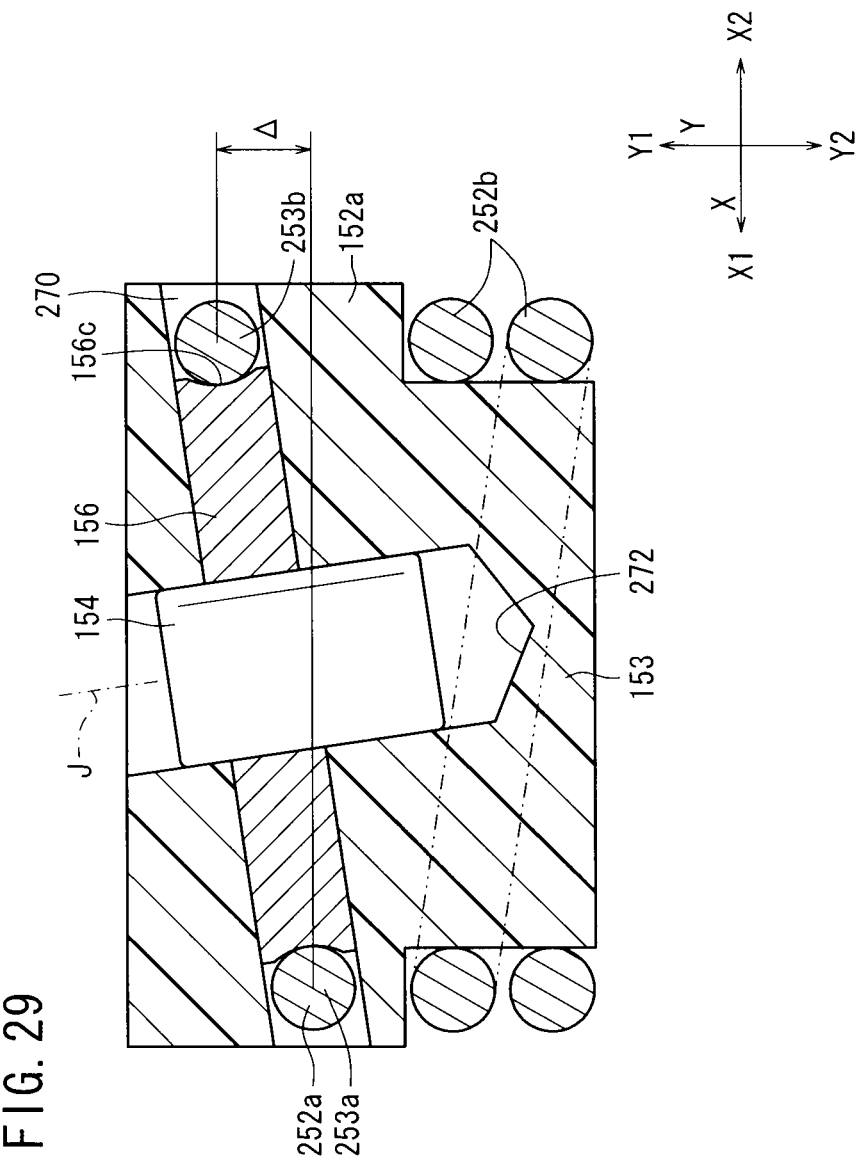
FIG. 29 is a cross-sectional view of the transmitting member of the distal-end working unit shown in FIG. 19, as viewed in a Z2 direction.

As shown in FIGS. 28 and 29, the transmitting member 152a comprises the pulley groove 270, which is formed in one end thereof in the Z directions and in which the driven pulley 156 is disposed, and the pin 154 on which the driven pulley 156 is rotatably supported in the pulley groove 270. The pin 154 is press-fitted into an oblique hole 272. The pulley groove 270 is slightly wider than the driven pulley 156, and the pulley groove 270 opens on the surface of the transmitting member 152, which faces in the Z2 direction, so that the driven wire 272a can pass therethrough. The pulley groove 270 extends slightly obliquely to the X directions from the surface of the transmitting member 152a, which faces in the X1 direction, toward the surface of the transmitting member 152a, which faces in the X2 direction. Since, as shown in FIG. 29, the pulley groove 270 is narrow, the driven wire 252a does not drop off from the circumferential surface of the driven pulley 156. Due to the groove 156c of the driven pulley 156, the driven wire 252a is kept out of sliding contact with the wall surface of the pulley groove 270, and is held stably in position.

The oblique hole 272 and the pin 154 are oriented in a direction perpendicular to upper and lower surfaces of the pulley groove 270, and are inclined in an XY plane to the Y-direction axis (or stated otherwise, the direction of the shaft 112 on which the guide pulley 142a is rotatably supported). The oblique hole 272 consists of a bottomed hole, which opens only on the surface that faces in the Y1 direction. However, the oblique hole 272 may comprise a through hole. Further, depending on design conditions, the cylindrical driven member 153 may be a rotatable member. However, since the cylindrical driven member 153 needs to be rotated about the Y-direction axis, it is difficult for the pin 154, which extends in alignment with an object axis J, to be used as a shaft on which the cylindrical driven member 153 is rotatably supported. Inasmuch as the driven wire 252b, which is in contact with the cylindrical driven member 153, essentially does not move under strong frictional forces applied between the driven wire 252b and the cylindrical driven member 153, it is desirable for the cylindrical driven member 153 to be integral with the transmitting member 152a.

As shown in FIG. 29, which shows the transmitting member 152a as viewed from the Z2 direction, the axis J of the pin 154 is slightly inclined counterclockwise, and the pin 154 and the driven pulley 156 also are inclined accordingly. Therefore, the end face of the driven pulley 156 that faces in the X1 direction is shifted, by a distance Δ, more toward the Y2 direction than the end face of the driven pulley 156 that faces in the X2 direction. The distance Δ represents a difference in the Y directions between the outward stretched section 253a and the inward stretched section 253b of the driven wire 252a around the cylindrical guide member 142a. Stated otherwise, opposite end faces in the X directions of the driven pulley 156 and around which the driven wire 252a is trained are displaced from each other in the Y directions, i.e., in axial directions of the cylindrical guide member 142a, by the distance Δ.

Figure 30:
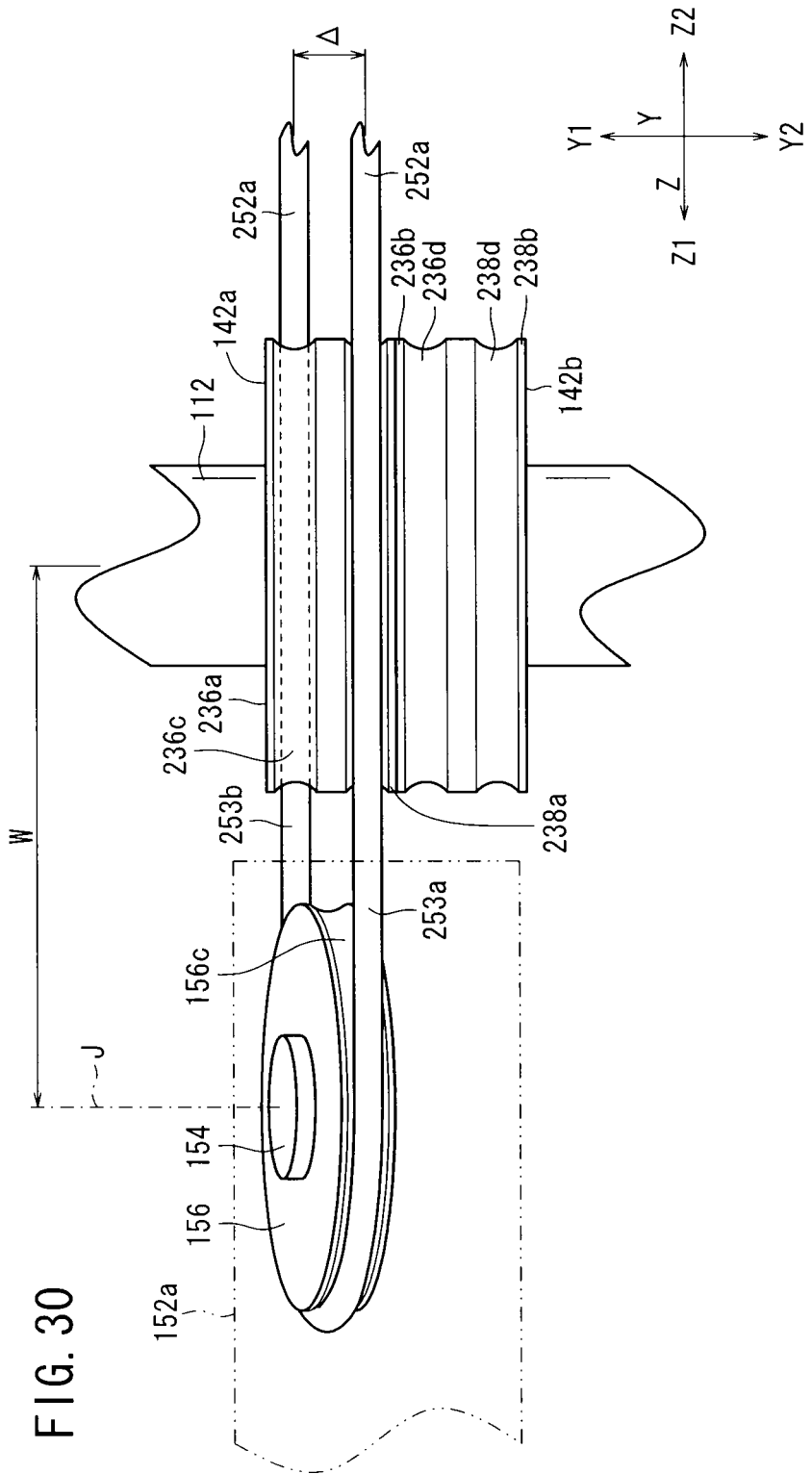
FIG. 30 is an enlarged fragmentary side elevational view of the first end effector drive mechanism of the distal-end working unit shown in FIG. 19.

As shown in FIG. 30, the outward stretched section 253a extends straightly in the Z1 direction from the second layer guide pulley 238a of the guide pulley 142a toward the surface of the driven pulley 156 in the X1 direction, and the inward stretched section 253b extends straightly in the Z1 direction from the first layer guide pulley 236a of the guide pulley 142a toward the surface of the driven pulley 156 in the X2 direction. Therefore, the outward stretched section 253a and the inward stretched section 253b are held out of contact with end walls of the pulley groove 270 of the transmitting member 152a, and are guided straightly into the groove 156c of the driven pulley 156 along the direction in which the groove 156c extends, without abutting against any corners of the driven pulley 156. The driven wire 252a, which is made up of the outward stretched section 253a and the inward stretched section 253b, is trained one half-turn around the driven pulley 156, since the height of the driven wire 252a in the Y directions is changed by the distance Δ, and the driven wire 252a travels back without being held in sliding contact with any corners of the driven pulley 156.

If the axis J were oriented in the Y directions, with the pulley groove 270 lying parallel to an XZ plane and while the driven pulley 156 rotates in the XZ plane, then the driven wire 252a would be held in abutment with respective corners, including the wall end of the pulley groove 270 in the Z2 direction, the walls of the groove 156c of the driven pulley 156, and the walls of the groove 236c of the guide pulley 142a. Since the medical manipulator 10 is used in laparoscopic surgery, the distal-end working unit 12c is very small, and the distance W between the shaft 112 and the axis J is small, as shown in FIGS. 28 and 30. When the transmitting member 152a, which is displaceable in the Z directions, is displaced a maximum distance in the Z2 direction, the distance W is considerably small, thereby increasing the angle through which the driven wire 252a is inclined, and hence the angles by which the driven wire 252a abuts against the above corners. Consequently, when the driven wire 252a is actuated, the driven wire 252a is held in sliding contact with such corners and could possibly become worn or damaged.

With the medical manipulator 10 according to the present embodiment, the axis J of the pin 154 does not lie parallel to the shaft 112 on which the guide pulley 142a is rotatably supported. Also, the outward stretched section 253a and the inward stretched section 253b of the driven wire 252a extend straight in the Z directions between the guide pulley 142a and the driven pulley 156. Consequently, the driven wire 252a is not held under friction in sliding contact with the corners, and hence the driven wire 252a does not become worn or damaged. Accordingly, the driven wire 252a, the driven pulley 156, and the transmitting member 152a have a long service life.

The medical manipulator 10 according to the present embodiment is particularly effective when the distal-end working unit 12c is turned about the yaw axis while the end effector 104 grips an object. When the distal-end working unit 12c is turned about the yaw axis while the end effector 104 grips an object, the driven wire 252a basically is not moved.

The driven pulley 156 is rotated while the driven wire 252a is kept under high tension, and the driven wire 252a is moved relatively to the guide pulley 142a. If the axis J were oriented in the Y directions, with the pulley groove 270 lying parallel to the XZ plane, and the driven pulley 156 were rotated in the XZ plane, then since the driven wire 252a is held in abutment with respective corners, including the wall end of the pulley groove 270 in the Z2 direction, the walls of the groove 156c of the driven pulley 156, and the walls of the groove 236c of the guide pulley 142a, the driven wire 252a is held in sliding contact with such corners and could possibly become worn or damaged.

As shown in FIG. 28, the driven wire 252b is wound around the side surface of the cylindrical driven member 153 in the Z2 direction, while being shifted by a distance Δ1 in the Y directions. The distance Δ1 represents a difference in the Y directions between the outward stretched section 254a and the inward stretched section 254b of the driven wire 252b around the guide pulley 142b. Although similar to the driven wire 252a, the driven wire 252b is basically not moved, the driven wire 252b is moved relatively to the cylindrical driven member 153. However, since the distal-end working unit 12c is not turned about the yaw axis while the driven wire 252b is kept under high tension, i.e., while the driven wire 252b is pushed strongly in a direction to open the end effector 104, the driven wire 252b will not become worn or damaged even if the driven wire 252b is slidingly moved. Accordingly, unlike the driven pulley 156, the cylindrical driven member 153 does not need to have the axis thereof inclined, and the cylindrical driven member 153 may be combined integrally with the transmitting member 152a.

Figure 31:
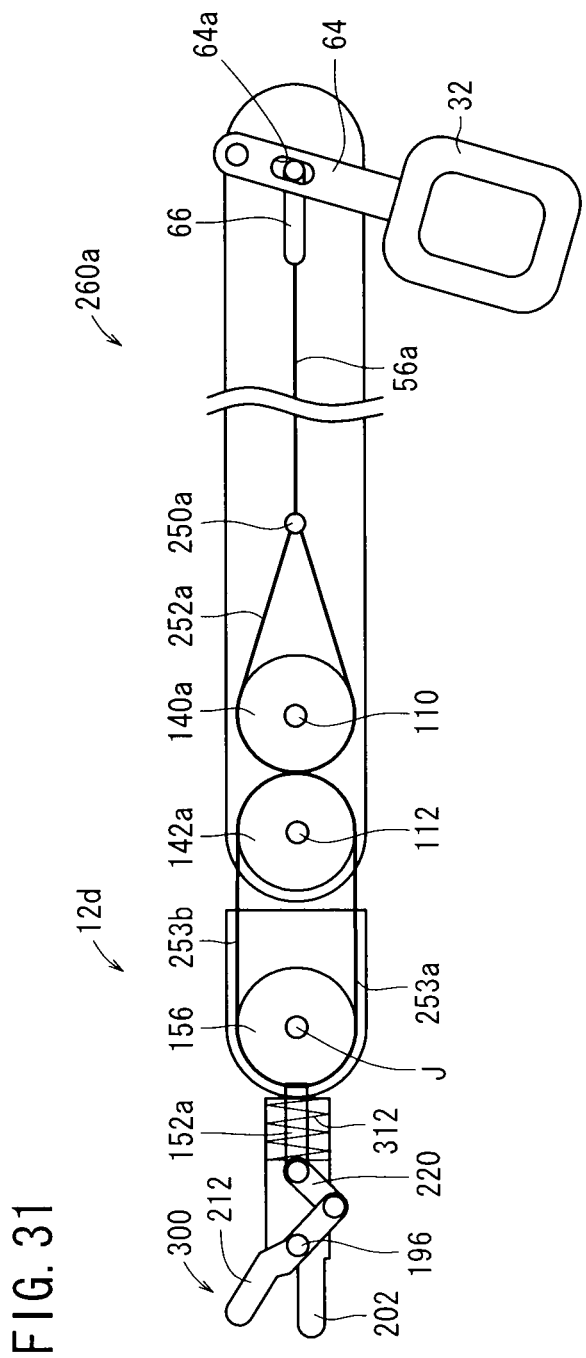
FIG. 31 is a plan view of a distal-end working unit according to a modification of the distal-end working unit shown in FIG. 19.

FIG. 31 shows a distal-end working unit 12d, which constitutes a modification of the distal-end working unit 12c.

As shown in FIG. 31, the distal-end working unit 12d is similar to the distal-end working unit 12c (see FIG. 20), in that it includes the first end effector drive mechanism 260a. However, the distal-end working unit 12d differs from the distal-end working unit 12c, in that it lacks the second end effector drive mechanism 260b. Parts of the distal-end working unit 12d which are identical to those of the distal-end working unit 12c are denoted by identical reference characters, and such features will not be described in detail below.

The distal-end working unit 12d has a single-acting type end effector 300, instead of the double-acting type end effector 104. The end effector 300 comprises a fixed gripper 202, a gripper 212 closable toward and openable away from the fixed gripper 202 about the pin 196, and a spring 312, which normally resiliently biases the transmitting member 152a to move in the Z1 direction. The gripper 212 can be closed toward or opened away from the fixed gripper 202 by the gripper link 220, which is actuated when the transmitting member 152a is displaced. More specifically, when the trigger lever 32 is pulled in the Z2 direction, the transmitting member 152a is displaced in the Z2 direction by the first end effector drive mechanism 260a, thereby turning the gripper 212 counterclockwise in FIG. 31 to close the end effector 300. When the trigger lever 32 is opened, the transmitting member 152a is displaced in the Z1 direction under the resiliency of the spring 312 in order to return the end effector 300 to an open state. The trigger lever 32 also is returned in the Z1 direction.

With the distal-end working unit 12d, the axis J of the driven pulley 156 is oblique to the shaft 112 of the guide pulley 152a. The outward stretched section 253a and the inward stretched section 253b extend straightly in the Z directions between the driven pulley 156 and the guide pulley 142a, and are held out of sliding contact with the corners, including the walls of the groove 156c of the driven pulley 156.

Figure 32:
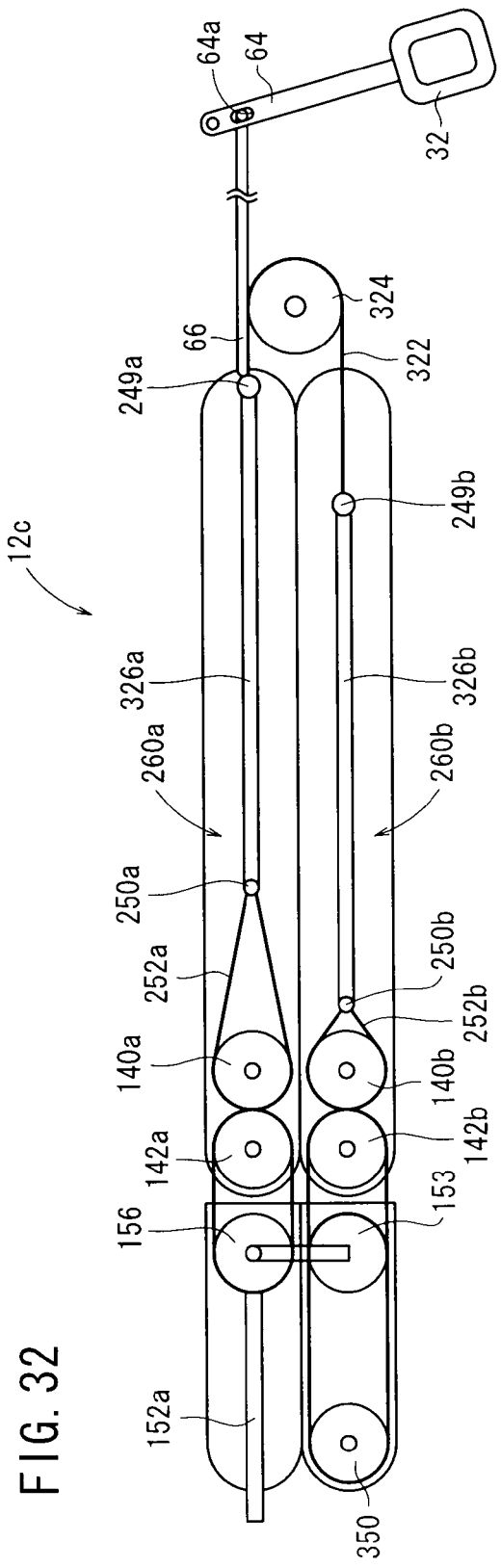
FIG. 32 is a plan view of the distal-end working unit shown in FIG. 19, which incorporates straight-motion rods therein.

The wires 56a, 56b (see FIG. 20) of the first end effector drive mechanism 260a and the second end effector drive mechanism 260b may be replaced with straight-motion rods 326a, 326b, as shown in FIG. 32. Since rods are generally more rigid than wires, portions thereof that make only straight motions can produce large gripping forces, and can provide a long service life.

The drive joint pulley 324 around which the drive joint wire 322 is trained may be dispensed with, and the wires 56a, 56b and the straight-motion rods 326a, 326b shown in FIG. 32 may be connected directly to the trigger lever 32. The wires 56a, 56b and the straight-motion rods 326a, 326b shown in FIG. 32 may include, at some location thereon, a load limiter for preventing excessive loads from being applied.

Figure 33:
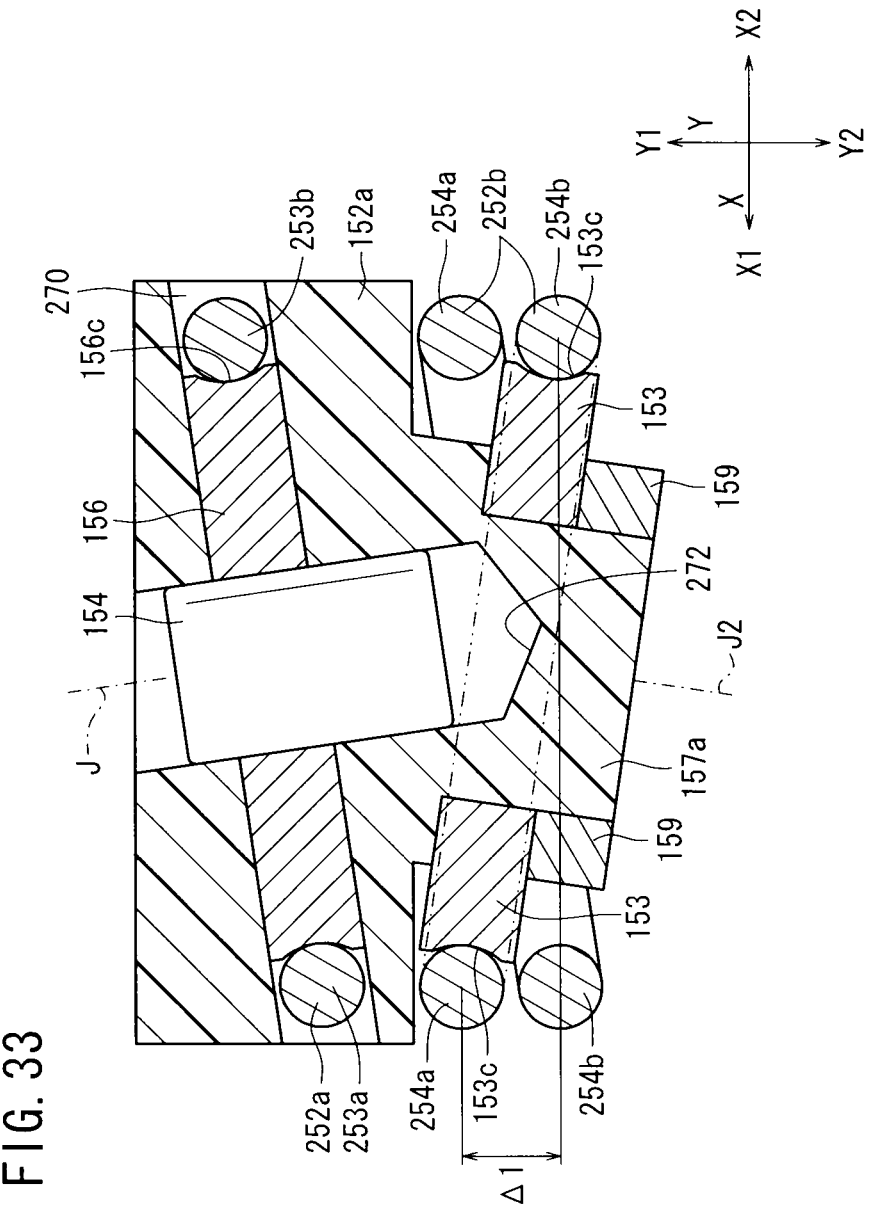
FIG. 33 is a cross-sectional view of the transmitting member of a modification of the distal-end working unit shown in FIG. 19, as viewed in the Z2 direction.

With the distal-end working units 12c, 12d, as shown in FIG. 33, the cylindrical driven member 153 may be in contact with a side surface of the transmitting member 152a near the end thereof in the Z2 direction, and may be rotatably supported on a pin 157a, which is combined integrally with the transmitting member 152a. FIG. 33 shows the transmitting member 152a as viewed from the Z2 direction. In FIG. 33, the axis J2 of the pin 157a is slightly inclined clockwise, and the pin 157a and the cylindrical driven member 153 also are inclined accordingly. The cylindrical driven member 153 has a width large enough to support one turn of the driven wire 252b, and is prevented from being removed from the pin 157a by a retainer 159. The end face of the cylindrical driven member 153 that faces in the X1 direction is shifted in the Y1 direction from the end face of the cylindrical driven member 153 that faces in the X2 direction, by a distance Δ1, which is the same as the distance Δ1 shown in FIG. 28. The distance Δ1 represents a difference in the Y directions between the outward stretched section 254a and the inward stretched section 254b of the driven wire 252b around the guide pulley 142b (see FIG. 28). Stated otherwise, as shown in FIG. 33, the opposite end faces in the X directions of the cylindrical driven member 153 around which the driven wire 252b is trained are displaced from each other by the distance Δ1 in the Y direction, i.e., the axial direction of the guide pulley (cylindrical guide member) 142b. The cylindrical driven member 153 may have a groove 153c therein, similar to the driven pulley 156, etc. This arrangement makes it possible to reduce wear and damage on the driven wire 252b caused by frictional sliding motion thereof when the distal-end working unit 12d is turned around the yaw axis and while the driven wire 252b is kept under high tension, i.e., while the driven wire 252b is pushed strongly in a direction to open the end effector 104, e.g., in infrequent cases where the end effector 104 changes its orientation while spreading apart a living tissue.

Figure 34:
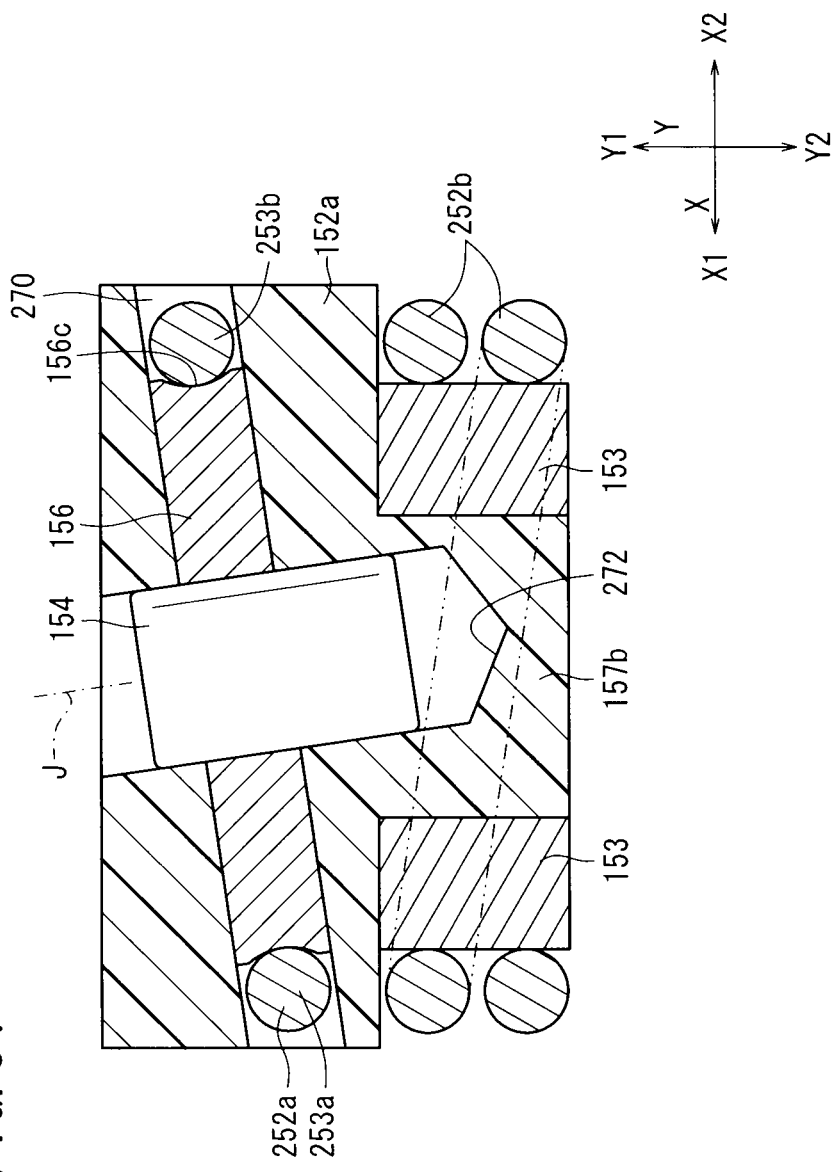
FIG. 34 is a cross-sectional view of the transmitting member of another modification of the distal-end working unit shown in FIG. 19, as viewed in the Z2 direction.

With the distal-end working units 12c and 12d, as shown in FIG. 34, the cylindrical driven member 153 may be in contact with the side surface of the transmitting member 152a near an end thereof in the Z2 direction, and may be rotatably supported on a pin 157b, which is combined integrally with the transmitting member 152a and extends in the Y directions. The cylindrical driven member 153 has a width large enough to support two turns of the driven wire 252b. This arrangement makes it possible to reduce wear and damage to the driven wire 252b caused by frictional sliding movement thereof, and the arrangement is simpler in structure than the modification shown in FIG. 33.

Figure 35:
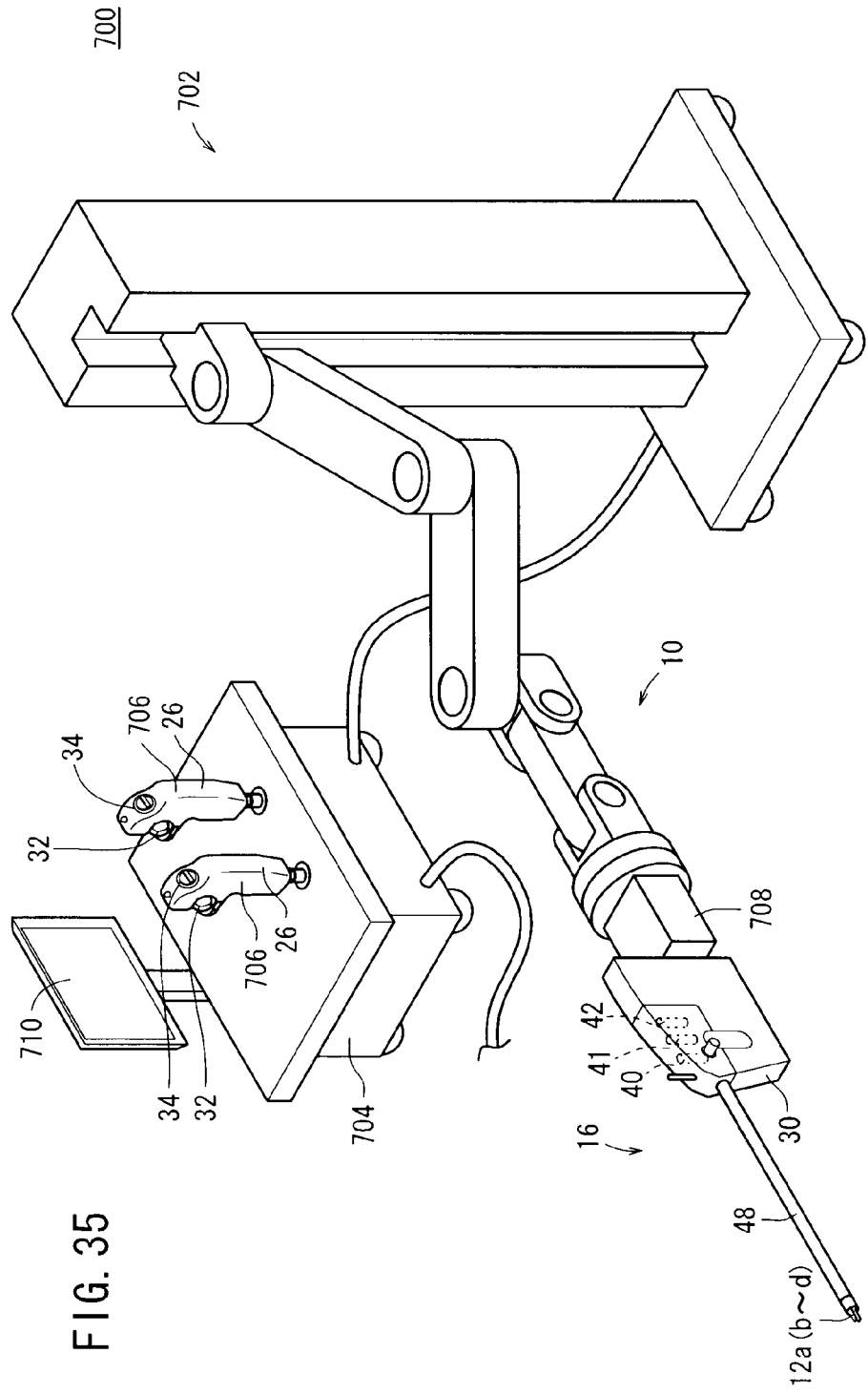
FIG. 35 is a schematic perspective view of a surgical robot system with a working unit connected to the distal end of a robot arm.

The medical manipulator 10 may be applied to a surgical robot system 700 as shown in FIG. 35, for example.

As shown in FIG. 35, the surgical robot system 700 has an articulated robot arm 702 and a console 704, with the working unit 16 connected to the distal end of the robot arm 702. The distal end of the robot arm 702 incorporates therein a mechanism which functions the same as the medical manipulator 10. The robot arm 702 may constitute a means for moving the working unit 16, and is not limited to an installed type, but may be an autonomous movable type. The console 704 may be a table type, a control panel type, or the like.

The robot arm 702 should preferably have six or more independent joints (rotary shafts, slide shafts, etc.) for setting the position and orientation of the working unit 16 as desired. The medical manipulator 10 on the distal end of the robot arm 702 is integrally combined with the distal end 708 of the robot arm 702. The medical manipulator 10 includes a motor (an actuator operatively coupled to a manually operated input unit) 42 instead of the trigger lever 32. The motor 42 actuates the wires 56a, 56b.

The robot arm 702 operates under the control of the console 704, and may be actuated automatically according to a program, or by joysticks 706 mounted on the console 704, or by a combination of a program and the joysticks 706. The working unit 16 includes the distal-end working unit 12 described above.

The console 704 includes the two joysticks 706 that serve as an operation commander, and a monitor 710. Although not shown, the two joysticks 706 are capable of individually operating two robot arms 702. The two joysticks 706 are disposed in respective positions where they can easily be operated by both hands of the operator. The monitor 710 displays information such as an image produced by a flexible scope.

The joysticks 706 can be moved vertically and horizontally, twisted, and tilted, whereby the robot arm 702 can be moved depending on movements of the joysticks 706. The joysticks 706 may serve as master arms. The robot arm 702 and the console 704 may be connected to each other by a communicating means, such as a wired link, a wireless link, a network, or a combination thereof.

The joysticks 706 have respective trigger levers 36, which can be operated in order to energize the motor 42.

Although certain preferred embodiments of the present invention have been shown and described in detail, it should be understood that various changes and modifications may be made to the embodiments without departing from the scope of the invention as set forth in the appended claims.

What is claimed is:

1. A medical manipulator, comprising:
    a drive member;
    a transmitting member for transmitting a drive force to an end effector;
    a main shaft, the transmitting member being movably supported on the main shaft;
    an arcuate driven member integrally mounted on the transmitting member near a proximal end thereof, the arcuate driven member having an arcuate convex surface that is convex toward the proximal end of the transmitting member and a cavity that is non-convex toward a distal end of the transmitting member, the cavity being disposed within a virtual circle, a portion of which is represented by the arcuate convex surface;
    a cylindrical return member fixedly mounted on the main shaft between the arcuate driven member and the distal end of the transmitting member; and
    an annular flexible member having a portion connected to the drive member and trained at least one turn around and extending between the arcuate convex surface and the cylindrical return member,
    wherein when the drive member is moved toward a proximal end of the manipulator in order to pull the annular flexible member, the arcuate driven member is moved together with the transmitting member toward the distal end of the manipulator, and the cylindrical return member includes a proximal-end portion that enters the cavity, and
    wherein the medical manipulator actuates an end effector on a distal end thereof in response to movement of the drive member.

2. The medical manipulator according to claim 1, wherein the cavity is defined by an arcuate concave surface, which is open toward the distal end of the transmitting member.

3. The medical manipulator according to claim 2, wherein when the drive member is moved toward the proximal end of the manipulator in order to pull the annular flexible member, the arcuate driven member is moved together with the transmitting member toward the distal end of the manipulator, and the proximal-end portion of the cylindrical return member enters the cavity defined by the arcuate concave surface beyond a chord line that interconnects opposite concave ends of the arcuate concave surface.

4. The medical manipulator according to claim 2, wherein the arcuate concave surface is represented by an arc having a radius of curvature which is equal to a radius of the cylindrical return member as viewed in a plane, or which is greater than the radius of the cylindrical return member as viewed in the plane.

5. The medical manipulator according to claim 1, further comprising:
    a second end effector drive mechanism including the drive member, the end effector, the arcuate driven member, the cylindrical return member, the flexible member, a cylindrical idle member disposed more closely to the proximal end of the manipulator than the transmitting member, and a cylindrical guide member disposed between the cylindrical idle member and the transmitting member;
    a cylindrical driven member mounted on the transmitting member near the proximal end thereof;
    a first end effector drive mechanism including a drive member, a flexible member, a cylindrical idle member, the cylindrical driven member, and a cylindrical guide member; and
    a drive member moving mechanism for moving the drive member of the first end effector drive mechanism and the drive member of the second end effector drive mechanism in opposite directions.

6. The medical manipulator according to claim 5, wherein the cylindrical idle member comprises a cylinder having a diameter greater than a diameter of the cylindrical guide member.

7. The medical manipulator according to claim 1, wherein the arcuate convex surface is represented by an arc having a radius of curvature which is equal to a radius of the cylindrical return member as viewed in a plane.

8. The medical manipulator according to claim 7, wherein the arcuate convex surface is represented by an arc having a central angle ranging from 140° to 220° as viewed in the plane.

9. The medical manipulator according to claim 1, wherein the main shaft supports thereon the drive member, the arcuate driven member, and the cylindrical return member, the medical manipulator further including a pin supported on the main shaft, the pin being of a cantilevered structure, the cylindrical return member being rotatably supported on the pin.

10. The medical manipulator according to claim 1, further comprising:
a manually operable input unit, the drive member being mechanically connected to the manually operable input unit.

11. A medical manipulator comprising:
an end effector;
a transmitting member that transmits a drive force to the end effector;
a main shaft, the transmitting member being movably supported on the main shaft; and
first and second end effector drive mechanisms that move the transmitting member in opposite directions,
wherein the first end effector mechanism includes:
a first drive member disposed on a proximal end portion of the transmitting member, the first drive member being movable in opposite directions,
a cylindrical idle member disposed more closely to a distal end of the first end effector drive mechanism than the first drive member,
a cylindrical driven member disposed, on the transmitting member, more closely to the distal end of the first end effector drive mechanism than the cylindrical idle member,
a cylindrical guide member disposed between the cylindrical idle member and the cylindrical driven member, and
a first annular flexible member extending on opposite sides of the cylindrical idle member, crossing between the cylindrical guide member and the cylindrical driven member, extending on opposite sides of the cylindrical guide member in an axially shifted position, and trained around the cylindrical driven member, the first annular flexible member having a portion connected to the first drive member,
wherein when the first drive member is moved toward a proximal end of the manipulator in order to pull the first annular flexible member, the transmitting member is moved toward the proximal end of the manipulator,
wherein the second end effector drive mechanism includes:
a second drive member disposed on the proximal end portion of the transmitting member, the second drive member being movable in opposite directions,
an integral driven member integrally mounted on the transmitting member near the proximal end thereof,
a cylindrical return member fixedly mounted on the main shaft between the integral driven member and a distal end of the transmitting member, and
a second annular flexible member having a portion connected to the second drive member and trained at least one turn around and extending between the integral driven member and the cylindrical return member,
wherein when the second drive member is moved toward a proximal end of the manipulator in order to pull the second annular flexible member, the transmitting member is moved toward the cylindrical return member, and
wherein, assuming a direction from the cylindrical guide member toward the cylindrical driven member is referred to as a Z direction, the cylindrical guide member and the cylindrical driven member have respective axes extending out of parallelism with each other as viewed from the Z direction, such that the first annular flexible member has outward and inward stretched sections that extend in the Z direction between the cylindrical guide member and the cylindrical driven member.

12. The medical manipulator according to claim 11, wherein the cylindrical driven member has a cylindrical driven member groove formed in a side surface thereof for circumferentially guiding the first annular flexible member.

13. The medical manipulator according to claim 11, wherein the cylindrical guide member comprises a first layer guide pulley for guiding either one of an outward stretched section and an inward stretched section of the first annular flexible member, and a second layer guide pulley for guiding the other of the stretched sections of the first annular flexible member at a position which is axially displaced a distance $\Delta$ from the stretched section of the first annular flexible member that is guided by the first layer guide pulley; and
wherein the first annular flexible member has a turn trained around the cylindrical driven member and having opposite ends which are displaced from each other by the distance $\Delta$ in an axial direction of the cylindrical guide member.

14. The medical manipulator according to claim 11, wherein the cylindrical idle member comprises a first layer idle pulley and a second layer idle pulley, which are held in coaxial alignment with each other and disposed parallel to each other.

15. The medical manipulator according to claim 11, wherein the first annular flexible member comprises a single wire having opposite ends secured to each other at a position other than a junction where the first annular flexible member is connected to the first drive member.

16. The medical manipulator according to claim 11, further comprising:
a manually operable input unit, the first drive member being mechanically connected to the manually operable input unit.

17. The medical manipulator according to claim 11, wherein the second end effector drive mechanism includes a second cylindrical driven member and a second cylindrical guide member,
wherein the medical manipulator further comprises a drive member moving mechanism for moving the first drive member of the first end effector drive mechanism and the second drive member of the second end effector drive mechanism in opposite directions,
wherein the cylindrical return member is disposed more closely to a distal end of the second end effector drive mechanism than the second cylindrical driven member, and
wherein the second annular flexible member is trained around and extends between the second cylindrical driven member and the cylindrical return member of the second end effector drive mechanism, the second cylindrical guide member and the second cylindrical driven member having respective axes extending parallel to each other.

18. The medical manipulator according to claim 17, wherein the cylindrical driven member of the first end effector drive mechanism comprises a pulley rotatably supported on the transmitting member, and
wherein the second cylindrical driven member of the second end effector drive mechanism is integral with the transmitting member.

19. The medical manipulator according to claim 18, wherein the end effector comprises an openable and closable gripper;
wherein the first annular flexible member of the first end effector drive mechanism is held under higher tension when the gripper is closed; and wherein the second annular flexible member of the second end effector drive mechanism is held under higher tension when the gripper is opened.

* * * * *